US008759097B2

(12) United States Patent
Qian et al.

(10) Patent No.: US 8,759,097 B2
(45) Date of Patent: Jun. 24, 2014

(54) INHIBITION OF DYNAMIN RELATED PROTEIN 1 TO PROMOTE CELL DEATH

(75) Inventors: Wei Qian, Pittsburgh, PA (US); Bennett Van Houten, Pittsburgh, PA (US)

(73) Assignee: University of Pittsburgh—of the Commonwealth System of Higher Eduction, Pittsburgh, PA (US)

(*) Notice: Subject to any disclaimer, the term of this patent is extended or adjusted under 35 U.S.C. 154(b) by 0 days.

(21) Appl. No.: 13/450,345

(22) Filed: Apr. 18, 2012

(65) Prior Publication Data

US 2012/0294956 A1  Nov. 22, 2012

Related U.S. Application Data

(60) Provisional application No. 61/476,759, filed on Apr. 19, 2011.

(51) Int. Cl.
*A61K 31/517* (2006.01)
*A61P 35/00* (2006.01)
*A61K 38/38* (2006.01)
*C12N 5/09* (2010.01)

(52) U.S. Cl.
USPC ........ 435/375; 514/15.2; 514/266.3; 424/649

(58) Field of Classification Search
USPC ............... 435/375; 514/266.3, 15.2; 424/649; 544/285
See application file for complete search history.

(56) References Cited

U.S. PATENT DOCUMENTS

| 2005/0038051 | A1 | 2/2005 | Nunnari et al. |
| 2008/0287473 | A1 | 11/2008 | Nunnari et al. |

OTHER PUBLICATIONS

Chiang et al. Nuclear expression of dynamin-related protein 1 in lung adenocarcinomas. Modern Pathology (2009) 22, 1139-1150.
Cereghetti et al. Inhibition of Drp1-dependent mitochondrial fragmentation and apoptosis by a polypeptide antagonist of calcineurin. Cell Death and Differentiation (2010) 17, 1785-1794; doi:10.1038/cdd.2010.61; published online May 21, 2010.
Rehman et al. Inhibition of mitochondrial fission prevents cell cycle progression in lung cancer. The FASEB Journal article fj.11-196543. Published online Feb. 13, 2012.
David J. Stewart Tumor and host factors that may limit efficacy of chemotherapy in non-small cell and small lung cancer. Critical Reviews in Oncology/Hematology 75 (2010) 173-234.
Matthew Tillman Mason Fall 2010 PIM1 Inhibits DRP1 Promoting Cardiac Myocyte Survival. A theses Presented to thwe faculty of San Diego State University. In Partial Fulfillment of the requirements for the Degree Master of Science in Bioiogy.
Cassidy-Stone et al. Chemical Inhibition of the Mitochondrial Division Dynamin Reveals Its Role in Bax/Bak-Dependent Mitochondrial Outer Membrane Permeabilization.
Grohm et al. Inhibition of DRP1 Provides Neuroprotection in Vitro and in Vitro.

(Continued)

*Primary Examiner* — Savitha Rao
(74) *Attorney, Agent, or Firm* — Baker Botts, LLP

(57) ABSTRACT

The present invention relates to compositions and methods for reducing cell proliferation and/or promoting cell death by inhibiting Drp1. It is based, at least in part, on the discoveries that (i) Drp1 disruption-induced mitochondrial hyperfusion is functionally linked to the cell cycle regulation apparatus, so that Drp1 inhibition results in a disruption of the cell cycle and DNA aberrancies; (ii) inhibition of both Drp1 and ATR are synthetic lethal causing increased DNA damage and apoptotic cell death; and (iii) even in resistant cell lines, Drp1 inhibitor (e.g., mdivi-1) together with a second antiproliferative agent (e.g., cisplatin or carboplatin) act synergistically to promote apoptosis. Accordingly, the present invention provides for novel anticancer strategies.

14 Claims, 18 Drawing Sheets

(56) References Cited

OTHER PUBLICATIONS

Figure 1:
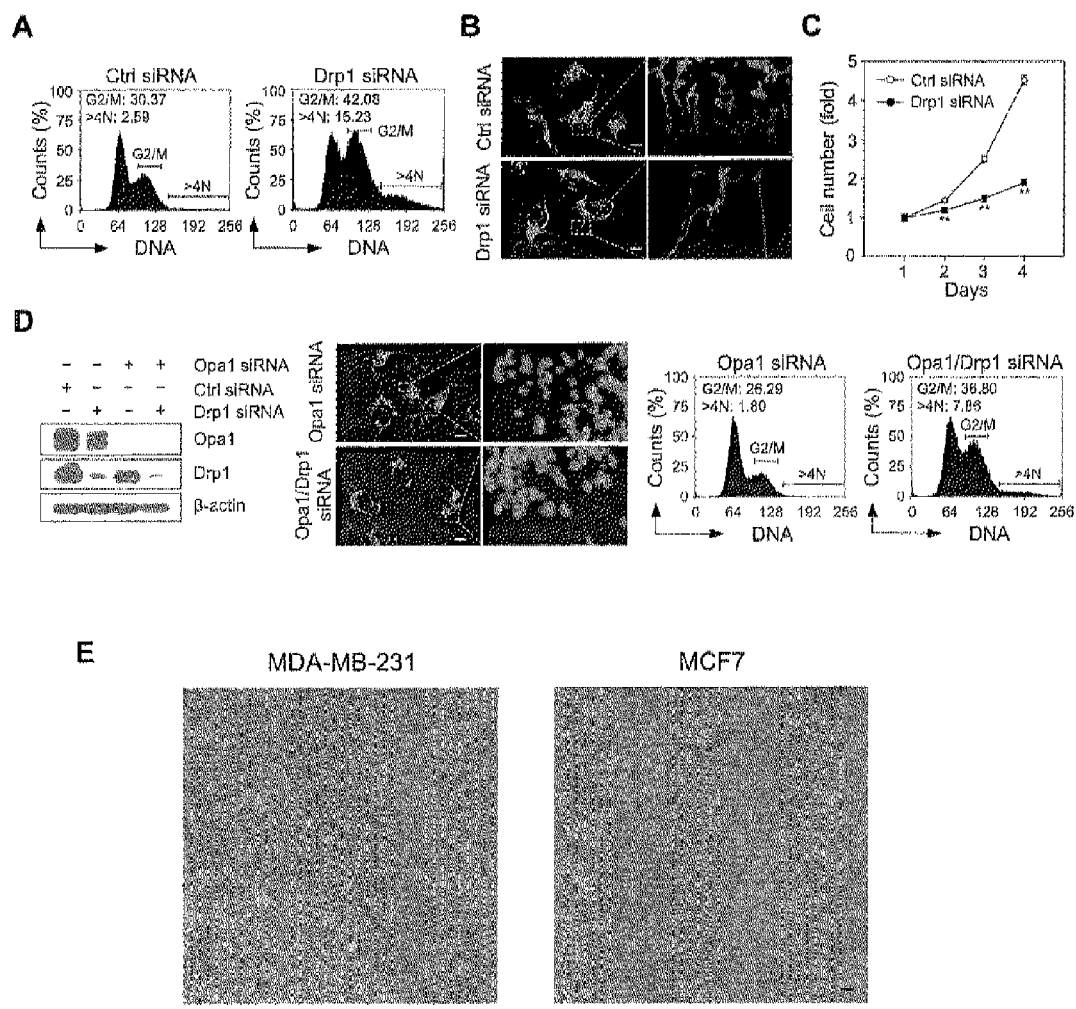
Figure 2:
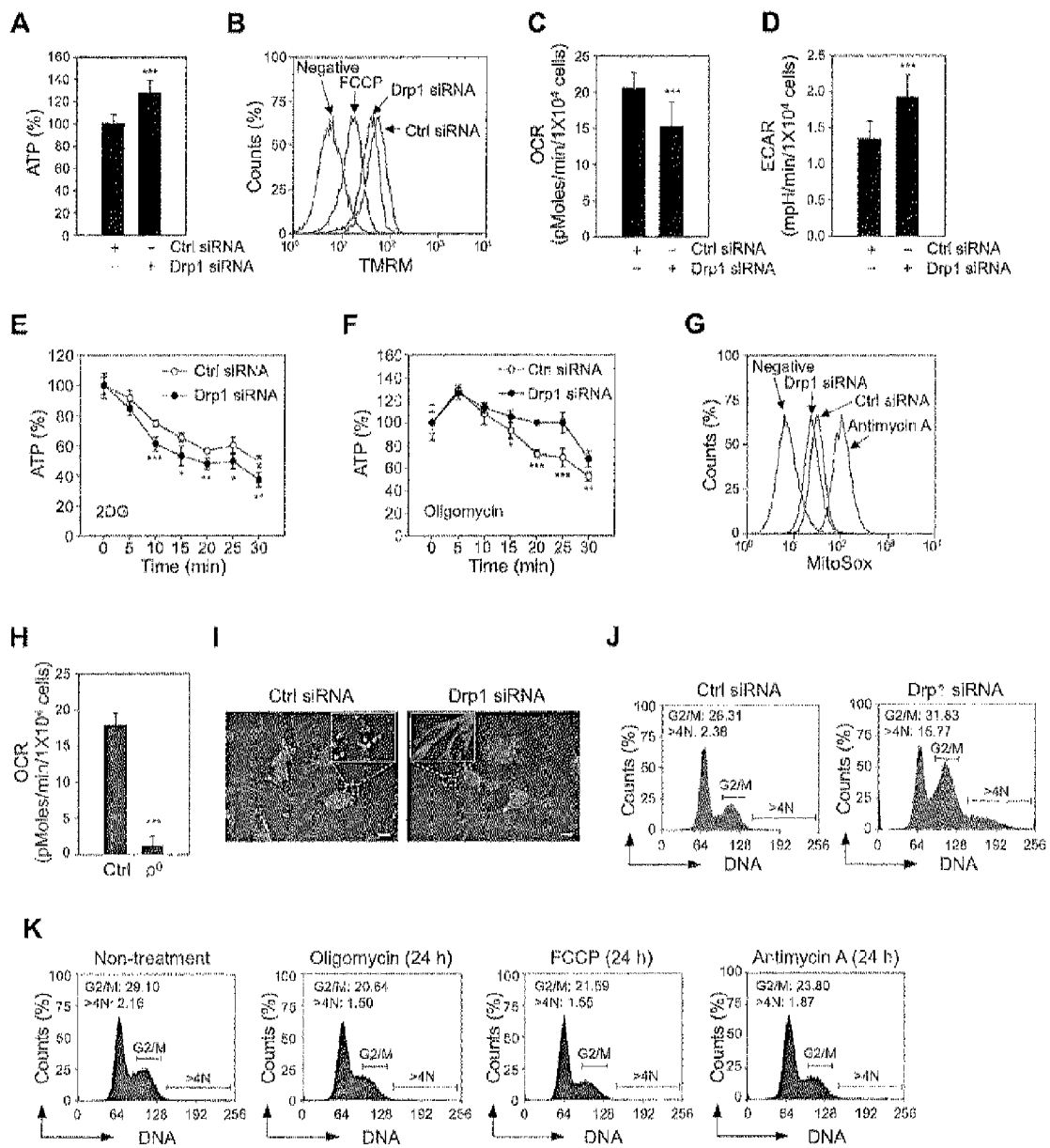

Bartkova, et al., "DNA Damage Response as a Candidate Anti-Cancer Barrier in early Human Tumorigenesis", *Nature*, 434:864-870 (2005).
Cassidy-Stone, et al., "Chemical Inhibition of the Mitochondrial Division Dynamin Reveals Its Role in Bax/Bak-Dependent Mitochondrial Outer Membrane Permeabilization", *Developmental Cell*, 14:193-204 (2008).
Cho, et al., "S-Nitrosylation of Drp1 Mediates β-Amyloid-Related Mitochondrial Fission and Neuronal Injury", *Science*, 324:102-105 (2009).
Cimprich, et al., "ATR: An Essential Regulator of Genome Integrity", *Nature Reviews: Molecular Cell Biology*, 9:616-627 (2008).
Cipolat, et al., "OPA1 requires Mitofusin 1 to Promote Mitochondrial Fusion", *PNAS*, 101(45):15927-15932 (2004).
Crosio, et al., "Mitotic Phosphorylation of Histone H3: Spatio-Temporal Regulation by Mammalian Aurora Kinases", *Molecular and Cellular Biology*, 22(3):874-885 (2002).
Dorée, et al., "From Cdc2 to Cdk1: When Did the Cell Cycle Kinase Join Its Cyclin Partner?", *Journal of Cell Science*, 115(12):2461-2464 (2002).
Ekholm, et al., "Regulation of $G_1$ Cyclin-Dependent Kinases in the Mammalian Cell Cycle", *Current Opinion in Cell Biology*, 12:676-684 (2000).
Ekholm, et al., "Accumulation of Cyclin E Is Not a Prerequisite for Passage Through the Restriction Point", *Molecular and Cellular Biology*, 21(9):3256-3265 (2001).
Ekholm-Reed, et al., "Deregulation of Cyclin E in Human Cells Interferes With Prereplication Complex Assembly", *The Journal of Cell Biology*, 165(6):789-800 (2004).
Fukasawa, "Oncogenes and Tumor Suppressors Take on Centrosomes", *Nature Reviews: Cancer*, 7:911-924 (2007).
Ganem, et al., "A Mechanism Linking Extra Centrosomes to Chromosomal Instability", *Nature*, 460:278-283 (2009).
Gorgoulis, et al., "Activation of the DNA Damage Checkpoint and Genomic Instability in Human Precancerous Lesions", *Nature*, 434:907-913 (2005).
Green, et al., "Snapshot: Mitochondrial Quality Control", *Cell*, 147:950.e1 (2011).
Grohm, et al., "Inhibition of Drp1 Provides Neuroprotection in vitro and in vivo", *Cell Death and Differentiation*, pp. 1-13 (2012).
Hemerly, et al., "Orel Controls Centriole and Centrosome Copy Number In Human Cells", *Science*, 323(5915):789-793 (2009).
Inane, et al., "A Centrosome-Autonomous Signal That Involves Centriole Disengagement Peiinits Centrosome Duplication in G2 Phase After DNA Damage", *Molecular Biology of the Cell*, 21:3866-3877 (2010).
Ishihara, et al., "Mitochondrial Fission Factor Drp1 Essential for Embryonic Development and Synapse Formation in Mice", *Nature Cell Biology*, 11(8):958-967 and Supplementary Information: pp. 1-8 (2009).
Jones, et al., "AMP—Activated Protein Kinase Induces a p53—Dependent Metabolic Checkpoint", *Molecular Cell*, 18:283-293 (2005).
Kanda, et al., "Histone-GFP Fusion Protein Enables Sensitive Analysis of Chromosome Dynamics in Living Mammalian Cells", *Current Biology*, 8:377-385 (1998).
Kashatus, et al., "RALA and RALBP1 Regulate Mitochondrial Fission At Mitosis", *Nature Cell Biology*, 13 (9): 1108-1115 (2011).
Kastan, et al., "Cell-Cycle Checkpoints and Cancer", *Nature*, 432:316-323 (2004).
Keck, et al., "Cyclin E Overexpression Impairs Progression Through Mitosis by Inhibitinh $APC^{Cdh1}$", *The Journal of Cell Biology*, 178(3):371-385 (2007).
King, et al., "Isolation of Human Cell Lines Lacking Mitochondrial DNA", *Methods in Enzymology*, 264:304-313 (1996).
Labrousse, et al., "*C. elegans* Dynamin-Related Protein DRP-1 Controls Severing of the Mitochondrial Outer Membrane", *Molecular Cell*, 4:815-826 (1999).

Lew, et al., "Regulatory roles of Cyclin Dependent Kinase Phosphorylation in Cell Cycle Control", *Current Opinion in Cell Biology*, 8:795-804 (1996).
Liberal, et al., "Cyclin-Dependent Kinase Subunit (Cks) 1 or Cks2 Overexpression Overrides the DNA Damage Response Barrier Triggered by Activated Oncoproteins", *PNAS Early Edition*, 6 pages (2011).
Listovsky, et al., "Mammalian Cdh1/Fzr Mediates Its Own Degradation", *The EMBO Journal*, 23:1619-1626 (2004).
Macia, et al., "Dynasore, A Cell-Permeable Inhibitor of Dynamin", *Developmental Cell*, 10:839-850 (2006).
Malena, et al., "Inhibition of Mitochondrial Fission Favours Mutant Over Wild-Type Mitochondrial DNA", *Human Molecular Genetics*, 18(18):3407-3416 (2009).
Mandal, et al., "Mitochondrial Regulation of Cell Cycle Progression During Development As Revealed by the *Tenured* Mutation in *Drosophila*", *Developmental Cell*, 9:843-854 (2005).
Matsumoto, et al., "Calcium, Calmodulin, and CaMKII Requirement for Initiation of Centrosome Duplication in *Xenopus* Egg Extracts", *Science*, 295:499-502 (2002).
Mitra, et al., "A Hyperfused Mitochondrial State Achieved At $G_1$-S Regulates Cyclin E Buildup and Entry Into S Phase", *PNAS*, 106(29):11960-11965 (2009).
Murga, et al., "A Mouse Model of ATR-Seckel Chows Embryonic Replicative Stress and Accelerated Aging", *Nature Genetics*, 41(8):891-898 (2009).
Nakayama, et al., "Targeted Disruption of Skp2 Results in Accumulation of Cyclin E and $p27^{Kip1}$, Polyploidy and Centrosome Overduplication", *The EMBO Journal*, 19(9):2069-2081 (2000).
Norbury, et al., "Regulatory Phosphorylation of the $p34^{cdc2}$ Protein Kinase in Vertebrates", *The EMBO Journal*, 10(11):3321-3329 (1991).
Owusu-Ansah, et al., "Distinct Mitochondrial Retrograde Signals Control the G1-S Cell Cycle Checkpoint", *Nature Genetics*, 40(3):356-361 (2008).
Parone, et al., "Preventing Mitochondrial Fission Impairs Mitochondrial Function and Leads to Loss of Mitochondrial DNA", *PlosOne*, 3(9):e3257 (2008).
Qian, et al., "Alterations in Bioenergetics Due to Changes in Mitochodrial DNA Copy Number", *Methods*, 51:452-457 (2010).
Rajagopalan, et al., "Inactivation of hCDC4 Can Cause Chromosomal Instability", *Nature*, 428:77-81 (2004).
Rajagopalan, et al., "Aneuploidy and Cancer", *Nature*, 432:338-341 (2004).
Reaper, et al., "Selective Killing of ATM-Or p53-Deficient Cancer Cells Through Inhibition of ATR", *Nature Chemical Biology*, 7:428-430 (2011).
Smirnova, et al., "A Human Dynamin-Related Protein Controls the Distribution of Mitochondria", *The Journal of Cell Biology*, 143(2):351-358 (1998).
Smirnova, et al., "Dynamin-Related Protein Drp1 Is Required for Mitochondrial Division on Mammalian Cells", *Molecular Biology of the Cell*, 12:2245-2256 (2001).
Spruck, et al., "Deregulated Cyclin E Induces Chromosomes Instability", *Nature*, 401:297-300 (1999).
Sugioka, et al., "Fzo1, A Protein Involved in Mitochondrial Fusion, Inhibits Apoptosis", *The Journal of Biological Chemistry*, 279(50):52726-52734 (2004).
Taguchi, et al., "Mitotic Phosphorylation of Dynamin-Related GTPase Drp1 Participates in Mitochondrial Fission", *The Journal of Biological Chemistry*, 282(15):11521-11529 (2007).
Toledo, et al., "ATR Signaling Can Drive Cells Into Senescene in the Absence of DNA Breaks", *Genes & Development*, 22:297-302 (2008).
Toledo, et al., "A Cell-Based Screen Identifies ATR Inhibitors With Synthetic Lethal Properties for Cancer-Associated Mutations", *Nature Structural & Molecular Biology*, 18(6):721-728 (2011).
Twig, et al., "Fission and Selective Fusion Govern Mitochondrial Segregation and Elimination by Autophagy", *The EMBO Journal*, 27:433-446 (2008).

(56) References Cited

OTHER PUBLICATIONS

Wakabayashi, et al., "The Dynamic-Related GTPase Drp1 Is Required for Embryonic and Brain Development in Mice", *The Journal of Cell Biology*, 186(6):805-816 (2009).

Wang, et al., "Dynamin-Like Protein 1 Reduction Underlies Mitochondrial Morphology and Distribution Abnormalities in Fibroblasts From Spradic Alzheimer's Disease Patients", *The American Journal of Pathology*, 173(2):470-482 (2008).

Warburg, et al., "The Metabolism of Tumors in the Body", *The Journal of General Physiology*, 8:519-530 (1927).

Waterham, et al., "A Lethal Defect of Mitochondrial and Peroxisomal Fission", *The New England Journal of Medicine*, 356:1736-1741 (2007).

Weinberg, et al., "Mitochondrial Metabolism and ROS Generation are Essential for Kras-Mediated Tumorigenicity", *PNAS*, 107(19):8788-8793 (2010).

Westerman, "Mitochondrial fusion and Fission in Cell Life and Death", *Nature Reviews: Molecular Cell Biology*, 11:872-884 (2010).

White, et al., "Irreversible Chromosome Damage Accumulates Rapidly in the Absence of ATM Kinase Activity", *Cell Cycle*, 7(9):1277-1284 (2008).

Yoon, et al., "Formation of Elongated Giant Mitochondria in DFO-Induced Cellular Senescence: Involvement of Enhanced Fusion Process Through Modulation of Fis1", *Journal of Cellular Physiology*, 209:468-480 (2006).

Qian, et al., "Mitochondrial division inhibitor (mdivi-1) overcomes cisplatin resistance independent of dynami-related protein 9Drp1)", *American Association for Cancer Research, Annual Meeting 2013* in Walter E. Washington Convention Center, Washington, DC, Abstract No. 946, (Apr. 6-10, 2013).

Qian, et al., "Mitochodrial division inhibitor 1 (mdivi-1) overcomes cisplatin resistance independent of dynamin-related protein 1 (Drp1)", University of Pittsburgh, poster presented in Boston, MA (2013).

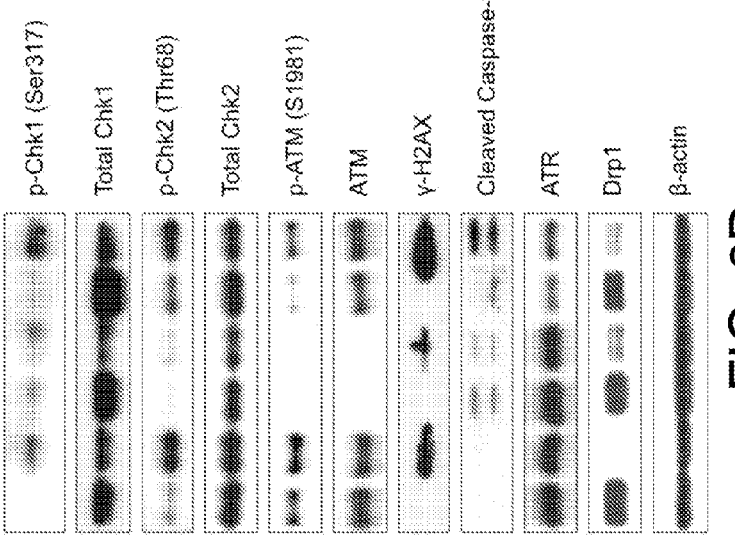
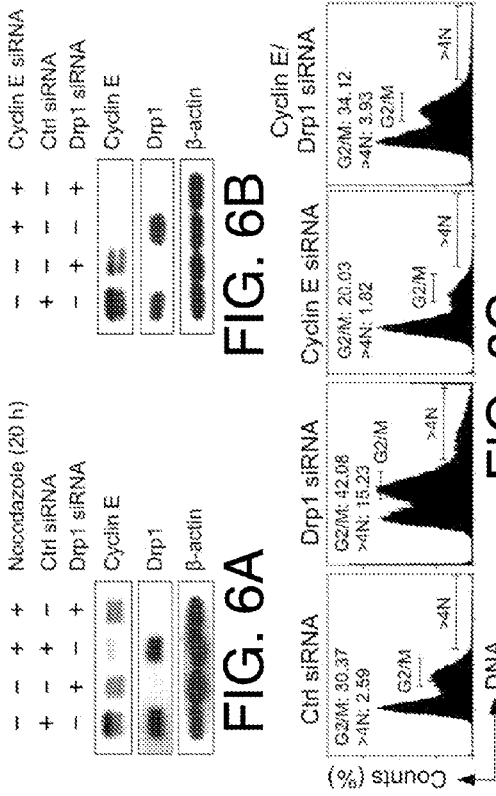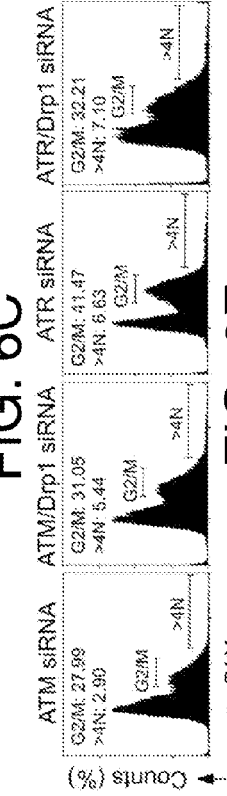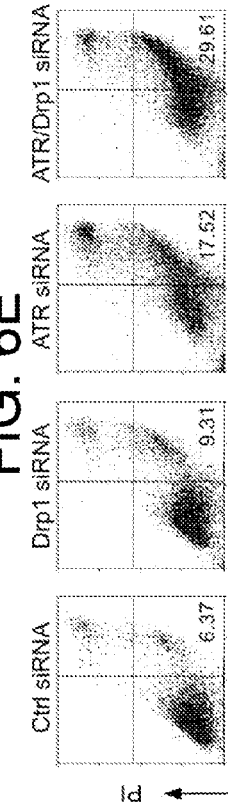

Figure 9A-C
A
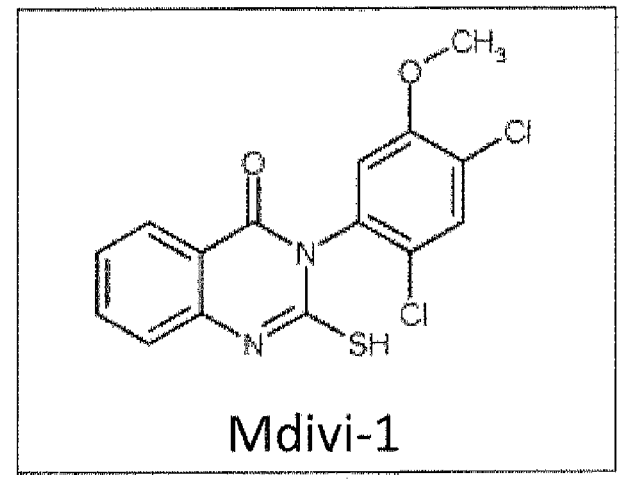
Mdivi-1
B
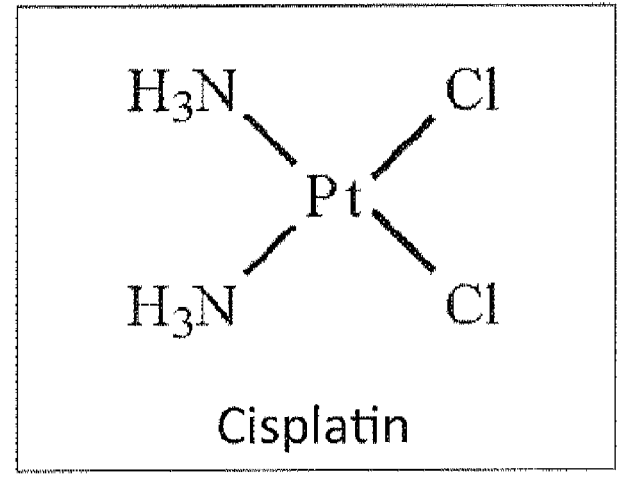
Cisplatin
C
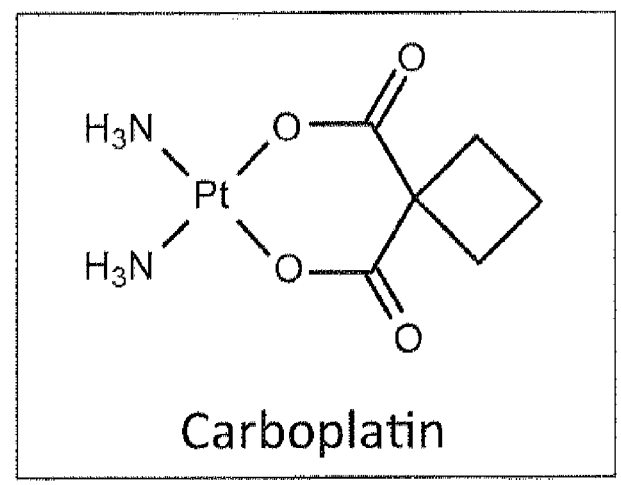
Carboplatin

Figure 10A-B
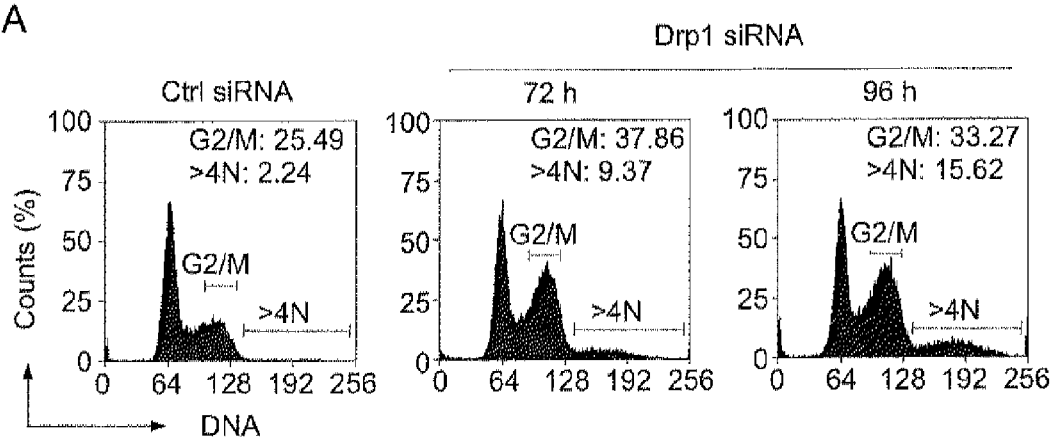
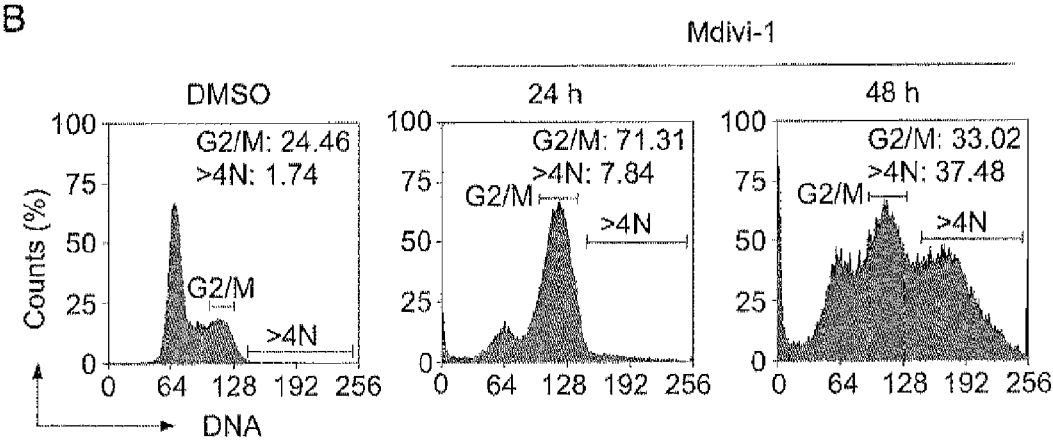

Figure 13A-C

SEQUENCE LISTING

```
<160> NUMBER OF SEQ ID NOS: 13

<210> SEQ ID NO 1
<211> LENGTH: 736
<212> TYPE: PRT
<213> ORGANISM: Homo sapiens

<400> SEQUENCE: 1

Met Glu Ala Leu Ile Pro Val Ile Asn Lys Leu Gln Asp Val Phe Asn
1               5                   10                  15

Thr Val Gly Ala Asp Ile Ile Gln Leu Pro Gln Ile Val Val Val Gly
            20                  25                  30

Thr Gln Ser Ser Gly Lys Ser Ser Val Leu Glu Ser Leu Val Gly Arg
        35                  40                  45

Asp Leu Leu Pro Arg Gly Thr Gly Ile Val Thr Arg Arg Pro Leu Ile
    50                  55                  60

Leu Gln Leu Val His Val Ser Gln Glu Asp Lys Arg Lys Thr Thr Gly
65                  70                  75                  80

Glu Glu Asn Gly Val Glu Ala Glu Glu Trp Gly Lys Phe Leu His Thr
                85                  90                  95

Lys Asn Lys Leu Tyr Thr Asp Phe Asp Glu Ile Arg Gln Glu Ile Glu
            100                 105                 110
```

-continued

```
Asn Glu Thr Glu Arg Ile Ser Gly Asn Asn Lys Gly Val Ser Pro Glu
        115                 120                 125

Pro Ile His Leu Lys Ile Phe Ser Pro Asn Val Val Asn Leu Thr Leu
130                 135                 140

Val Asp Leu Pro Gly Met Thr Lys Val Pro Val Gly Asp Gln Pro Lys
145                 150                 155                 160

Asp Ile Glu Leu Gln Ile Arg Glu Leu Ile Leu Arg Phe Ile Ser Asn
                165                 170                 175

Pro Asn Ser Ile Ile Leu Ala Val Thr Ala Ala Asn Thr Asp Met Ala
                180                 185                 190

Thr Ser Glu Ala Leu Lys Ile Ser Arg Glu Val Asp Pro Asp Gly Arg
                195                 200                 205

Arg Thr Leu Ala Val Ile Thr Lys Leu Asp Leu Met Asp Ala Gly Thr
210                 215                 220

Asp Ala Met Asp Val Leu Met Gly Arg Val Ile Pro Val Lys Leu Gly
225                 230                 235                 240

Ile Ile Gly Val Val Asn Arg Ser Gln Leu Asp Ile Asn Asn Lys Lys
                245                 250                 255

Ser Val Thr Asp Ser Ile Arg Asp Glu Tyr Ala Phe Leu Gln Lys Lys
                260                 265                 270

Tyr Pro Ser Leu Ala Asn Arg Asn Gly Thr Lys Tyr Leu Ala Arg Thr
                275                 280                 285

Leu Asn Arg Leu Leu Met His His Ile Arg Asp Cys Leu Pro Glu Leu
290                 295                 300

Lys Thr Arg Ile Asn Val Leu Ala Ala Gln Tyr Gln Ser Leu Leu Asn
305                 310                 315                 320

Ser Tyr Gly Glu Pro Val Asp Asp Lys Ser Ala Thr Leu Leu Gln Leu
                325                 330                 335

Ile Thr Lys Phe Ala Thr Glu Tyr Cys Asn Thr Ile Glu Gly Thr Ala
                340                 345                 350

Lys Tyr Ile Glu Thr Ser Glu Leu Cys Gly Gly Ala Arg Ile Cys Tyr
                355                 360                 365

Ile Phe His Glu Thr Phe Gly Arg Thr Leu Glu Ser Val Asp Pro Leu
370                 375                 380

Gly Gly Leu Asn Thr Ile Asp Ile Leu Thr Ala Ile Arg Asn Ala Thr
385                 390                 395                 400

Gly Pro Arg Pro Ala Leu Phe Val Pro Glu Val Ser Phe Glu Leu Leu
                405                 410                 415

Val Lys Arg Gln Ile Lys Arg Leu Glu Glu Pro Ser Leu Arg Cys Val
                420                 425                 430

Glu Leu Val His Glu Glu Met Gln Arg Ile Ile Gln His Cys Ser Asn
                435                 440                 445

Tyr Ser Thr Gln Glu Leu Leu Arg Phe Pro Lys Leu His Asp Ala Ile
450                 455                 460

Val Glu Val Val Thr Cys Leu Leu Arg Lys Arg Leu Pro Val Thr Asn
465                 470                 475                 480

Glu Met Val His Asn Leu Val Ala Ile Glu Leu Ala Tyr Ile Asn Thr
                485                 490                 495

Lys His Pro Asp Phe Ala Asp Ala Cys Gly Leu Met Asn Asn Asn Ile
                500                 505                 510

Glu Glu Gln Arg Arg Asn Arg Leu Ala Arg Glu Leu Pro Ser Ala Val
                515                 520                 525

Ser Arg Asp Lys Ser Ser Lys Val Pro Ser Ala Leu Ala Pro Ala Ser
530                 535                 540
```

```
Gln Glu Pro Ser Pro Ala Ala Ser Ala Glu Ala Asp Gly Lys Leu Ile
545                 550                 555                 560

Gln Asp Ser Arg Arg Glu Thr Lys Asn Val Ala Ser Gly Gly Gly Gly
                565                 570                 575

Val Gly Asp Gly Val Gln Glu Pro Thr Thr Gly Asn Trp Arg Gly Met
            580                 585                 590

Leu Lys Thr Ser Lys Ala Glu Glu Leu Leu Ala Glu Glu Lys Ser Lys
        595                 600                 605

Pro Ile Pro Ile Met Pro Ala Ser Pro Gln Lys Gly His Ala Val Asn
    610                 615                 620

Leu Leu Asp Val Pro Val Pro Val Ala Arg Lys Leu Ser Ala Arg Glu
625                 630                 635                 640

Gln Arg Asp Cys Glu Val Ile Glu Arg Leu Ile Lys Ser Tyr Phe Leu
                645                 650                 655

Ile Val Arg Lys Asn Ile Gln Asp Ser Val Pro Lys Ala Val Met His
                660                 665                 670

Phe Leu Val Asn His Val Lys Asp Thr Leu Gln Ser Glu Leu Val Gly
            675                 680                 685

Gln Leu Tyr Lys Ser Ser Leu Leu Asp Asp Leu Leu Thr Glu Ser Glu
        690                 695                 700

Asp Met Ala Gln Arg Arg Lys Glu Ala Ala Asp Met Leu Lys Ala Leu
705                 710                 715                 720

Gln Gly Ala Ser Gln Ile Ile Ala Glu Ile Arg Glu Thr His Leu Trp
                725                 730                 735

<210> SEQ ID NO 2
<211> LENGTH: 710
<212> TYPE: PRT
<213> ORGANISM: Homo sapiens

<400> SEQUENCE: 2

Met Glu Ala Leu Ile Pro Val Ile Asn Lys Leu Gln Asp Val Phe Asn
1               5                   10                  15

Thr Val Gly Ala Asp Ile Ile Gln Leu Pro Gln Ile Val Val Val Gly
            20                  25                  30

Thr Gln Ser Ser Gly Lys Ser Ser Val Leu Glu Ser Leu Val Gly Arg
        35                  40                  45

Asp Leu Leu Pro Arg Gly Thr Gly Ile Val Thr Arg Arg Pro Leu Ile
    50                  55                  60

Leu Gln Leu Val His Val Ser Gln Glu Asp Lys Arg Lys Thr Thr Gly
65                  70                  75                  80

Glu Glu Asn Gly Val Glu Ala Glu Glu Trp Gly Lys Phe Leu His Thr
                85                  90                  95

Lys Asn Lys Leu Tyr Thr Asp Phe Asp Glu Ile Arg Gln Glu Ile Glu
            100                 105                 110

Asn Glu Thr Glu Arg Ile Ser Gly Asn Asn Lys Gly Val Ser Pro Glu
        115                 120                 125

Pro Ile His Leu Lys Ile Phe Ser Pro Asn Val Asn Leu Thr Leu
    130                 135                 140

Val Asp Leu Pro Gly Met Thr Lys Val Pro Val Gly Asp Gln Pro Lys
145                 150                 155                 160

Asp Ile Glu Leu Gln Ile Arg Glu Leu Ile Leu Arg Phe Ile Ser Asn
                165                 170                 175

Pro Asn Ser Ile Ile Leu Ala Val Thr Ala Ala Asn Thr Asp Met Ala
            180                 185                 190
```

```
Thr Ser Glu Ala Leu Lys Ile Ser Arg Glu Val Asp Pro Asp Gly Arg
            195                 200                 205

Arg Thr Leu Ala Val Ile Thr Lys Leu Asp Leu Met Asp Ala Gly Thr
        210                 215                 220

Asp Ala Met Asp Val Leu Met Gly Arg Val Ile Pro Val Lys Leu Gly
225                 230                 235                 240

Ile Ile Gly Val Val Asn Arg Ser Gln Leu Asp Ile Asn Asn Lys Lys
                245                 250                 255

Ser Val Thr Asp Ser Ile Arg Asp Glu Tyr Ala Phe Leu Gln Lys Lys
            260                 265                 270

Tyr Pro Ser Leu Ala Asn Arg Asn Gly Thr Lys Tyr Leu Ala Arg Thr
        275                 280                 285

Leu Asn Arg Leu Leu Met His His Ile Arg Asp Cys Leu Pro Glu Leu
        290                 295                 300

Lys Thr Arg Ile Asn Val Leu Ala Ala Gln Tyr Gln Ser Leu Leu Asn
305                 310                 315                 320

Ser Tyr Gly Glu Pro Val Asp Asp Lys Ser Ala Thr Leu Leu Gln Leu
                325                 330                 335

Ile Thr Lys Phe Ala Thr Glu Tyr Cys Asn Thr Ile Glu Gly Thr Ala
            340                 345                 350

Lys Tyr Ile Glu Thr Ser Glu Leu Cys Gly Gly Ala Arg Ile Cys Tyr
        355                 360                 365

Ile Phe His Glu Thr Phe Gly Arg Thr Leu Glu Ser Val Asp Pro Leu
        370                 375                 380

Gly Gly Leu Asn Thr Ile Asp Ile Leu Thr Ala Ile Arg Asn Ala Thr
385                 390                 395                 400

Gly Pro Arg Pro Ala Leu Phe Val Pro Glu Val Ser Phe Glu Leu Leu
                405                 410                 415

Val Lys Arg Gln Ile Lys Arg Leu Glu Glu Pro Ser Leu Arg Cys Val
            420                 425                 430

Glu Leu Val His Glu Met Gln Arg Ile Ile Gln His Cys Ser Asn
        435                 440                 445

Tyr Ser Thr Gln Glu Leu Leu Arg Phe Pro Lys Leu His Asp Ala Ile
        450                 455                 460

Val Glu Val Val Thr Cys Leu Leu Arg Lys Arg Leu Pro Val Thr Asn
465                 470                 475                 480

Glu Met Val His Asn Leu Val Ala Ile Glu Leu Ala Tyr Ile Asn Thr
                485                 490                 495

Lys His Pro Asp Phe Ala Asp Ala Cys Gly Leu Met Asn Asn Asn Ile
            500                 505                 510

Glu Glu Gln Arg Arg Asn Arg Leu Ala Arg Glu Leu Pro Ser Ala Val
        515                 520                 525

Ser Arg Asp Lys Leu Ile Gln Asp Ser Arg Arg Glu Thr Lys Asn Val
        530                 535                 540

Ala Ser Gly Gly Gly Val Gly Asp Gly Val Gln Glu Pro Thr Thr
545                 550                 555                 560

Gly Asn Trp Arg Gly Met Leu Lys Thr Ser Lys Ala Glu Glu Leu Leu
                565                 570                 575

Ala Glu Glu Lys Ser Lys Pro Ile Pro Ile Met Pro Ala Ser Pro Gln
            580                 585                 590

Lys Gly His Ala Val Asn Leu Leu Asp Val Pro Val Pro Val Ala Arg
        595                 600                 605

Lys Leu Ser Ala Arg Glu Gln Arg Asp Cys Glu Val Ile Glu Arg Leu
```

```
              610                 615                 620
Ile Lys Ser Tyr Phe Leu Ile Val Arg Lys Asn Ile Gln Asp Ser Val
625                 630                 635                 640

Pro Lys Ala Val Met His Phe Leu Val Asn His Val Lys Asp Thr Leu
                645                 650                 655

Gln Ser Glu Leu Val Gly Gln Leu Tyr Lys Ser Ser Leu Leu Asp Asp
                660                 665                 670

Leu Leu Thr Glu Ser Glu Asp Met Ala Gln Arg Arg Lys Glu Ala Ala
                675                 680                 685

Asp Met Leu Lys Ala Leu Gln Gly Ala Ser Gln Ile Ile Ala Glu Ile
                690                 695                 700

Arg Glu Thr His Leu Trp
705                 710

<210> SEQ ID NO 3
<211> LENGTH: 699
<212> TYPE: PRT
<213> ORGANISM: Homo sapiens

<400> SEQUENCE: 3

Met Glu Ala Leu Ile Pro Val Ile Asn Lys Leu Gln Asp Val Phe Asn
1               5                   10                  15

Thr Val Gly Ala Asp Ile Ile Gln Leu Pro Gln Ile Val Val Val Gly
                20                  25                  30

Thr Gln Ser Ser Gly Lys Ser Ser Val Leu Glu Ser Leu Val Gly Arg
                35                  40                  45

Asp Leu Leu Pro Arg Gly Thr Gly Ile Val Thr Arg Arg Pro Leu Ile
                50                  55                  60

Leu Gln Leu Val His Val Ser Gln Glu Asp Lys Arg Lys Thr Thr Gly
65                  70                  75                  80

Glu Glu Asn Gly Val Glu Ala Glu Glu Trp Gly Lys Phe Leu His Thr
                85                  90                  95

Lys Asn Lys Leu Tyr Thr Asp Phe Asp Glu Ile Arg Gln Glu Ile Glu
                100                 105                 110

Asn Glu Thr Glu Arg Ile Ser Gly Asn Asn Lys Gly Val Ser Pro Glu
                115                 120                 125

Pro Ile His Leu Lys Ile Phe Ser Pro Asn Val Val Asn Leu Thr Leu
                130                 135                 140

Val Asp Leu Pro Gly Met Thr Lys Val Pro Val Gly Asp Gln Pro Lys
145                 150                 155                 160

Asp Ile Glu Leu Gln Ile Arg Glu Leu Ile Leu Arg Phe Ile Ser Asn
                165                 170                 175

Pro Asn Ser Ile Ile Leu Ala Val Thr Ala Ala Asn Thr Asp Met Ala
                180                 185                 190

Thr Ser Glu Ala Leu Lys Ile Ser Arg Glu Val Asp Pro Asp Gly Arg
                195                 200                 205

Arg Thr Leu Ala Val Ile Thr Lys Leu Asp Leu Met Asp Ala Gly Thr
                210                 215                 220

Asp Ala Met Asp Val Leu Met Gly Arg Val Ile Pro Val Lys Leu Gly
225                 230                 235                 240

Ile Ile Gly Val Val Asn Arg Ser Gln Leu Asp Ile Asn Asn Lys Lys
                245                 250                 255

Ser Val Thr Asp Ser Ile Arg Asp Glu Tyr Ala Phe Leu Gln Lys Lys
                260                 265                 270

Tyr Pro Ser Leu Ala Asn Arg Asn Gly Thr Lys Tyr Leu Ala Arg Thr
```

```
                    275                 280                 285
Leu Asn Arg Leu Leu Met His His Ile Arg Asp Cys Leu Pro Glu Leu
290                 295                 300
Lys Thr Arg Ile Asn Val Leu Ala Ala Gln Tyr Gln Ser Leu Leu Asn
305                 310                 315                 320
Ser Tyr Gly Glu Pro Val Asp Asp Lys Ser Ala Thr Leu Leu Gln Leu
                325                 330                 335
Ile Thr Lys Phe Ala Thr Glu Tyr Cys Asn Thr Ile Glu Gly Thr Ala
                340                 345                 350
Lys Tyr Ile Glu Thr Ser Glu Leu Cys Gly Gly Ala Arg Ile Cys Tyr
                355                 360                 365
Ile Phe His Glu Thr Phe Gly Arg Thr Leu Glu Ser Val Asp Pro Leu
                370                 375                 380
Gly Gly Leu Asn Thr Ile Asp Ile Leu Thr Ala Ile Arg Asn Ala Thr
385                 390                 395                 400
Gly Pro Arg Pro Ala Leu Phe Val Pro Glu Val Ser Phe Glu Leu Leu
                405                 410                 415
Val Lys Arg Gln Ile Lys Arg Leu Glu Glu Pro Ser Leu Arg Cys Val
                420                 425                 430
Glu Leu Val His Glu Glu Met Gln Arg Ile Ile Gln His Cys Ser Asn
                435                 440                 445
Tyr Ser Thr Gln Glu Leu Leu Arg Phe Pro Lys Leu His Asp Ala Ile
                450                 455                 460
Val Glu Val Val Thr Cys Leu Leu Arg Lys Arg Leu Pro Val Thr Asn
465                 470                 475                 480
Glu Met Val His Asn Leu Val Ala Ile Glu Leu Ala Tyr Ile Asn Thr
                485                 490                 495
Lys His Pro Asp Phe Ala Asp Ala Cys Gly Leu Met Asn Asn Asn Ile
                500                 505                 510
Glu Glu Gln Arg Arg Asn Arg Leu Ala Arg Glu Leu Pro Ser Ala Val
                515                 520                 525
Ser Arg Asp Lys Val Ala Ser Gly Gly Gly Val Gly Asp Gly Val
530                 535                 540
Gln Glu Pro Thr Thr Gly Asn Trp Arg Gly Met Leu Lys Thr Ser Lys
545                 550                 555                 560
Ala Glu Glu Leu Leu Ala Glu Glu Lys Ser Lys Pro Ile Pro Ile Met
                565                 570                 575
Pro Ala Ser Pro Gln Lys Gly His Ala Val Asn Leu Leu Asp Val Pro
                580                 585                 590
Val Pro Val Ala Arg Lys Leu Ser Ala Arg Glu Gln Arg Asp Cys Glu
                595                 600                 605
Val Ile Glu Arg Leu Ile Lys Ser Tyr Phe Leu Ile Val Arg Lys Asn
610                 615                 620
Ile Gln Asp Ser Val Pro Lys Ala Val Met His Phe Leu Val Asn His
625                 630                 635                 640
Val Lys Asp Thr Leu Gln Ser Glu Leu Val Gly Gln Leu Tyr Lys Ser
                645                 650                 655
Ser Leu Leu Asp Asp Leu Leu Thr Glu Ser Glu Asp Met Ala Gln Arg
                660                 665                 670
Arg Lys Glu Ala Ala Asp Met Leu Lys Ala Leu Gln Gly Ala Ser Gln
                675                 680                 685
Ile Ile Ala Glu Ile Arg Glu Thr His Leu Trp
690                 695
```

-continued

```
<210> SEQ ID NO 4
<211> LENGTH: 710
<212> TYPE: PRT
<213> ORGANISM: Homo sapiens

<400> SEQUENCE: 4

Met Glu Ala Leu Ile Pro Val Ile Asn Lys Leu Gln Asp Val Phe Asn
1               5                   10                  15

Thr Val Gly Ala Asp Ile Ile Gln Leu Pro Gln Ile Val Val Val Gly
            20                  25                  30

Thr Gln Ser Ser Gly Lys Ser Ser Val Leu Glu Ser Leu Val Gly Arg
        35                  40                  45

Asp Leu Leu Pro Arg Gly Thr Gly Ile Val Thr Arg Arg Pro Leu Ile
    50                  55                  60

Leu Gln Leu Val His Val Ser Gln Glu Asp Lys Arg Lys Thr Thr Gly
65                  70                  75                  80

Glu Glu Asn Gly Val Glu Ala Glu Trp Gly Lys Phe Leu His Thr
                85                  90                  95

Lys Asn Lys Leu Tyr Thr Asp Phe Asp Glu Ile Arg Gln Glu Ile Glu
            100                 105                 110

Asn Glu Thr Glu Arg Ile Ser Gly Asn Asn Lys Gly Val Ser Pro Glu
        115                 120                 125

Pro Ile His Leu Lys Ile Phe Ser Pro Asn Val Val Asn Leu Thr Leu
    130                 135                 140

Val Asp Leu Pro Gly Met Thr Lys Val Pro Val Gly Asp Gln Pro Lys
145                 150                 155                 160

Asp Ile Glu Leu Gln Ile Arg Glu Leu Ile Leu Arg Phe Ile Ser Asn
            165                 170                 175

Pro Asn Ser Ile Ile Leu Ala Val Thr Ala Ala Asn Thr Asp Met Ala
        180                 185                 190

Thr Ser Glu Ala Leu Lys Ile Ser Arg Glu Val Asp Pro Asp Gly Arg
    195                 200                 205

Arg Thr Leu Ala Val Ile Thr Lys Leu Asp Leu Met Asp Ala Gly Thr
210                 215                 220

Asp Ala Met Asp Val Leu Met Gly Arg Val Ile Pro Val Lys Leu Gly
225                 230                 235                 240

Ile Ile Gly Val Val Asn Arg Ser Gln Leu Asp Ile Asn Asn Lys Lys
            245                 250                 255

Ser Val Thr Asp Ser Ile Arg Asp Glu Tyr Ala Phe Leu Gln Lys Lys
        260                 265                 270

Tyr Pro Ser Leu Ala Asn Arg Asn Gly Thr Lys Tyr Leu Ala Arg Thr
    275                 280                 285

Leu Asn Arg Leu Leu Met His His Ile Arg Asp Cys Leu Pro Glu Leu
290                 295                 300

Lys Thr Arg Ile Asn Val Leu Ala Ala Gln Tyr Gln Ser Leu Leu Asn
305                 310                 315                 320

Ser Tyr Gly Glu Pro Val Asp Asp Lys Ser Ala Thr Leu Leu Gln Leu
            325                 330                 335

Ile Thr Lys Phe Ala Thr Glu Tyr Cys Asn Thr Ile Glu Gly Thr Ala
        340                 345                 350

Lys Tyr Ile Glu Thr Ser Glu Leu Cys Gly Gly Ala Arg Ile Cys Tyr
    355                 360                 365

Ile Phe His Glu Thr Phe Gly Arg Thr Leu Glu Ser Val Asp Pro Leu
370                 375                 380
```

```
Gly Gly Leu Asn Thr Ile Asp Ile Leu Thr Ala Ile Arg Asn Ala Thr
385                 390                 395                 400

Gly Pro Arg Pro Ala Leu Phe Val Pro Glu Val Ser Phe Glu Leu Leu
                405                 410                 415

Val Lys Arg Gln Ile Lys Arg Leu Glu Glu Pro Ser Leu Arg Cys Val
            420                 425                 430

Glu Leu Val His Glu Glu Met Gln Arg Ile Ile Gln His Cys Ser Asn
        435                 440                 445

Tyr Ser Thr Gln Glu Leu Leu Arg Phe Pro Lys Leu His Asp Ala Ile
    450                 455                 460

Val Glu Val Val Thr Cys Leu Arg Lys Arg Leu Pro Val Thr Asn
465                 470                 475                 480

Glu Met Val His Asn Leu Val Ala Ile Glu Leu Ala Tyr Ile Asn Thr
                485                 490                 495

Lys His Pro Asp Phe Ala Asp Ala Cys Gly Leu Met Asn Asn Asn Ile
                500                 505                 510

Glu Glu Gln Arg Arg Asn Arg Leu Ala Arg Glu Leu Pro Ser Ala Val
            515                 520                 525

Ser Arg Asp Lys Leu Ile Gln Asp Ser Arg Arg Glu Thr Lys Asn Val
530                 535                 540

Ala Ser Gly Gly Gly Val Gly Asp Gly Val Gln Glu Pro Thr Thr
545                 550                 555                 560

Gly Asn Trp Arg Gly Met Leu Lys Thr Ser Lys Ala Glu Glu Leu Leu
                565                 570                 575

Ala Glu Glu Lys Ser Lys Pro Ile Pro Ile Met Pro Ala Ser Pro Gln
            580                 585                 590

Lys Gly His Ala Val Asn Leu Leu Asp Val Pro Val Pro Val Ala Arg
        595                 600                 605

Lys Leu Ser Ala Arg Glu Gln Arg Asp Cys Glu Val Ile Glu Arg Leu
    610                 615                 620

Ile Lys Ser Tyr Phe Leu Ile Val Arg Lys Asn Ile Gln Asp Ser Val
625                 630                 635                 640

Pro Lys Ala Val Met His Phe Leu Val Asn His Val Lys Asp Thr Leu
                645                 650                 655

Gln Ser Glu Leu Val Gly Gln Leu Tyr Lys Ser Ser Leu Leu Asp Asp
                660                 665                 670

Leu Leu Thr Glu Ser Glu Asp Met Ala Gln Arg Arg Lys Glu Ala Ala
            675                 680                 685

Asp Met Leu Lys Ala Leu Gln Gly Ala Ser Gln Ile Ile Ala Glu Ile
        690                 695                 700

Arg Glu Thr His Leu Trp
705                 710

<210> SEQ ID NO 5
<211> LENGTH: 2399
<212> TYPE: DNA
<213> ORGANISM: Homo sapiens

<400> SEQUENCE: 5
ccggcgggca ctgggccccc gtgttttcag agtcatggag gcgctaattc ctgtcataaa      60
caagctccag gacgtcttca acacggtggg cgccgacatc atccagctgc tcaaatcgt     120 cgtagtggga acgcagagca gcggaaagag ctcagtgcta gaaagcctgg tggggaggga     180
cctgcttccc agaggtactg gaattgtcac ccggagacct ctcattctgc aactggtcca     240
tgtttcacaa gaagataaac ggaaaacaac aggagaagaa aatggggtgg aagcagaaga     300
```

```
atgggtaaa tttcttcaca ccaaaaataa gctttacacg gattttgatg aaattcgaca      360
agaaattgaa aatgaaacag aaagaatttc aggaaataat aagggagtaa gccctgaacc      420
aattcatctt aagatttttt cacccaacgt tgtcaatttg acacttgtgg atttgccagg      480
aatgaccaag gtgcctgtag gtgatcaacc taaggatatt gagcttcaaa tcagagagct      540
cattcttcgg ttcatcagta atcctaattc cattatcctc gctgtcactg ctgctaatac      600
agatatggca acatcagagg cacttaaaat ttcaagagag gtagatccag atggtcgcag      660
aaccctagct gtaatcacta aacttgatct catggatgcg ggtactgatg ccatggatgt      720
attgatggga agggttattc cagtcaaact tggaataatt ggagtagtta acaggagcca      780
gctagatatt aacaacaaga agagtgtaac tgattcaatc cgtgatgagt atgcttttct      840
tcaaaagaaa tatccatctc tggccaatag aaatggaaca aagtatcttg ctaggactct      900
aaacaggtta ctgatgcatc acatcagaga ttgtttacca gagttgaaaa caagaataaa      960
tgttctagct gctcagtatc agtctcttct aaatagctac ggtgaacccg tggatgataa     1020
aagtgctact ttactccaac ttattaccaa atttgccaca gaatattgta acactattga     1080
aggaactgca aaatatattg aaacttcgga gctatgcgt ggtgctagaa tttgttatat     1140
tttccatgag acttttgggc gaaccttaga atctgttgat ccacttggtg gccttaacac     1200
tattgacatt ttgactgcca ttagaaatgc tactggtcct cgtcctgctt tatttgtgcc     1260
tgaggtttca tttgagttac tggtgaagcg gcaaatcaaa cgtctagaag agcccagcct     1320
ccgctgtgtg gaactggttc atgaggaaat gcaaaggatc attcagcact gtagcaatta     1380
cagtacacag gaattgttac gatttcctaa acttcatgat gccatagttg aagtggtgac     1440
ttgtcttctt cgtaaaaggt tgcctgttac aaatgaaatg gtccataact tagtggcaat     1500
tgaactggct tatatcaaca caaaacatcc agactttgct gatgcttgtg ggctaatgaa     1560
caataatata gaggaacaaa ggagaaacag gctagccaga gaattacctt cagctgtatc     1620
acgagacaag ttaattcagg acagcagaag agaaactaaa aatgttgcat ctggaggtgg     1680 tgggggttgga gatggtgttc aagaaccaac cacaggcaac tggagaggaa tgctgaaaac     1740
ttcaaaagct gaagagttat tagcagaaga aaaatcaaaa cccattccaa ttatgccagc     1800
cagtccacaa aaaggtcatg ccgtgaacct gctagatgtg ccagttcctg ttgcacgaaa     1860
actatctgct cgggaacagc gagattgtga ggttattgaa cgactcatta aatcatattt     1920
tctcattgtc agaaagaata ttcaagacag tgtgccaaag gcagtaatgc atttttttggt     1980 taatcatgtg aaagacactc ttcagagtga gctagtaggc cagctgtata aatcatcctt     2040
attggatgat cttctgacag aatctgagga catggcacag cgcaggaaag aagcagctga     2100
tatgctaaag gcattacaag gagccagtca aattattgct gaaatccggg agactcatct     2160
ttggtgaaga gaactatgta atactgagac tttgttgact caaaacttgc tagttactgc     2220
ctacctgagt agaatcttat ttatgaactc ctgtgtattg caatggtatg aatctgctca     2280
tgtggagact ggctataaac tgaaaagtgt attccaaatt gcagaacaca tcacacattt     2340
aatccaaata ataaatggct gtttctaaag tttcccagta aaaaaaaaa aaaaaaaa      2399
```

<210> SEQ ID NO 6
<211> LENGTH: 4612
<212> TYPE: DNA
<213> ORGANISM: Homo sapiens

<400> SEQUENCE: 6

```
gcatggcctg ccgggagggg gcaggtagcc ggcgggcccg gtccaatggg tgccggcttc       60
```

```
cgaggagagg gcggaggaga ggaggaagga ggcgaactgt gggccccggc cccattcatt      120
gccgtggccg gcgggcactg ggcccccgtg ttttcagagt catggaggcg ctaattcctg      180
tcataaacaa gctccaggac gtcttcaaca cggtgggcgc cgacatcatc cagctgcctc      240
aaatcgtcgt agtgggaacg cagagcagcg gaaagagctc agtgctagaa agcctggtgg      300
ggagggacct gcttcccaga ggtactggaa ttgtcacccg gagacctctc attctgcaac      360
tggtccatgt ttcacaagaa gataaacgga aaacaacagg agaagaaaat ggggtggaag      420
cagaagaatg gggtaaattt cttcacacca aaaataagct ttacacggat tttgatgaaa      480
ttcgacaaga aattgaaaat gaaacagaaa gaatttcagg aaataataag ggagtaagcc      540
ctgaaccaat tcatcttaag attttttcac ccaacgttgt caatttgaca cttgtggatt      600
tgccaggaat gaccaaggtg cctgtaggtg atcaacctaa ggatattgag cttcaaatca      660
gagagctcat tcttcggttc atcagtaatc ctaattccat tatcctcgct gtcactgctg      720
ctaatacaga tatggcaaca tcagaggcac ttaaaatttc aagagaggta gatccagatg      780
gtcgcagaac cctagctgta atcactaaac ttgatctcat ggatgcgggt actgatgcca      840
tggatgtatt gatgggaagg gttattccag tcaaacttgg aataattgga gtagttaaca      900
ggagccagct agatattaac aacaagaaga gtgtaactga ttcaatccgt gatgagtatg      960
cttttcttca aaagaaatat ccatctctgg ccaatagaaa tggaacaaag tatcttgcta     1020
ggactctaaa caggttactg atgcatcaca tcagagattg tttaccagag ttgaaaacaa     1080
gaataaatgt tctagctgct cagtatcagt ctccttctaaa tagctacggt gaacccgtgg     1140
atgataaaag tgctacttta ctccaactta ttaccaaatt tgccacagaa tattgtaaca     1200
ctattgaagg aactgcaaaa tatattgaaa cttcggagct atgcggtggt gctagaattt     1260
gttatatttt ccatgagact tttgggcgaa ccttagaatc tgttgatcca cttggtggcc     1320
ttaacactat tgacattttg actgccatta gaaatgctac tggtcctcgt cctgctttat     1380
ttgtgcctga ggtttcattt gagttactgg tgaagcggca aatcaaacgt ctagaagagc     1440
ccagcctccg ctgtgtggaa ctggttcatg aggaaatgca aaggatcatt cagcactgta     1500
gcaattacag tacacaggaa ttgttacgat ttcctaaact tcatgatgcc atagttgaag     1560
tggtgacttg tcttcttcgt aaaaggttgc ctgttacaaa tgaaatggtc cataacttag     1620
tggcaattga actggcttat atcaacacaa aacatccaga cttttgctgat gcttgtgggc     1680 taatgaacaa taatatagag gaacaaagga gaaacaggct agccagagaa ttaccttcag     1740
ctgtatcacg agacaagtct tctaaagttc aagtgctttt ggcacctgcc tcccaggagc     1800
cctcccccgc tgcttctgct gaggctgatg caagttaat tcaggacagc agaagagaaa     1860
ctaaaaatgt tgcatctgga ggtggtgggg ttggagatgg tgttcaagaa ccaaccacag     1920
gcaactggag aggaatgctg aaaacttcaa aagctgaaga gttattagca gaagaaaat     1980 caaaacccat tccaattatg ccagccagtc cacaaaaagg tcatgccgtg aacctgctag     2040
atgtgccagt tcctgttgca cgaaaactat ctgctcggga acagcgagat tgtgaggtta     2100
ttgaacgact cattaaatca tattttctca ttgtcagaaa gaatattcaa gacagtgtgc     2160
caaaggcagt aatgcatttt ttggttaatc atgtgaaaga cactcttcag agtgagctag     2220
taggccagct gtataaatca tccttattgg atgatcttct gacagaatct gaggacatgg     2280
cacagcgcag gaaagaagca gctgatatgc taaaggcatt acaaggagcc agtcaaatta     2340
ttgctgaaat ccgggagact catctttggt gaagagaact atgtaatact gagactttgt     2400
tgactcaaaa cttgctagtt actgcctacc tgagtagaat cttatttatg aactcctgtg     2460
```

```
tattgcaatg gtatgaatct gctcatgtgg agactggcta taaactgaaa agtgtattcc    2520
aaattgcaga acacatcaca catttaatcc aaataataaa tggctgtttc taaagtttcc    2580
cagtatatat aaaatacatc aagtctgtct tgtgacagtt tcatctgaac ttaacttaaa    2640
aacaactgtt aatgttctag ttgtgcaaag cagtttgcct gtggataaga tgacctgtgt    2700
aataatcttt gttagtagtc ttaaagctgc tgccatagtc ctccaagaag aaagcaccaa    2760
gacaacattt catatgacta taatgcatgt actatataag ctgatctggc tttgaaagat    2820
gtgagttggc aagttcctca catagagtca ttgtattcca cctgtccttc aatttagttt    2880
tttctgagct tctttgcagc ctttgatgtg tttttaagaa agctgaatgc acaagaggat    2940
ctgtgacact gacatggctg tggtgtgcat actgtgtagt tacatagccc ttccaattct    3000
gggtccattt gcactagcaa attaaaatat gctttgattc atacttaaac ctgaaagcag    3060
gaatgcctac attaattcct acattaaaaa cagccatcta cccttgatta tctagaaaga    3120
cttggtaatg atggtcagtt ccttttagat ttcagaaaat caaatgatga cctaaatttc    3180
ccttaatttg caaatacagt agtaattaag gtacatctct aaagtggagc acttacacca    3240
ggctctaaga ttcactttga ggtggaactt aaaaccagtg tactgtatgt atgcattggt    3300
aatagctact tttgcttcat agcttcatac caacaaaata tatttattag aatagtatga    3360
aagtactgga ggagctgaaa gaaaaacacc caaggctggg cgtggtggca cacgcctgta    3420
atcccagcac tttgggaggc cgaggcaggt ggatcacctg aggttgggag ttggagacca    3480
gcttgaccaa catggagaaa ccccgtctct actaaaaata caaaattggc cgggcgtggt    3540
ggcgcatgcc tgtaatccca gctactcggg agggtgaggc aggagaattg cttgaccctg    3600
ggaggtggag gttgtggtga gctaagatcg tgccattgca ctccagcctt ggcaacaaga    3660
gcgaaactcc gtctcaaaaa aaaaaaataa aacaacaccc agatagatac acatactcct    3720
tcagacttac agacctaagc tgcatttatg gggtagtgat gaggtttaga acatatacat    3780
attttgttaa aattccccag atgattcttg gtatgaacga ctatattata aatttaaga    3840 tgtacttaga aatccttaag acatctagcc ccgtctctaa tagacaacac atttatattg    3900
cagatattac ttttttttca gtttatgacc aggtatttat gaaggactat tggcagggaa    3960
aatatgaata tgttaacttt agcttatggc atcaatttac taaggaacaa caggctcacc    4020
aactgatgtc aaacataaaa accccacat cagtctgata cgatatggta ctactttgaa    4080
tctgttacta gtaccatctt gacagaggat acatgctccc aaaacgtttg ttaccacact    4140
taaaaatcac tgccatcatt aagcatcagt ttcaaaatta tagccattca tgatttactt    4200
tttccagatg actatcatta ttctagtcct ttgaatttgt aagggaaaa aaaacaaaaa    4260 caaaaactta cgatgcactt ttctccagca catcagattt caaattgaaa attaaagaca    4320
tgctatggta atgcacttgc tagtactaca cactttgtac aacaaaaaac agaggcaaga    4380
aacaacggaa agagaaaagc cttcctttgt tggcccttaa actgagtcaa gatctgaaat    4440
gtagagatga tctctgacga tacctgtatg ttcttattgt gtaaataaaa ttgctggtat    4500
gaaatgacac taaagtttgt caaaaaatga attcttaact tttctcccag agaaagggag    4560
acaaaaggag cttttaata cctaatctac tttggaacat aaccgtatag ag            4612
```

<210> SEQ ID NO 7
<211> LENGTH: 4534
<212> TYPE: DNA
<213> ORGANISM: Homo sapiens

<400> SEQUENCE: 7

-continued

```
gcatggcctg ccgggagggg gcaggtagcc ggcgggcccg gtccaatggg tgccggcttc      60
cgaggagagg gcggaggaga ggaggaagga ggcgaactgt gggccccggc cccattcatt     120
gccgtggccg gcgggcactg gggccccgtg ttttcagagt catggaggcg ctaattcctg     180
tcataaacaa gctccaggac gtcttcaaca cggtgggcgc cgacatcatc cagctgcctc     240
aaatcgtcgt agtgggaacg cagagcagcg gaaagagctc agtgctagaa agcctggtgg     300
ggagggacct gcttcccaga ggtactggaa ttgtcacccg gagacctctc attctgcaac     360
tggtccatgt ttcacaagaa gataaacgga aaacaacagg agaagaaaat ggggtggaag     420
cagaagaatg gggtaaattt cttcacacca aaaataagct ttacacggat tttgatgaaa     480
ttcgacaaga aattgaaaat gaaacagaaa gaatttcagg aaataataag ggagtaagcc     540
ctgaaccaat tcatcttaag attttttcac ccaacgttgt caatttgaca cttgtggatt     600
tgccaggaat gaccaaggtg cctgtaggtg atcaacctaa ggatattgag cttcaaatca     660
gagagctcat tcttcggttc atcagtaatc ctaattccat tatcctcgct gtcactgctg     720
ctaatacaga tatggcaaca tcagaggcac ttaaaatttc aagagaggta gatccagatg     780
gtcgcagaac cctagctgta atcactaaac ttgatctcat ggatgcgggt actgatgcca     840
tggatgtatt gatgggaagg gttattccag tcaaacttgg aataattgga gtagttaaca     900
ggagccagct agatattaac aacaagaaga gtgtaactga ttcaatccgt gatgagtatg     960
cttttcttca aagaaatat ccatctctgg ccaatagaaa tggaacaaag tatcttgcta    1020
ggactctaaa caggttactg atgcatcaca tcagagattg tttaccagag ttgaaaacaa    1080
gaataaatgt tctagctgct cagtatcagt ctcttctaaa tagctacggt gaacccgtgg    1140
atgataaaag tgctacttta ctccaactta ttaccaaatt tgccacagaa tattgtaaca    1200
ctattgaagg aactgcaaaa tatattgaaa cttcggagct atgcggtggt gctagaattt    1260
gttatatttt ccatgagact tttgggcgaa ccttagaatc tgttgatcca cttggtggcc    1320
ttaacactat tgacattttg actgccatta gaatgctac tggtcctcgt cctgctttat    1380
ttgtgcctga ggtttcattt gagttactgg tgaagcggca aatcaaacgt ctagaagagc    1440
ccagcctccg ctgtgtggaa ctggttcatg aggaaatgca aaggatcatt cagcactgta    1500
gcaattacag tacacaggaa ttgttacgat ttcctaaact tcatgatgcc atagttgaag    1560
tggtgacttg tcttcttcgt aaaaggttgc ctgttacaaa tgaaatggtc cataacttag    1620
tggcaattga actggcttat atcaacacaa aacatccaga ctttgctgat gcttgtgggc    1680
taatgaacaa taatatagag gaacaaagga gaaacaggct agccagagaa ttaccttcag    1740
ctgtatcacg agacaagtta attcaggaca gcagaagaga aactaaaaat gttgcatctg    1800
gaggtggtgg ggttggagat ggtgttcaag aaccaaccac aggcaactgg agaggaatgc    1860
tgaaaacttc aaaagctgaa gagttattag cagaagaaaa atcaaaaccc attccaatta    1920
tgccagccag tccacaaaaa ggtcatgccg tgaacctgct agatgtgcca gttcctgttg    1980
cacgaaaact atctgctcgg gaacagcgag attgtgaggt tattgaacga ctcattaaat    2040
catatttct cattgtcaga aagaatattc aagacagtgt gccaaaggca gtaatgcatt    2100
ttttggttaa tcatgtgaaa gacactcttc agagtgagct agtaggccag ctgtataaat    2160
catccttatt ggatgatctt ctgacagaat ctgaggacat ggcacagcgc aggaaagaag    2220
cagctgatat gctaaaggca ttacaaggag ccagtcaaat tattgctgaa atccgggaga    2280
ctcatctttg gtgaagagaa ctatgtaata ctgagctttt gttgactcaa aacttgctag    2340
ttactgccta cctgagtaga atcttatttta tgaactcctg tgtattgcaa tggtatgaat    2400
```

-continued

```
ctgctcatgt ggagactggc tataaactga aaagtgtatt ccaaattgca gaacacatca    2460
cacatttaat ccaaataata aatggctgtt tctaaagttt cccagtatat ataaaataca    2520
tcaagtctgt cttgtgacag tttcatctga acttaactta aaaacaactg ttaatgttct    2580
agttgtgcaa agcagtttgc ctgtggataa gatgacctgt gtaataatct ttgttagtag    2640
tcttaaagct gctgccatag tcctccaaga agaaagcacc aagacaacat tcatatgac     2700
tataatgcat gtactatata agctgatctg gctttgaaag atgtgagttg gcaagttcct    2760
cacatagagt cattgtattc cacctgtcct tcaatttagt ttttctgag cttcttgca      2820
gcctttgatg tgtttttaag aaagctgaat gcacaagagg atctgtgaca ctgacatggc    2880
tgtggtgtgc atactgtgta gttacatagc ccttccaatt ctgggtccat ttgcactagc    2940
aaattaaaat atgctttgat tcatacttaa acctgaaagc aggaatgcct acattaattc    3000
ctacattaaa aacagccatc taccttgat tatctagaaa gacttggtaa tgatggtcag    3060
ttccttttag atttcagaaa atcaaatgat gacctaaatt tcccttaatt tgcaaataca    3120
gtagtaatta aggtacatct ctaaagtgga gcacttacac caggctctaa gattcacttt    3180
gaggtggaac ttaaaaccag tgtactgtat gtatgcattg gtaatagcta cttttgcttc    3240
atagcttcat accaacaaaa tatatttatt agaatagtat gaaagtactg gaggagctga    3300
aagaaaaaca cccaaggctg ggcgtggtgg cacacgcctg taatcccagc actttgggag    3360
gccgaggcag gtggatcacc tgaggttggg agttggagac cagcttgacc aacatggaga    3420
aaccccgtct ctactaaaaa tacaaaattg gccgggcgtg gtggcgcatg cctgtaatcc    3480
cagctactcg ggagggtgag gcaggagaat tgcttgaccc tgggaggtgg aggttgtggt    3540
gagctaagat cgtgccattg cactccagcc ttggcaacaa gagcgaaact ccgtctcaaa    3600
aaaaaaaaat aaaacaacac ccagatagat acacatactc cttcagactt acagacctaa    3660
gctgcattta tggggtagtg atgaggttta gaacatatac atattttgtt aaaattcccc    3720
agatgattct tggtatgaac gactatatta taaattttaa gatgtactta gaaatcctta    3780
agacatctag ccccgtctct aatagacaac acatttatat tgcagatatt acttttttt     3840
cagtttatga ccaggtattt atgaaggact attggcaggg aaaatatgaa tatgttaact    3900
ttagcttatg gcatcaattt actaaggaac aacaggctca ccaactgatg tcaaacataa    3960
aaaccccac atcagtctga tacgatatgg tactactttg aatctgttac tagtaccatc     4020
ttgacagagg atacatgctc ccaaaacgtt tgttaccaca cttaaaaatc actgccatca    4080
ttaagcatca gtttcaaaat tatagccatt catgatttac tttttccaga tgactatcat    4140
tattctagtc ctttgaattt gtaagggaa aaaaacaaa aacaaaaact tacgatgcac      4200
ttttctccag cacatcagat ttcaaattga aaattaaaga catgctatgg taatgcactt    4260
gctagtacta cacactttgt acaacaaaaa acagaggcaa gaaacaacgg aaagagaaaa    4320
gccttccttt gttggcccctt aaactgagtc aagatctgaa atgtagagat gatctctgac    4380
gatacctgta tgttcttatt gtgtaaataa aattgctggt atgaaatgac actaaagttt    4440
gtcaaaaaat gaattcttaa cttttctccc agagaaaggg agacaaaagg agcttttaa     4500
tacctaatct actttggaac ataaccgtat agag                                4534
```

<210> SEQ ID NO 8
<211> LENGTH: 4501
<212> TYPE: DNA
<213> ORGANISM: Homo sapiens

<400> SEQUENCE: 8

```
gcatggcctg ccgggagggg gcaggtagcc ggcgggcccg gtccaatggg tgccggcttc      60
cgaggagagg gcggaggaga ggaggaagga ggcgaactgt gggccccggc cccattcatt     120
gccgtggccg gcgggcactg gggccccgtg ttttcagagt catggaggcg ctaattcctg     180
tcataaacaa gctccaggac gtcttcaaca cggtgggcgc cgacatcatc cagctgcctc     240
aaatcgtcgt agtgggaacg cagagcagcg gaaagagctc agtgctagaa agcctggtgg     300
ggagggacct gcttcccaga ggtactggaa ttgtcacccg gagacctctc attctgcaac     360
tggtccatgt ttcacaagaa gataaacgga aacaacagg agaagaaaat ggggtggaag      420
cagaagaatg gggtaaattt cttcacacca aaaataagct ttacacggat tttgatgaaa     480
ttcgacaaga aattgaaaat gaaacagaaa gaatttcagg aaataataag ggagtaagcc     540
ctgaaccaat tcatcttaag attttttcac ccaacgttgt caatttgaca cttgtggatt     600
tgccaggaat gaccaaggtg cctgtaggtg atcaacctaa ggatattgag cttcaaatca     660
gagagctcat tcttcggttc atcagtaatc ctaattccat tatcctcgct gtcactgctg     720
ctaatacaga tatggcaaca tcagaggcac ttaaaatttc aagagaggta gatccagatg     780
gtcgcagaac cctagctgta atcactaaac ttgatctcat ggatgcgggt actgatgcca     840
tggatgtatt gatgggaagg gttattccag tcaaacttgg aataattgga gtagttaaca     900
ggagccagct agatattaac aacaagaaga gtgtaactga ttcaatccgt gatgagtatg     960
cttttcttca aaagaaatat ccatctctgg ccaatagaaa tggaacaaag tatcttgcta    1020
ggactctaaa caggttactg atgcatcaca tcagagattg tttaccagag ttgaaaacaa    1080
gaataaatgt tctagctgct cagtatcagt ctcttctaaa tagctacggt gaacccgtgg    1140
atgataaaag tgctacttta ctccaactta ttaccaaatt tgccacagaa tattgtaaca    1200
ctattgaagg aactgcaaaa tatattgaaa cttcggagct atgcggtggt gctagaattt    1260
gttatatttt ccatgagact tttgggcgaa ccttagaatc tgttgatcca cttggtggcc    1320
ttaacactat tgacattttg actgccatta gaaatgctac tggtcctcgt cctgctttat    1380
ttgtgcctga ggtttcattt gagttactgg tgaagcggca aatcaaacgt ctagaagagc    1440
ccagcctccg ctgtgtggaa ctggttcatg aggaaatgca aaggatcatt cagcactgta    1500
gcaattacag tacacaggaa ttgttacgat ttcctaaact tcatgatgcc atagttgaag    1560
tggtgacttg tcttcttcgt aaaaggttgc ctgttacaaa tgaaatggtc cataacttag    1620
tggcaattga actggcttat atcaacacaa aacatccaga cttttgctgat gcttgtgggc    1680
taatgaacaa taatatagag gaacaaagga gaaacaggct agccagagaa ttaccttcag    1740
ctgtatcacg agacaaggtt gcatctggag gtggtggggt tggagatggt gttcaagaac    1800
caaccacagg caactggaga ggaatgctga aaacttcaaa agctgaagag ttattagcag    1860
aagaaaaatc aaaacccatt ccaattatgc cagccagtcc acaaaaaggt catgccgtga    1920
acctgctaga tgtgccagtt cctgttgcac gaaaactatc tgctcgggaa cagcgagatt    1980
gtgaggttat tgaacgactc attaaatcat attttctcat tgtcagaaag aatattcaag    2040
acagtgtgcc aaaggcagta atgcatttttt tggttaatca tgtgaaagac actcttcaga    2100
gtgagctagt aggccagctg tataaatcat ccttattgga tgatcttctg acagaatctg    2160
aggacatggc acagcgcagg aaagaagcag ctgatatgca aaaggcatta caaggagcca    2220
gtcaaattat tgctgaaatc cgggagactc atctttggtg aagagaacta tgtaatactg    2280
agactttgtt gactcaaaac ttgctagtta ctgcctacct gagtagaatc ttatttatga    2340
actcctgtgt attgcaatgg tatgaatctg ctcatgtgga gactggctat aaactgaaaa    2400
```

```
gtgtattcca aattgcagaa cacatcacac atttaatcca aataataaat ggctgtttct    2460
aaagtttccc agtatatata aaatacatca agtctgtctt gtgacagttt catctgaact    2520
taacttaaaa acaactgtta atgttctagt tgtgcaaagc agtttgcctg tggataagat    2580
gacctgtgta ataatctttg ttagtagtct taaagctgct gccatagtcc tccaagaaga    2640
aagcaccaag acaacatttc atatgactat aatgcatgta ctatataagc tgatctggct    2700
ttgaaagatg tgagttggca agttcctcac atagagtcat tgtattccac ctgtccttca    2760
atttagtttt ttctgagctt ctttgcagcc tttgatgtgt ttttaagaaa gctgaatgca    2820
caagaggatc tgtgacactg acatggctgt ggtgtgcata ctgtgtagtt acatagccct    2880
tccaattctg ggtccatttg cactagcaaa ttaaaatatg ctttgattca tacttaaacc    2940
tgaaagcagg aatgcctaca ttaattccta cattaaaaac agccatctac ccttgattat    3000
ctagaaagac ttggtaatga tggtcagttc cttttagatt tcagaaaatc aaatgatgac    3060
ctaaatttcc cttaatttgc aaatacagta gtaattaagg tacatctcta aagtggagca    3120
cttacaccag gctctaagat tcactttgag gtggaactta aaaccagtgt actgtatgta    3180
tgcattggta atagctactt ttgcttcata gcttcatacc aacaaaatat atttattaga    3240
atagtatgaa agtactggag gagctgaaag aaaaacaccc aaggctgggc gtggtggcac    3300
acgcctgtaa tcccagcact ttgggaggcc gaggcaggtg gatcacctga ggttgggagt    3360
tggagaccag cttgaccaac atggagaaac cccgtctcta ctaaaaatac aaaattggcc    3420
gggcgtggtg gcgcatgcct gtaatcccag ctactcggga gggtgaggca ggagaattgc    3480
ttgaccctgg gaggtggagg ttgtggtgag ctaagatcgt gccattgcac tccagccttg    3540
gcaacaagag cgaaactccg tctcaaaaaa aaaaataaa acaacaccca gatagataca    3600
catactcctt cagacttaca gacctaagct gcatttatgg ggtagtgatg aggtttagaa    3660
catatacata ttttgttaaa attccccaga tgattcttgg tatgaacgac tatattataa    3720
attttaagat gtacttagaa atccttaaga catctagccc cgtctctaat agacaacaca    3780
tttatattgc agatattact ttttttttcag tttatgacca ggtatttatg aaggactatt    3840
ggcagggaaa atatgaatat gttaaacttta gcttatggca tcaatttact aaggaacaac    3900
aggctcacca actgatgtca aacataaaaa cccccacatc agtctgatac gatatggtac    3960
tactttgaat ctgttactag taccatcttg acagaggata catgctccca aaacgtttgt    4020
taccacactt aaaaatcact gccatcatta agcatcagtt tcaaaattat agccattcat    4080
gatttacttt ttccagatga ctatcattat tctagtcctt tgaatttgta aggggaaaaa    4140
aaacaaaaac aaaaacttac gatgcacttt tctccagcac atcagatttc aaattgaaaa    4200
ttaaagacat gctatggtaa tgcacttgct agtactacac actttgtaca acaaaaaaca    4260
gaggcaagaa acaacggaaa gagaaaagcc ttcctttgtt ggcccttaaa ctgagtcaag    4320
atctgaaatg tagagatgat ctctgacgat acctgtatgt tcttattgtg taaataaaat    4380
tgctggtatg aaatgacact aaagtttgtc aaaaaatgaa ttcttaactt ttctcccaga    4440
gaaagggaga caaaggagc ttttaatac ctaatctact ttggaacata accgtataga    4500
g                                                                   4501
```

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic

```
                    siRNA to Drp1 oligonucleotide

<400> SEQUENCE: 9
aacgcagagc agcggaaaga g                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA to ATR oligonucleotide

<400> SEQUENCE: 10
aagagttctc agaagtcaac c                                              21

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      siRNA to Opa1 oligonucleotide

<400> SEQUENCE: 11
aagttatcag tctgagccag gtt                                            23

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA to cyclin E oligonucleotide

<400> SEQUENCE: 12
aaccaaactt gaggaaatct a                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA to ATM oligonucleotide

<400> SEQUENCE: 13
aagcgcctga ttcgagatcc t                                              21
```

INHIBITION OF DYNAMIN RELATED PROTEIN 1 TO PROMOTE CELL DEATH

PRIORITY CLAIM

This application claims priority to U.S. Provisional Application No. 61/476,759, filed Apr. 19, 2011, which is incorporated by reference in its entirety herein.

GRANT INFORMATION

This invention was made with government support under Grant Numbers R01CA148644, P30CA047904, P50CA097190, and P50CA121973 from the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Aug. 1, 2012, is named 72396484.txt and is 47,327 bytes in size.

1. INTRODUCTION

The present invention relates to compositions and methods for reducing cell proliferation and/or promoting cell death by inhibiting dynamin-related protein 1. It further relates to methods of treating cancer which employ an inhibitor of dynamin-related protein 1 alone or together with a second antiproliferative agent.

2. BACKGROUND OF THE INVENTION

Mitochondria are dynamic organelles that consistently undergo fission and fusion events. Deficiencies in the proteins regulating mitochondrial dynamics are associated with a number of human pathologies including neurodegenerative diseases and newborn lethality (Westermann, 2010). Recently, mitochondria have been shown to undergo morphological remodeling as cells progress through the cell cycle (Mitra et al., 2009). At the G1/S boundary mitochondrial tubules form a highly fused network, which is associated with increased mitochondrial ATP production and high levels of cyclin E, in order to promote G1-to-S transition (Mitra et al., 2009). This hyperfused mitochondrial network is then disassembled and becomes increasingly fragmented through S, G2 and M phase of the cell cycle, with the greatest fragmentation evident during mitosis in order to allow the proper partitioning of mitochondria between two daughter cells during cytokinesis (Kashatus et al., 2011). Thus, mitochondrial remodeling throughout the cell cycle is considered to meet the cellular energy demands during the progression of specific stages of the cell cycle, and to ensure faithful inheritance of mitochondria during cell division. However, how deficiencies in the proteins that regulate mitochondrial dynamics impact cell cycle progression and hence directly contribute to the development of diseases is not clear.

The dynamic regulation of mitochondrial morphology is achieved by the coordination of mitochondrial fission and fusion events (Green and Van Houten, 2011). Dynamin-related protein 1 (Drp1), a large dynamin-related GTPase, is essential for mitochondrial fission (Smirnova et al., 2001). Loss of Drp1 results in elongated mitochondria, and Drp1 deficiencies have been identified in several human diseases (Cho et al., 2009; Wang et al., 2008; Waterham et al., 2007). Drp1 is directly regulated by the machinery that controls cell cycle progression. For example, Drp1 is phosphorylated at Ser585 by cdc2/cyclin B in order to promote mitochondrial fission during mitosis (Taguchi et al., 2007). Drp1 deficiency is generally thought to cause mitochondrial dysfunction due to a failure of a Drp1-dependent mechanism of mitophagy that removes damaged mitochondria within the cell (Twig et al., 2008). The resulting accumulation of damaged mitochondria may lead to a depletion of cellular ATP and an inhibition of cell proliferation (Parone et al., 2008). Such an energy depletion-related cell proliferation defect may be caused by a metabolic checkpoint that triggers an AMPK- and p53-dependent G1/S cell cycle arrest (Jones et al., 2005; Owusu-Ansah et al., 2008). Consistent with such a mechanism, overexpression of mutant Drp1 (K38A), results in a hyperfused mitochondrial network and a p53-dependent delay of S phase entry (Mitra et al., 2009). However, reduced cell proliferation has also been observed in the absence of cellular ATP depletion in non-immortalized Drp1-knockout mouse embryonic fibroblasts (MEFs) (Wakabayashi et al., 2009). This suggests that defective mitochondrial dynamics may affect cell proliferation through mechanisms that are not associated with mitochondrial energy metabolism.

Chiang et al. (2009) studied Drp-1 in lung adenocarcinoma, and report a link between Drp 1 and chemotherapy drug resistance that is related to intracellular distribution of Drp 1, where sequestration of Drp 1 to the nucleus (which may be related to hypoxia) is associated with resistance to chemotherapy and poor prognosis.

United States Patent Application Publication Nos. US2005/0038051 and US2008/0287473, both by Nunnari et al., disclose mdivi-1 (referred to as compound A1 and mfisi-1 therein) and related compounds. These applications also disclose that mdivi-1 is a selective inhibitor of Dnm1, the yeast ortholog of Drp1, and inhibits mitochondrial fission and apoptosis. Further, a polypeptide antagonist of calcineurin was reported to inhibit Drp1-dependent mitochondrial fragmentation and apoptosis (Cereghetti and Scorrano, 2010).

3. SUMMARY OF THE INVENTION

The present invention relates to compositions and methods for reducing cell proliferation and/or promoting cell death by inhibiting Drp1. It is based, at least in part, on the discoveries that (i) Drp1 disruption-induced mitochondrial hyperfusion is functionally linked to the cell cycle regulation apparatus, so that Drp1 inhibition results in a disruption of the cell cycle and DNA aberrancies; (ii) inhibition of both Drp1 and ATR are synthetic lethal causing increased DNA damage and apoptotic cell death; and (iii) even in resistant cell lines, Drp1 inhibitor (e.g., mdivi-1) together with a second antiproliferative agent (e.g., cisplatin) act synergistically to promote apoptosis. Accordingly, the present invention provides for novel anticancer strategies.

4. BRIEF DESCRIPTION OF THE FIGURES

FIG. 1A-E. Loss of the fission protein Drp1 causes mitochondrial hyperfusion and induces G2/M cell cycle arrest and aneuploidy. (A) Loss of Drp1 induces G2/M cell cycle arrest and aneuploidy. MDA-MB-231 cells were examined four days after transfection with control or Drp1 siRNA. Cell cycle distribution was determined by flow cytometric analysis of propidium iodide stained cells. The percentage of the cells containing a DNA content of 4N (G2 and M phase cells) and a DNA content>4N (aneuploidy cells) are indicated. These data are representative of three independent experiments. (B) Loss of Drp1 causes mitochondrial hyperfusion. Changes in mitochondrial morphology were visualized in control and Drp1-deficient MDA-MB-231 cells that express pAcGFP1-Mito. Bars: 10 μm (C) Loss of Drp1 causes decreased cell proliferation. Proliferation of control and Drp1-deficient MDA-MB-231 cells was determined using a CyQUANT assay. Data represent mean±SD. n=4 wells. **p<0.01. (D) Loss of the fusion protein Opa1 reverses the phenotypes observed in Drp1-deficient cells. Immunoblots show the knockdown efficiency of Opa1 and Drp1 in MDA-MB-231 cells. Changes in mitochondrial morphology were visualized in Opa1 knockdown and Opa1/Drp1 double knockdown MDA-MB-231 cells that express pAcGFP1-Mito. Bars: 10 μm. Cell cycle distribution was determined as described above. These data are representative of three independent experiments showing at least a two-fold reduction in aneuploidy in the Opa1/Drp1 knockdown cells as compared to Drp1 knockdown cells. (E) Less developed crisae in mitochondria of MDA-MB-231 cells as compared to MCF7 cells, as shown by micrographs from transmission electron microscope. Bars=100 nm.

FIG. 2A-K. The G2/M cell cycle arrest and aneuploidy observed in Drp1-deficient cells are not caused by changes in mitochondrial energy metabolism. (A) Loss of Drp1 does not deplete total intracellular ATP levels. ATP levels were measured after transfection with siRNA for four days (in FIG. 2 all measurements were made four days after transfection). Data represent mean±SD. n=3 wells. *p<0.005. (B) Loss of Drp1 induces slight decrease in mitochondrial membrane potential. Membrane potential was measured after incubating cells with 20 nM of TMRM for 20 min. Cells that were not incubated with TMRM were used as a negative control. Cells treated with 10 μM of FCCP for 20 min were used as a positive control to show depolarized mitochondrial membrane potential. (C, D) Loss of Drp1 impacts oxygen consumption rate (OCR) (C) and extracellular acidification rate (ECAR) (D). OCR and ECAR were measured using a Seahorse Extracellular Flux analyzer. Data represent mean±SD. n=3 wells. *p<0.005. (E, F) Loss of Drp1 suppresses mitochondrial ATP generation. The contribution of mitochondria (E) and contribution of glycolysis (F) to total intracellular ATP levels were determined by measuring the changes in total intracellular ATP levels over time in the presence of 100 mM 2DG and 1 μg/ml of oligomycin, respectively. ATP levels were monitored at 5-min intervals for a total of 30 min. Data represent mean±SD. n=3 wells. *p<0.05. p<0.01. *p<0.005 (G) Loss of Drp1 does not increase mitochondrial superoxide levels. Mitochondrial superoxide levels were measured after incubating cells with 2.5 μM of MitoSox for 20 min. Cells that were not incubated with MitoSox were used as a negative control. Cells treated with 20 μg/ml of antimycin A for 20 min were used as a positive control to show increased mitochondrial superoxide generation. (H) Oxygen consumption is dramatically decreased in MDA-MB-231 $\rho^0$ cells. OCR was measured using a Seahorse Extracellular Flux analyzer. Data represent mean±SD. n=3 wells. ***p<0.005. (I) Loss of Drp1 induces mitochondrial hyperfusion in MDA-MB-231 $\rho^0$ cells. Changes in mitochondrial morphology were visualized by staining control and Drp1-deficient MDA-MB-231 $\rho^0$ cells with 100 nM of MitoTracker green FM for 20 min. Bars: 10 μm (J) Loss of Drp1 induces G2/M cell cycle arrest and aneuploidy in MDA-MB-231 $\rho^0$ cells. Cell cycle distribution was determined by flow cytometric analysis of propidium iodide stained cells. The percentage of the cells containing a DNA content of 4N and a DNA content>4N are indicated. (K) Pharmacological inhibition of mitochondrial respiration, depolarization of mitochondrial membrane potential or stimulation of mitochondrial ROS production does not induce G2/M cell cycle arrest or aneuploidy. MDA-MB-231 cells were treated with either 5 μg/ml oligomycin, 5 μM FCCP, or 10 μg/ml antimycin A for 24 h. Cell cycle distribution was determined as described above.

FIG. 3A-D. The G2/M cell cycle arrest observed in Drp1-deficient cells is not caused by disruptions in the molecular machinery that is essential for the G2/M cell cycle transition. (A) Cartoon indicates the thymidine/nocodazole block protocol used to synchronize siRNA-transfected cells in G2/M phase. (B) Loss of Drp1 prevents cell cycle progression after release from G2/M block. Control and Drp1-deficient cells were released from a thymidine/nocodazole block and cell cycle distribution was determined by flow cytometric analysis of propidium iodide stained cells collected at indicated time points (right). (C) Loss of Drp1 decreases the number of cells in mitosis immediately following a thymidine/nocodazole block. Control and Drp1-deficient cells were synchronized and cells expressing phospho-histone H3 were labeled using Alex Fluor 647-conjugated anti-phospho-histone H3 antibody and detected by flow cytometry. (D) Loss of Drp1 suppresses the factors that are essential for mitotic entry. Control and Drp1-deficient cells were synchronized and collected at indicated time points following release. The changes in the proteins that are associated with mitotic entry were analyzed by western blot. These data are representative of three independent experiments.

FIG. 4A-E. Loss of Drp1 induces chromosomal instability and centrosome overamplification. (A, B) Loss of Drp1 induces chromosome abnormalities in mitosis. (A) Mitotic chromosomes were visualized in control and Drp1-deficient cells stably expressing pAcGFP1-Mito by DAPI staining. Microtubules were visualized by staining cells with Alex Fluor 555-conjugated anti-β-tubulin antibody. Representative metaphase and anaphase images are shown. Arrows indicate lagging chromosomes. Bars: 5 μm. (B) The percentage of mitotic control and Drp1-deficient cells with abnormal chromosomes was determined by counting at least 30 mitotic cells from three independent slides. Data represent mean±SD. *p<0.005. (C, D, E) Loss of Drp1 induces centrosome overamplification. (C) Centrosomes in control and Drp1-deficient cells stably expressing pAcGFP1-Mito were visualized by staining cells with anti-γ-tubulin antibody, followed by secondary Alex Fluor 594 goat anti-mouse antibody. Nuclei were visualized by DAPI staining. Arrows indicate centrosomes. Bars: 10 μm. (D) Enlarged images of a single focal plane from Drp1 knockdown cells "a" and "b" in panel C. (E) The percentage of control and Drp1-deficient cells with more than two centrosomes was determined by counting at least 100 cells from three independent slides. Data represent mean±SD. *p<0.005.

FIG. 5A-D. Loss of Drp1 induces mitochondrial aggregation around the microtubule organizing center (MTOC) (A, B) In Drp1-deficient cells mitochondria aggregate around the MTOC. (A) Microtubules in control and Drp1-deficient cells stably expressing pAcGFP1-Mito were visualized by staining cells with Alex Fluor 555-conjugated anti-β-tubulin antibody, and nuclei were visualized by DAPI staining. Regions with concentrated microtubule staining indicate the locations of MTOC. Bars: 10 μm. (B) Enlarged images of Cell "a" and Cell "b" representing control and Drp1-deficient cells in panel A, respectively. (C) Loss of Drp1 results in reduced mitochondrial motility and redistribution. Mitochondrial dynamics were recorded over time in control and Drp1-deficient MDA-MB-231 cells stably expressing pDsRed2-Mito and histone H2B-GFP. Image sequences show representative mitochondrial movements in the indicated region. Arrows indicate fission events. (D) Mitochondrial remodeling in Drp1-deficient cells. Image sequences obtained in region "a" show a mitochondrial branching event and in region "b" show a transformation of mitochondrial structure from a single fork shape to a net-like morphology.

FIG. 6A-F. The G2/M cell cycle arrest and aneuploidy observed in Drp1-deficient cells are consequences of replication stress-initiated DNA damage signaling that involves ATM/Chk2 and ATR/Chk1 kinases (A) Loss of Drp1 causes accumulation of cyclin E in G2/M phase. Cyclin E expression was assessed by western blot using cell extracts generated from control and Drp1-deficient cells in the presence or absence of nocodazole for 20 h. (B) Knockdown efficiency of cyclin E and Drp1 was confirmed by western blot. (C) Loss of cyclin E reverses the G2/M cell cycle arrest and aneuploidy observed in Drp1-deficient cells. Four days after siRNA transfection, cell cycle distribution was determined by flow cytometric analysis of propidium iodide stained cells. The percentages of the cells containing a DNA content of 4N and >4N are indicated. (D) Loss of Drp1 induces a DNA damage response. Cells were transfected with the indicated siRNA for four days and the changes in the proteins related with DNA damage response were assessed by western blot. (E) Loss of ATM reverses the G2/M cell cycle arrest and aneuploidy observed in Drp1-deficient cells, while loss of ATR induces G2/M cell cycle arrest and aneuploidy. Four days after siRNA transfection, cell cycle distribution was determined as described above. (F) ATR is essential for the survival of Drp1-deficient cells. Cells were transfected with indicated siRNA for four days and apoptosis was assessed by Annexin V and PI staining. The percentages of Annexin V-positive cells are indicated. These data are representative of three independent experiments.

Figure 7:
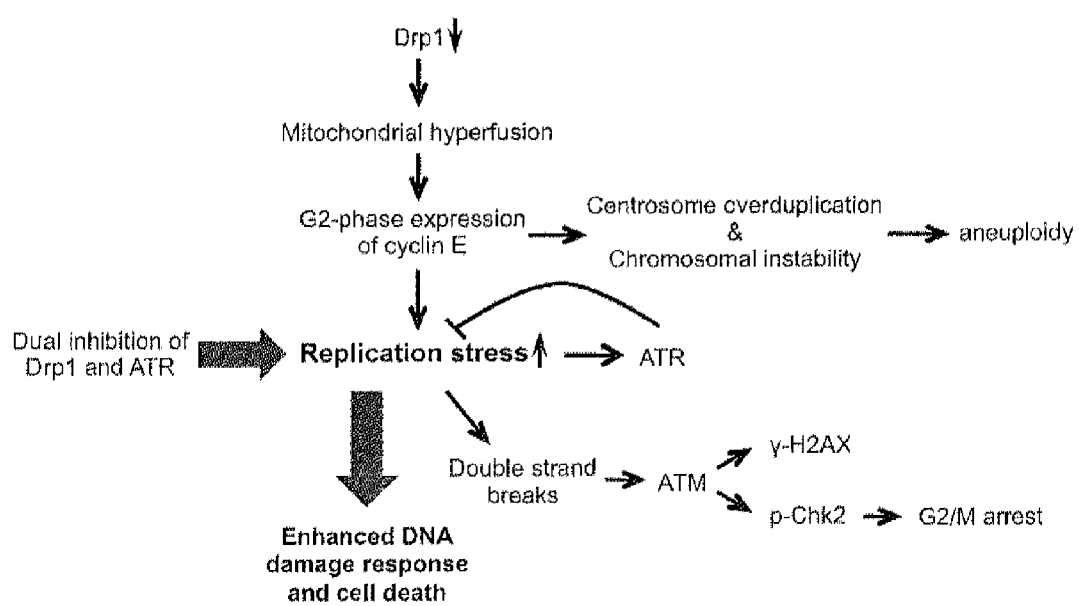

FIG. 7. Loss of Drp1 induces replication stress-mediated genome instability. Our working model shows that mitochondrial hyperfusion induced by loss of fission protein Drp1 leads to replication stress, centrosome overduplication and chromosomal instability, which are mediated, at least in part, by aberrant expression of cyclin E in G2-phase. Persistent replication stress activates an ATM kinase signaling cascade that induces G2/M cell cycle checkpoint. This is consistent with our data that shows that knockdown of either the fusion protein Opa1, cyclin E or ATM reverses the G2/M cell cycle arrest and aneuploidy observed in Drp1-deficient cells. ATR kinase is essential for DNA damage responses to replication stress. Loss of Drp1 induces replication stress and this is further increased by loss of ATR causing increased DNA damage and cell death.

Figure 8A:
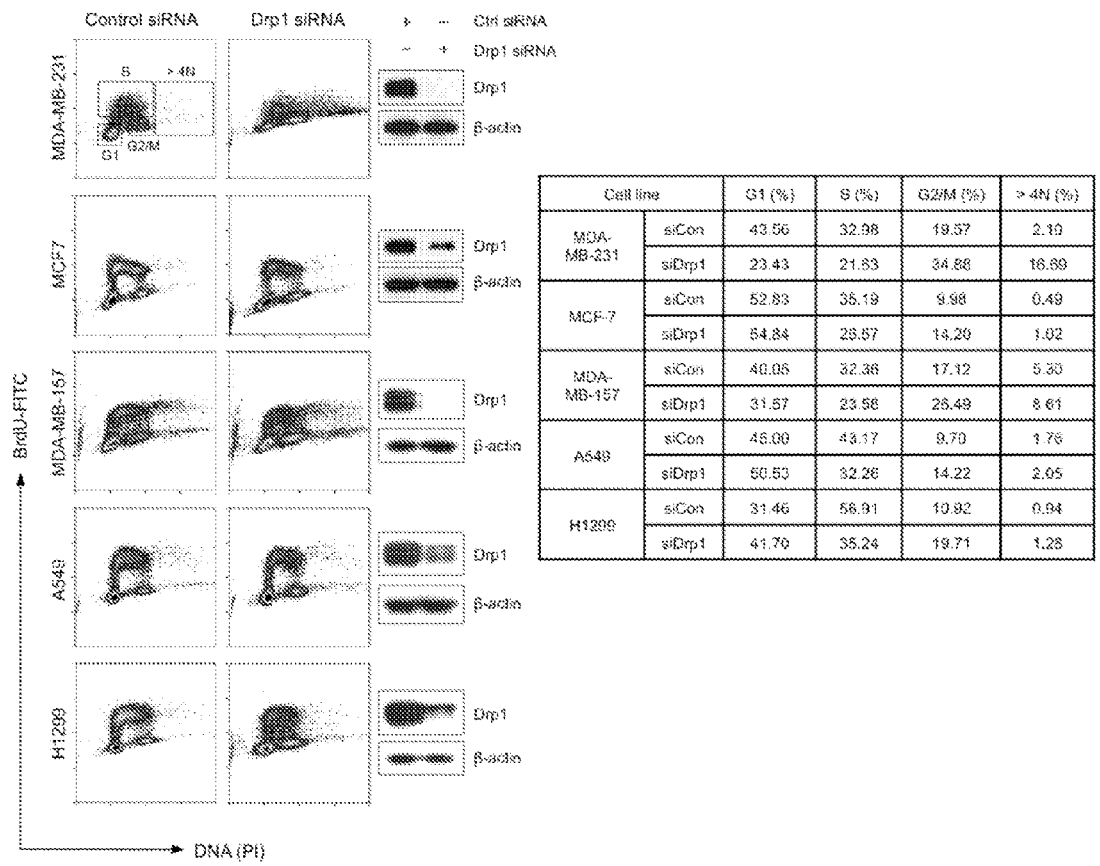
Figure 8B:
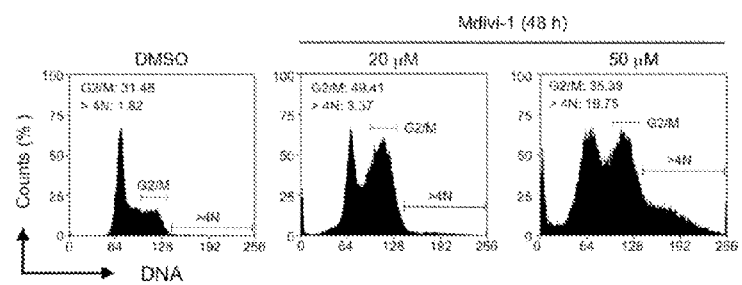

FIG. 8A-B. Both genetic interruption and pharmacological inhibition of Drp1 induce G2/M cell cycle arrest and aneuploidy. (A) siRNA-mediated knockdown of Drp1 induces G2/M cell cycle arrest and aneuploidy in various of cell lines. The human breast carcinoma cell lines MDA-MB-231 (p53R280K), MCF7 (p53 wt) and MDA-MB-157 (p53 null), and the human lung carcinoma cell lines A549 (p53 wt) and H1299 (p53 null) were transfected with control or Drp1 siRNA. Cells were collected at four days after siRNA transfection, and the cell cycle profile was assessed by flow cytometric analysis of BrdU and propidium iodide staining. The percentage of cells in G1, S, G2/M and >4N which were indicated in the square regions were quantified and summarized in the table. (B) Pharmacological inhibition of Drp1 by a small molecule inhibitor mdivi-1 induces G2/M cell cycle arrest and aneuploidy. MDA-MB-231 cells were treated with DMSO as vehicle or mdivi-1 for 48 hours with indicated concentrations. Cell cycle distribution was determined by flow cytometric analysis of propidium iodide stained cells. The percentage of the cells containing a DNA content of 4N and >4N are indicated. Data presented in this figure are representative of three independent experiments.

FIG. 9A-C. Chemical structures of (A) Mdivi-1; (B) cisplatin; and (C) carboplatin.

FIG. 10A-B. (A) The effect of inhibition of Drp1 with siRNA on the cell cycle and DNA content, (B) The effect of inhibition of Drp1 with mdivi-1 on the cell cycle and DNA content.

Figure 11:
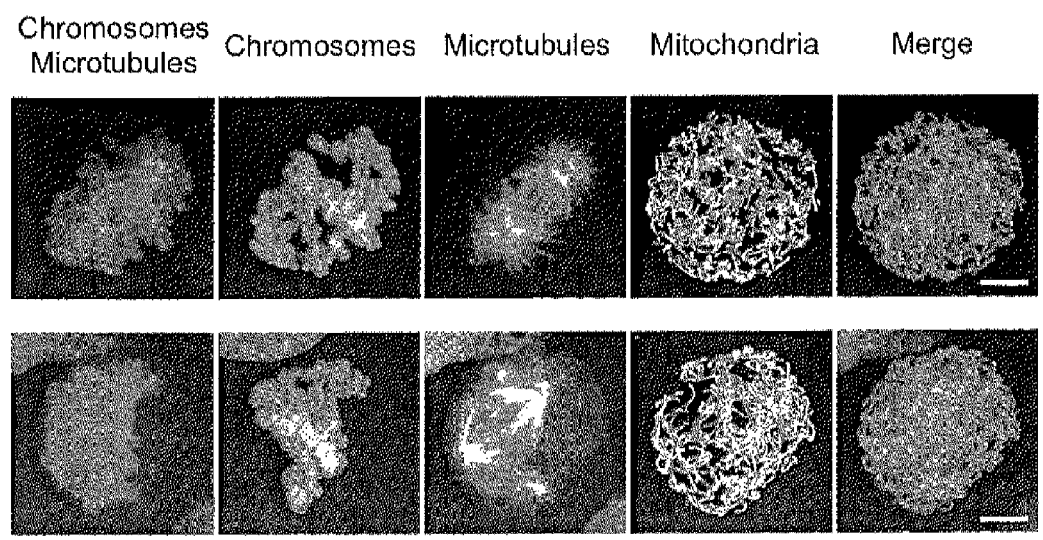

FIG. 11. Mdivi-1-induced chromosomal instability in MDA-MB-231 cells during mitosis. Bars are 5 µm.

Figure 12:
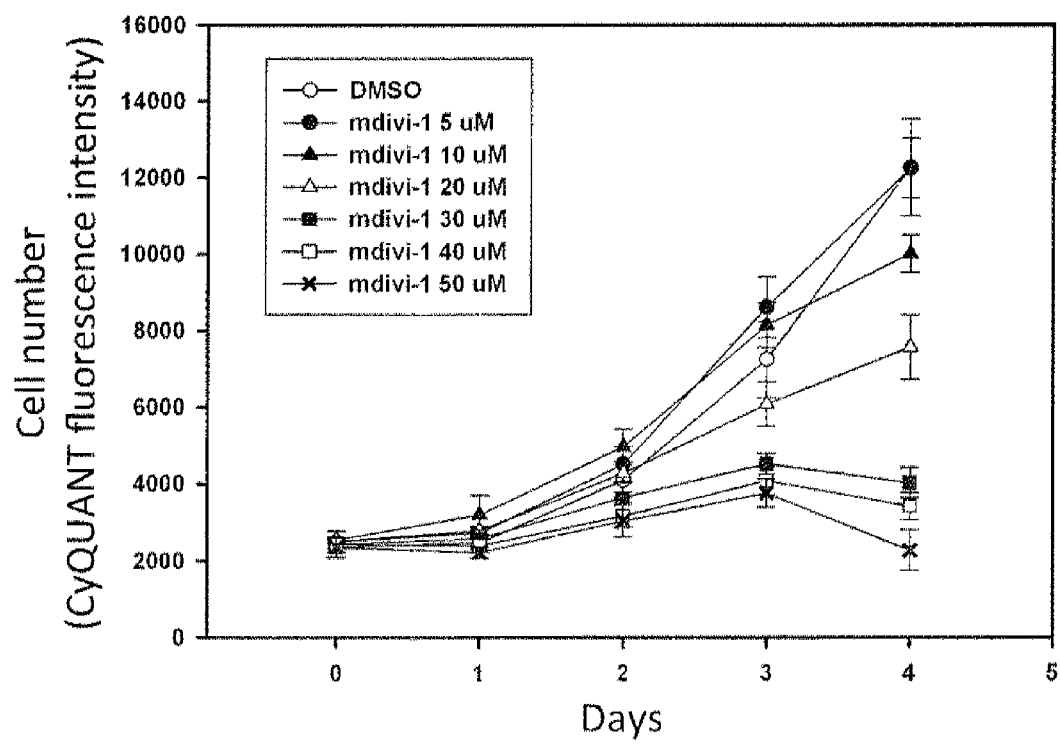

FIG. 12. Growth of MDA-MB-231 breast cancer cells exposed to various concentrations of mdivi-1 or DMSO (as negative control). Data represent mean±SD. n=4 wells.

Figure 13:
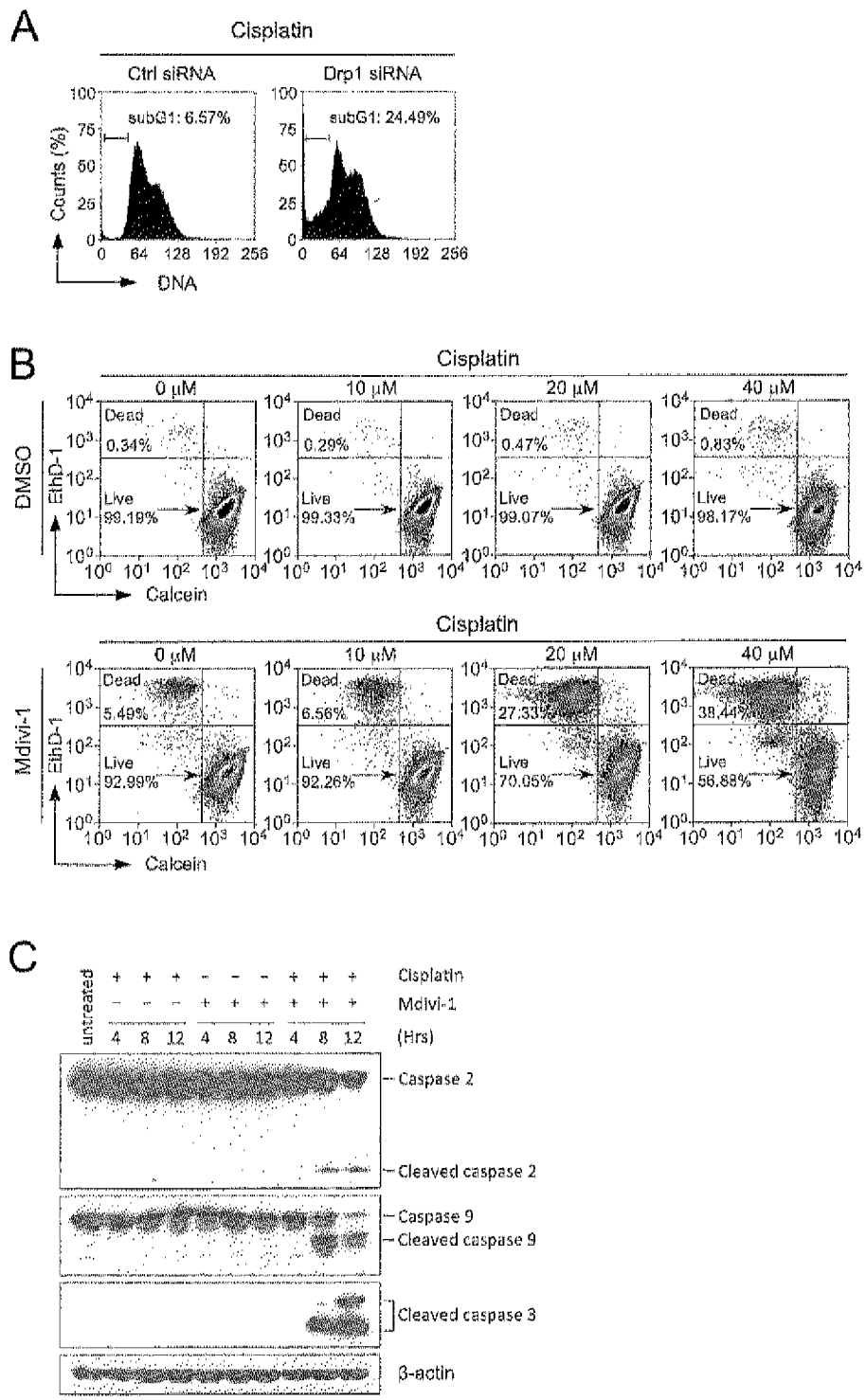

FIG. 13A-C. Inhibiting Drp1 increased cellular sensitivity to cisplatin-induced cell death. (A) Cell viability after treatment with various concentrations of cisplatin decreased when coadministered with Drp1 siRNA. (B) The number of dead cells after treatment with various concentrations of cisplatin increased when coadministered with mdivi-1. (C) The number of apoptotic cells after treatment with various concentrations of cisplatin increased when coadministered with mdivi-1.

Figure 14:
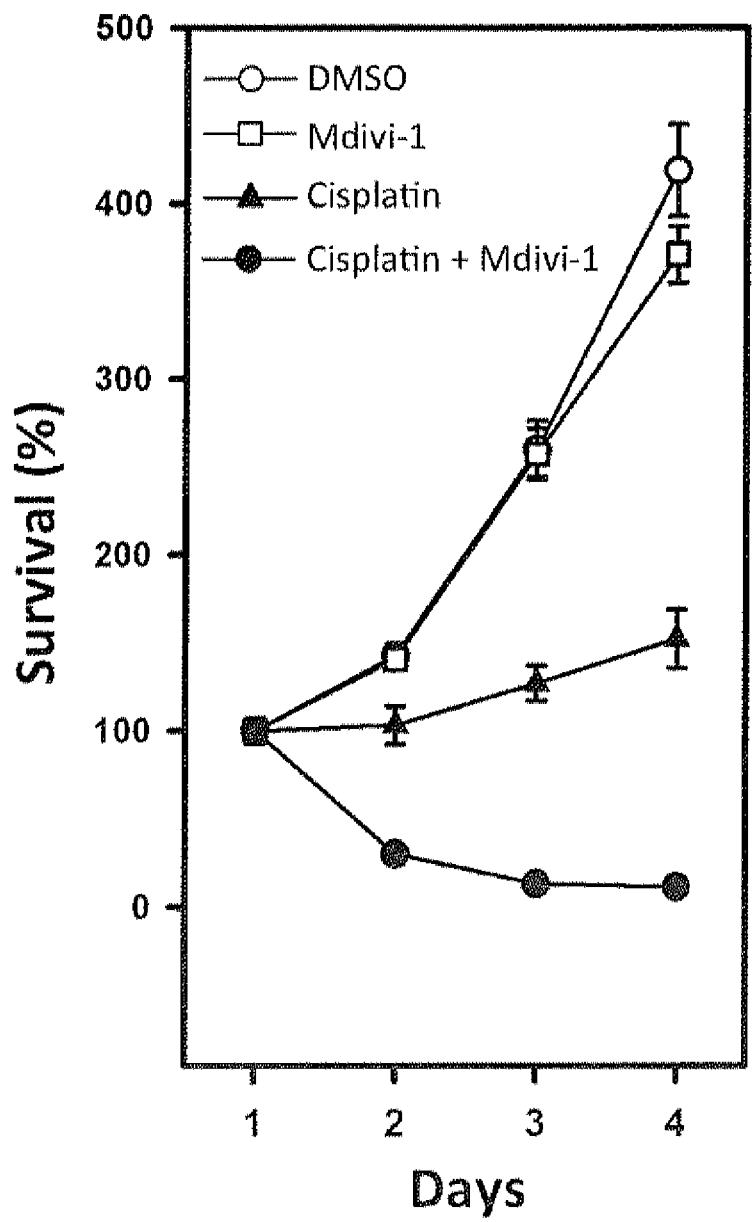

FIG. 14. Survival of MDA-MB-231 breast cancer cells following short-term exposure to mdivi-1 in combination with cisplatin.

Figure 15A:
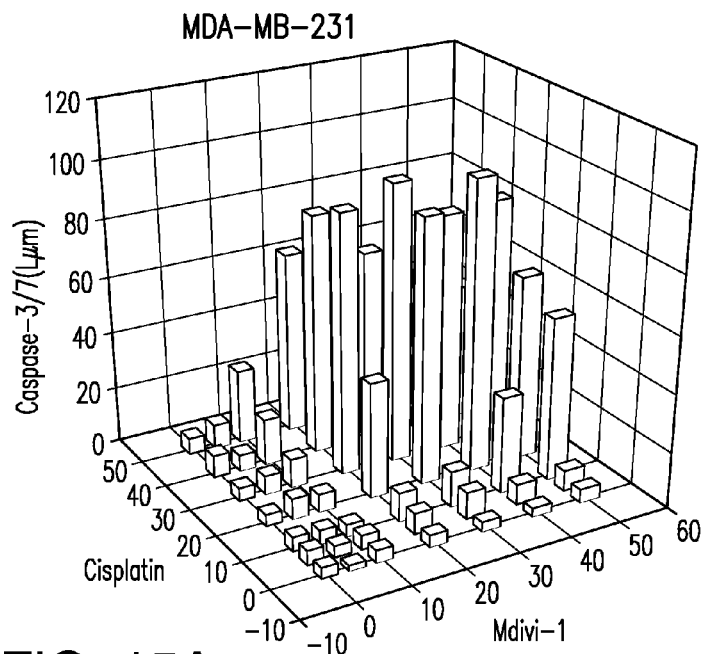
Figure 15B:
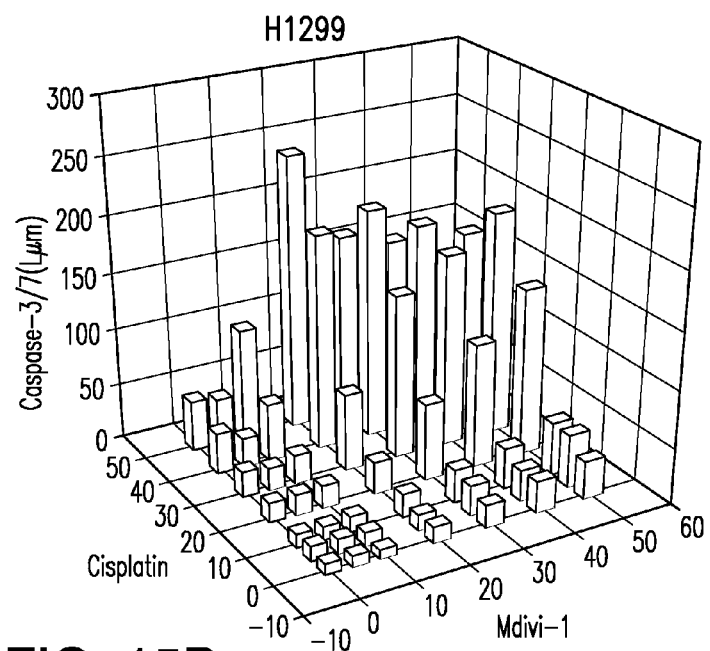
Figure 15C:
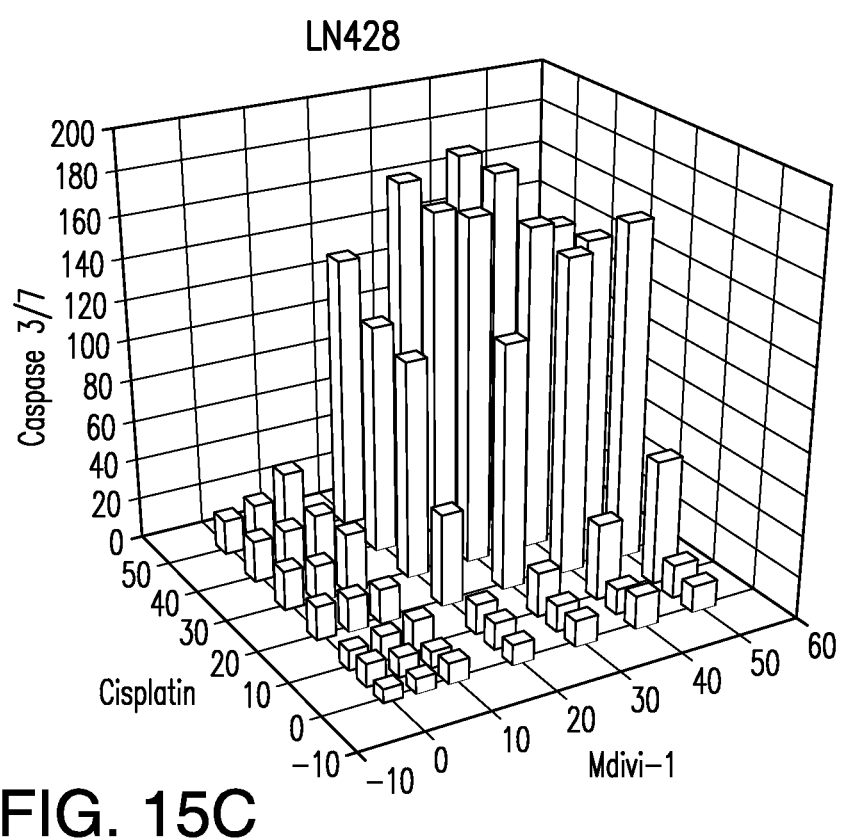

FIG. 15A-C. Survival of (A) MDA-MB-231, (B) non-small cell lung carcinoma cells H1299, and (C) glioblastoma cells LN428 treated with various combinations of cisplatin and mdivi-1.

Figure 16:
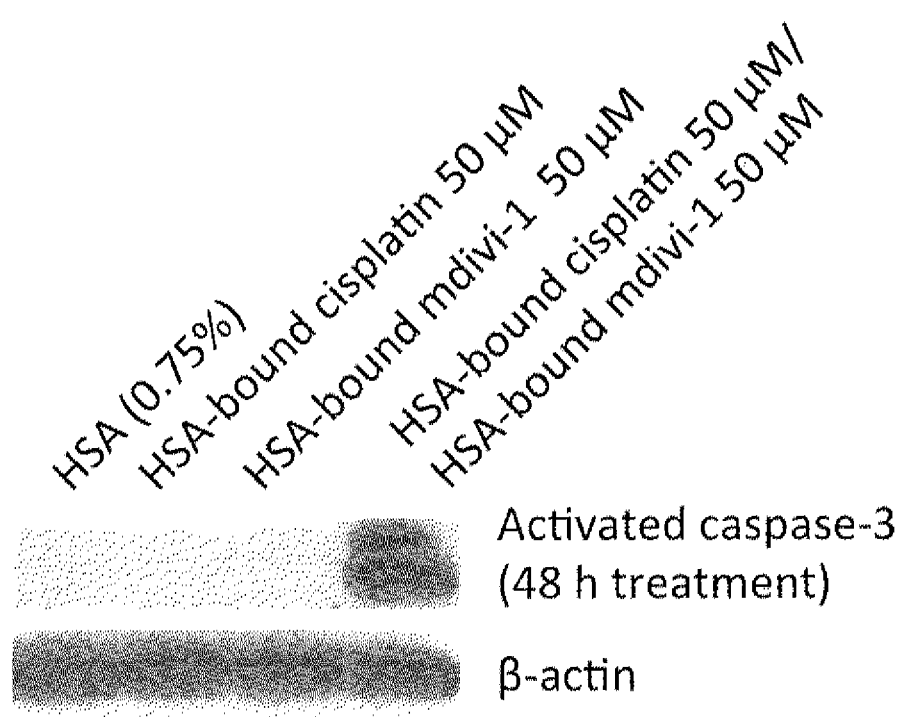

FIG. 16. Human serum albumin (HSA)-bound mdivi-1 enhances the toxicity of HSA-bound cisplatin.

Figure 17:
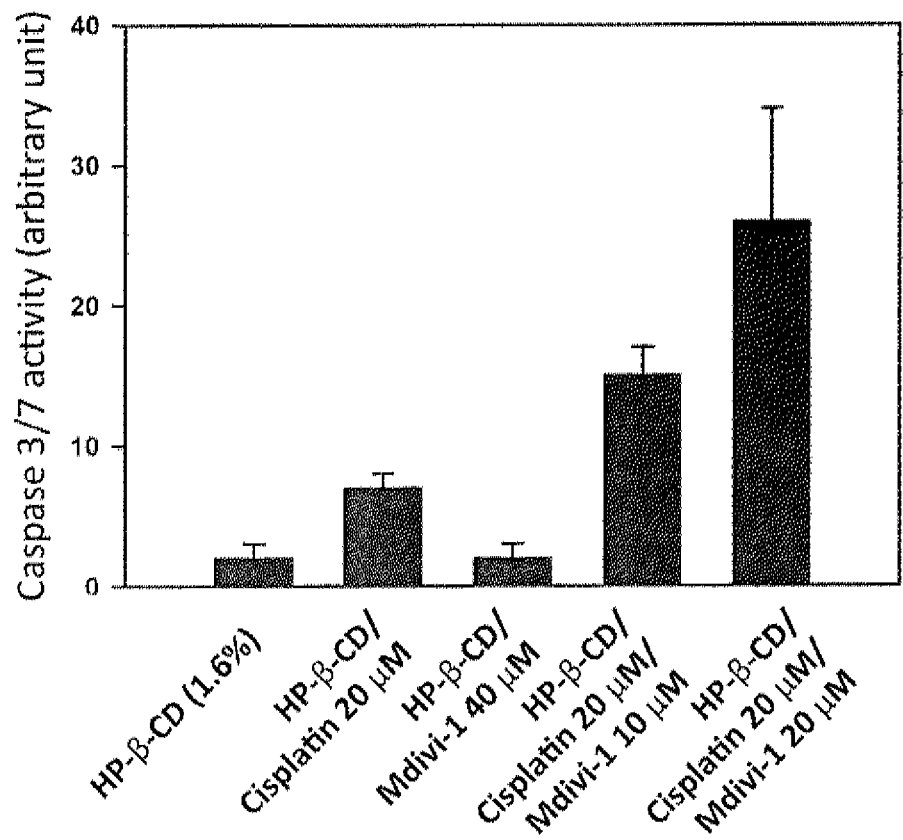

FIG. 17. 2-Hydroxypropyl-β-cyclodextrin (HP-β-CD) can be used to improve the solubility of mdivi-1, and maintain the synergistic cell killing effect with the combination of mdivi-1 and cisplatin.

5. DETAILED DESCRIPTION OF THE INVENTION

For clarity and not by way of limitation, the detailed description is divided into the following subsections:
(i) inhibitors of Drp1;
(ii) formulations of Drp1 inhibitors;
(iii) agents for use with Drp1 inhibitors; and
(iv) methods of treatment.

5.1 Inhibitors of Drp1

In certain non-limiting embodiments, inhibitors of Drp1 that may be used according to the invention include small molecule inhibitors such as the compounds disclosed in United States Patent Application Publication Nos. US2005/0038051 and US2008/0287473, both by Nunnari et al., as inhibitors of the yeast Dynamin-Related GTPase (and Drp1 homology, Dnm1p, including but not limited to the compound depicted herein in FIG. 9A and referred to as mdivi-1. In further non-limiting embodiments, inhibitors of Drp1 include mdivi-1 related compounds described in Cassidy-Stone et al., Dev Cell 14:193-204, for example including compounds B, C, D, E, F, G, H, and I of FIG. 2 of that reference, where compound A (mdivi-1) and compound B are said to have full efficacy relative to mdivi-1 and compounds C, D, and E are said to have moderate efficacy and compounds F, G, H and I are said to have poor efficacy. In specific non-limiting embodiments, a Drp1 inhibitor is mdivi-1 or a mdivi-1 related compound which exhibits at least 50% of the biological activity of mdivi-1 on mitochondrial morphology. In specific, non-limiting embodiments, a Drp1 inhibitor inhibits a Drp1 protein selected from the group consisting of isoform 1 (NCBI Acc. No. NP_036192.2 (SEQ ID NO:1)), isoform 2 (NCBI Acc. No. NP_036193.2 (SEQ ID NO:2)), isoform 3 (NCBI Acc. No. NP_005681.2 (SEQ ID NO:3)) and protein as set forth in GenBank Accession No. AAH24590.1 (SEQ ID NO:4).

In certain non-limiting embodiments, inhibitors of Drp1 that may be used according to the invention include nucleic acids that inhibit expression and/or reduce activity of Drp1, for example but not limited to ribozymes, antisense oligonucleotide inhibitors, and siRNA inhibitors. A "ribozyme" refers to a nucleic acid capable of cleaving a specific nucleic acid sequence. Within some embodiments, a ribozyme should be understood to refer to RNA molecules that contain antisense sequences for specific recognition, and an RNA-cleaving enzymatic activity, see, for example, U.S. Pat. No. 6,770, 633. In contrast, "antisense oligonucleotides" generally are small oligonucleotides complementary to a part of a gene to impact expression of that gene. Gene expression can be inhibited through hybridization of an oligonucleotide to a specific gene or messenger RNA (mRNA) thereof. In some cases, a therapeutic strategy can be applied to dampen expression of one or several genes believed to initiate or to accelerate inflammation, see, for example, U.S. Pat. No. 6,822,087 and WO 2006/062716. A "small interfering RNA" or "short interfering RNA" or "siRNA" or "short hairpin RNA" or "shRNA" are forms of RNA interference (RNAi). An interfering RNA can be a double-stranded RNA or partially double-stranded RNA molecule that is complementary to a target nucleic acid sequence, for example, caspase 6 or caspase 9. Micro interfering RNA's (miRNA) also fall in this category. A double-stranded RNA molecule is formed by the complementary pairing between a first RNA portion and a second RNA portion within the molecule. The length of each portion generally is less than 30 nucleotides in length (e.g., 29, 28, 27, 26, 25, 24, 23, 22, 21, 20, 19, 18, 17, 16, 15, 14, 13, 12, 11, or 10 nucleotides). In some embodiments, the length of each portion is 19 to 25 nucleotides in length. In some siRNA molecules, the complementary first and second portions of the RNA molecule are the "stem" of a hairpin structure. The two portions can be joined by a linking sequence, which can form the "loop" in the hairpin structure. The linking sequence can vary in length. In some embodiments, the linking sequence can be 5, 6, 7, 8, 9, 10, 11, 12 or 13 nucleotides in length. Linking sequences can be used to join the first and second portions, and are known in the art. The first and second portions are complementary but may not be completely symmetrical, as the hairpin structure may contain 3' or 5' overhang nucleotides (e.g., a 1, 2, 3, 4, or 5 nucleotide overhang). The RNA molecules of the invention can be expressed from a vector or produced chemically or synthetically. In certain non-limiting embodiments, the ribozyme, siRNA, or antisense RNA inhibits expression of Drp1 and may comprise a portion which is complementary to a nucleic acid sequence as set forth in one or more of GenBank Accession No. BC024590.1; NCBI Reference Sequence NM_012062.3 (transcript variant 1), NM_012063.2 (transcript variant 2) or NM_005690.3 (transcript variant 3) (see SEQ ID NO:5, 6, 7 and 8, respectively). In one specific, non-limiting embodiment, an siRNA may comprise the sequence 5'-AACGCAGAGCAGCGGAAAGAG-3' (SEQ ID NO:9) (Sugioka et al., 2004).

In certain non-limiting embodiments of the invention, the inhibitor of Drp1 may be Dynasore (Macia et al., 2006). Experiments to date have not demonstrated a synergistic effect between Dynasore and cisplatin.

Additional Drp1 inhibitors may be identified as compounds that have comparable effects on Drp1 activity as Drp1 siRNA and mdivi-1, for example, but not limited to, induction of G2/M cell cycle arrest and aneuploidy (see, for example, FIGS. 10A and B).

5.2 Formulations of Drp1 Inhibitors

In certain non-limiting embodiments, the present invention provides for pharmaceutical formulations for therapeutic use of a Drp1 inhibitor. Such formulations are compositions comprising a Drp1 inhibitor together with one or more of the following: sodium chloride, a pharmaceutical buffer, a carrier, and a solvent. Non-limiting examples of solvents include water, saline, water-miscible alcohols, dimethylsulfoxide, and mixtures thereof. Non-limiting examples of carriers include albumin and cyclodextrin.

In particular, non-limiting embodiments of the invention, the Drp1 inhibitor is a compound disclosed in US2005/0038051 and/or US2008/0287473 and is comprised in a pharmaceutical composition further comprising human serum albumin and/or cyclodextrin 2-Hydroxypropyl-β-cyclodextrin (HP-β-CD). In a specific, non-limiting embodiment, the Drp1 inhibitor is mdivi-1 and is comprised in a pharmaceutical composition further comprising albumin (e.g., human serum albumin ("HSA")) and/or cyclodextrin 2-Hydroxypropyl-β-cyclodextrin (HP-β-CD).

In particular non-limiting embodiments, the molar ratio of Drp1 inhibitor to HSA is between 0.01:1 to 1:1. In a specific non-limiting embodiment, the molar ratio of Drp1 inhibitor to HSA is 1:2.25. In certain non-limiting embodiments, the concentration of HSA is between 0.01% to 30% (weight/volume; w/v). In a subset of such embodiments, the Drp1 inhibitor is mdivi-1.

In particular non-limiting embodiments, the molar ratio of Drp1 inhibitor to cyclodextrin (e.g., HP-β-CD) is between 0.01:1 and 1:1. In particular, non-limiting embodiments, the concentration of HP-β-CD is between 1% to 50% w/v. In a specific, non-limiting embodiment, the concentration of HP-β-CD is between about 35-40% w/v. In a subset of such embodiments, the Drp1 inhibitor is mdivi-1.

5.3 Agents for Use with Drp1 Inhibitors

One or more Drp1 inhibitor may be used in conjunction with treatment with one or more other antiproliferative agent, sometimes referred to herein as a "second antiproliferative agent." Suitable antiproliferative agents include but are not limited to radiation therapy and chemotherapeutic agents. Suitable chemotherapeutic agents include but are not limited to (i) platinum-containing compounds such as cisplatin (FIG. 9B), carboplatin (FIG. 9C), oxiplatin, and bisplatinate compounds; (ii) other alkylating agents including but not limited to carmustine, cyclophosphamide, dacarbazine, ifosfamide, melphalan and thiotepa; and (iii) ATR inhibitors including but not limited to sc-202964, schisandrin B, CGK733, caffeine, and ATR inhibitors set forth in Toledo et al. 2011 and/or Reaper et al., 2011.

5.4 Methods of Treatment

The present invention relates to methods for reducing cell proliferation and/or promoting cell death by inhibiting Drp1.

In certain non-limiting embodiments, the invention provides for a method for reducing cell proliferation and/or promoting cell death by administering, to a cell, an effective amount of a Drp1 inhibitor, optionally in conjunction/combination with administering an effective amount of a second antiproliferative agent. Examples of second antiproliferative agents are provided above. "An effective amount" is an amount that reduces cell proliferation and/or promotes cell death. Where the Drp1 inhibitor is used in conjunction/combination with a second antiproliferative agent, the amount of each may in some instances be less than an effective amount for that agent taken singly, but when both are used effectiveness is achieved.

"In conjunction/combination with," "in conjunction with" or "in combination with" all mean that the Drp1 inhibitor and the second antiproliferative agent are administered to a cell or subject as part of a treatment regimen or plan. These terms do not require that the Drp1 inhibitor and second antiproliferative agent are physically combined prior to administration nor that they be administered over the same time frame. For example, drawing analogy to electronics, they may be administered in series or in parallel.

In certain non-limiting embodiments, the invention provides for a method for reducing cell proliferation and/or promoting cell death in a subject in need of such treatment comprising administering, to the subject, an effective amount of a Drp1 inhibitor, optionally in conjunction with a second antiproliferative agent.

In certain non-limiting embodiments, the present invention provides for a method of treating a disorder associated with cell proliferation comprising administering, to a subject in need of such treatment, an effective amount of a Drp1 inhibitor, optionally in conjunction with a second antiproliferative agent.

A subject is a human or a non-human subject, such as a primate, dog, cat, horse, cow, pig, sheep, goat, etc.

A "subject in need of such treatment" is a subject suffering from a disorder, or at risk of developing a disorder, where the disorder involves unwanted cell proliferation, including but not limited to neoplastic disorders, cancer (solid and non-solid), and disorders of immunity.

In certain non-limiting embodiments, the invention provides for a method for reducing cancer cell proliferation and/or promoting cancer cell death in a subject in need of such treatment comprising administering, to the subject, an effective amount of a Drp1 inhibitor, optionally in conjunction with a second antiproliferative agent.

In certain non-limiting embodiments, the present invention provides for a method of treating a cancer in a subject comprising administering, to the subject, an effective amount of a Drp1 inhibitor, optionally in conjunction with a second antiproliferative agent.

Cancers and cancer cells which may be treated according to the invention include, but are not limited to, breast cancer, lung adenocarcinoma, small cell lung cancer, non-small cell lung cancer, mesothelioma, glioblastoma multiforme, melanoma, hepatocarcinoma, pancreatic carcinoma, gastric carcinoma, biliary carcinoma, intestinal carcinoma, colon carcinoma, renal carcinoma, sarcoma, ovarian carcinoma, testicular carcinoma, prostate cancer, bladder cancer, osteosarcoma, squamous cell carcinoma, squamous cell carcinoma of the head and neck, leukemia, and lymphoma.

In certain non-limiting embodiments, a Drp1 inhibitor is administered by a route selected from the group consisting of intravenous, topical, intramuscular, subcutaneous, oral, intraarterial, intraperitoneal, intrathecal, intranasal, pulmonary, vaginal or rectal. In certain non-limiting embodiments, a Drp1 inhibitor is administered via an implant. In certain non-limiting embodiments, a Drp1 inhibitor is administered by local instillation, for example, at a tumor site or site of tumor resection.

In certain non-limiting embodiments, a secondary antiproliferative agent, where used, is a administered by a route selected from the group consisting of intravenous, intramuscular, subcutaneous, oral, intraarterial, intraperitoneal, intrathecal, intranasal, pulmonary, vaginal or rectal. In certain non-limiting embodiments, a second antiproliferative agent is administered via an implant. In certain non-limiting embodiments, a second antiproliferative agent is administered by local instillation, for example, at a tumor site or site of tumor resection.

In a specific non-limiting embodiment, the Drp1 inhibitor is mdivi-1, and is administered to achieve a local concentration at the site where cell proliferation is to be inhibited of between about 0.001 to 100 µM, or between about 0.1 to 50 µM.

In a specific non-limiting embodiment, the second antiproliferative agent is cisplatin, and is administered to achieve a local concentration at the site where cell proliferation is to be inhibited of between about 0.001 to 100 µM, or between about 0.1 to 50 µM.

In a specific non-limiting embodiment, the second antiproliferative agent is cisplatin, and is administered at a dose of 10-100 mg/m$^2$, administered intravenously.

In a specific non-limiting embodiment, the second antiproliferative agent is carboplatin, and is administered at a dose of 100-400 mg/m$^2$, administered intravenously.

In a specific, non-limiting embodiment, cisplatin or carboplatin is administered with HSA carrier at a molar ratio of cisplatin to HSA of about 1:2.25),

6. MITOCHONDRIAL HYPERFUSION-INDUCED LOSS OF FISSION PROTEIN DRP1 CAUSES ATM-DEPENDENT G2/M ARREST AND ANEUPLOIDY THROUGH DNA REPLICATION STRESS

6.1 Materials and Methods

Cell Culture and Transfection.

The human breast carcinoma cell lines MDA-MB-231, MCF7 and MDA-MB-157, and the human lung carcinoma cell line A549 and H1299 were obtained from American Type Culture Collection (ATCC). Cells were cultured in RPMI 1640 supplemented with 10% heat-inactivated fetal calf serum and 1% penicillin-streptomycin in 5% $CO_2$ at 37° C. MDA-MB-231 $\rho^0$ cell line was established by culturing MDA-MB-231 cells in RPMI 1640 medium supplemented with 10% heat-inactivated fetal calf serum, 1% penicillin-streptomycin, 1 mM sodium pyruvate, 50 µg/ml uridine, and 50 ng/ml ethidium bromide for at least four weeks (King and Attardi, 1996). DNA transfection was performed using FuGENE 6 (Roche) and siRNA transfection was performed using oligofectamine (Invitrogen) according to the manufacture's instructions. Stable cell lines were established by G418 selection and cell sorting following transfection.

Expression Vectors and RNA Interference.

pAcGFP1-Mito and pDsRed2-Mito vectors were purchased from Clontech. Histone H2B-GFP (Kanda et al., 1998) was purchased from Addgene (Addgene plasmid 11680). ATR siRNA was purchased from Dharmacon, while all other siRNAs including AllStars Negative Control siRNA were purchased from Qiagen. The siRNA sense strand sequences are as follows: ATR, 5'-AAGAGTTCTCA- GAAGTCAACC-3' (SEQ ID NO:10); Drp1, 5'-AACGCA-GAGCAGCGGAAAGAG-3' (SEQ ID NO:9) (Sugioka et al., 2004); Opa1, 5'-AAGTTATCAGTCTGAGCCAGGTT-3' (SEQ ID NO:11); cyclin E, 5'-AACCAAACTTGAG-GAAATCTA-3' (SEQ ID NO:12) (Hemerly et al., 2009); ATM, 5'-AAGCGCCTGATTCGAGATCCT-3' (SEQ ID NO:13) (White et al., 2008).

Cell Proliferation.

Cells were transfected with either control or Drp1 siRNA and replated into 96-well plates at the following day. Cell proliferation was determined at 24 h intervals using a CyQUANT Direct Cell Proliferation Assay kit (Invitrogen), according to the manufacturer's instruction.

Apoptosis Detection.

Apoptosis was determined by staining cells with Annexin V-FITC and propidium iodide (PI) using an FITC Annexin V Apoptosis Detection Kit (BD PharMingen, San Diego, Calif.) followed by flow cytometric analysis using a CyAn ADP Analyzer (Beckman Coulter, Brea, Calif.). Data were analyzed using Summit software.

Cell Synchronization.

MDA-MB-231 cells were synchronized at G2/M phase by single thymidine (2 mM) block (19 h) followed by release into nocodazole (100 ng/ml)-containing media (16 h) (thymidine/nocodazole block).

Cell Cycle Analysis.

For DNA content analysis, cells were trypsinized and fixed in 70% ice-cold ethanol overnight at 4° C. After fixation, the cells were washed with 1% BSA/PBS, and permeabilized using 0.25% triton-X 100 in 1% BSA/PBS. Cells were then incubated in PI solution (PBS containing 50 μg/ml of PI and 40 μg/ml of RNase A) for 30 min at room temperature. S phase cells were detected using a bromodeoxyuridine (BrdU) incorporation assay. Cells were pulse-labeled with 10 μM BrdU for 30 min at 37° C. Cells were then trypsinized and fixed in 70% ice-cold ethanol overnight at 4° C. DNA was denatured in 2 N HCl containing 0.5% Triton X-100, and the cells were then neutralized with 0.1 M $Na_2B_4O_7$. Cells were then stained with FITC-labeled anti-BrdU antibody (BD Biosciences, San Jose, Calif.). To determine the number of cells in mitosis, cells were fixed, permeabilized and stained with Alexa Fluor 647-conjugated phospho-Histone H3 (Ser 10) antibody (Cell signaling technology). Samples were then analyzed on a CyAn ADP Analyzer (Beckman Coulter, Brea, Calif.). $5 \times 10^4$ events per sample were acquired to ensure adequate mean fluorescence levels. Data were analyzed using Summit software.

ATP Measurement.

Total cellular ATP content was determined using a luminescent ATP detection kit, ATPlite (PerkinElmer Life Sciences, Boston, Mass.), according to the manufacturer's instructions. The luminescence intensity was measured using a microplate reader, Synergy 2 (BioTek instruments, Winooski, Vt.).

Extracellular Flux (XF) Analysis.

Oxygen consumption rate (OCR) and extracellular acidification rate (ECAR) were measured as we previously described (Qian and Van Houten, 2010). Cells were seeded in XF24 cell culture plates at $4 \times 10^4$ cells/well and incubated in 5% $CO_2$ at 37° C. Prior to the analysis, cells were washed and growth medium was replaced with bicarbonate-free modified RPMI 1640 medium, the "assay medium" (Molecular Devices, Sunnyvale, Calif.). Cells were then incubated for another 60 min in a 37° C. incubator without $CO_2$. OCR and ECAR measurements were then performed simultaneously using a Seahorse XF24 Extracellular Flux Analyzer (Seahorse Bioscience, North Billerica, Mass.).

Mitochondrial Membrane Potential and Superoxide Generation.

To measure mitochondrial membrane potential and superoxide generation, cells were incubated in either 20 nM of TMRM (Invitrogen) or 2.5 μM of MitoSox (Invitrogen) for 20 min at 37° C., respectively. Cells were then trypsinized and suspended in HBSS containing 1% BSA. TMRM and MitoSox fluorescence intensity were analyzed using a CyAn ADP Analyzer (Beckman Coulter, Brea, Calif.). $5 \times 10^4$ events per sample were acquired and the results were analyzed using Summit software.

Western Blot Analysis.

Cells were lysed in cell lysis buffer (Cell signaling technology) containing complete protease inhibitor (Roche). Cell lysates were cleared at 15,000 rpm for 15 min at 4° C. The protein content of the cleared cell lysate was quantified using a Bio-Rad Protein Assay kit (Bio-Rad Laboratories, Hercules, Calif.). Then the cell lysates were combined with 2×SDS sample buffer. The equal amount of protein was separated on Tris-glycine or Tris-acetate gels (Invitrogen). The separated proteins were blotted onto a polyvinylidene difluoride membrane and blocked overnight at 4° C. in phosphate-buffered saline containing 0.1% Tween 20 and 10% nonfat dry milk (blocking buffer). Membranes were incubated with primary antibody in blocking buffer overnight at 4° C. Primary antibodies used were: Drp1 and Opa1 were from BD Biosciences, β-actin (AC-15) and ATM (MAT3-4G10/8) were from Sigma, cyclin E (HE12), cyclin B1 (H-20) and ATR (N-19) were from Santa Cruz Biotechnology, phospho-cdc2 (Tyr15), Chk1 (2G1D5), phospho-Chk2 (Thr68) (C13C1), Chk2 (1C12) and cleaved caspase-3 were from Cell Signaling Technology, phospho-Chk1 (Ser317) was from R&D systems, cdh1 was a gift from Dr. Yong Wan, phospho-ATM (S1981) was from Epitomics, and phospho-Histone H2AX (Ser139) (JBW301) was from Millipore. Membranes were then washed and incubated in peroxidase conjugated anti-rabbit IgG (Sigma), anti-mouse IgG (Sigma), or anti-goat IgG (Santa Cruz Biotechnology) secondary antibody for 1 h at room temperature. Membranes were washed and developed using SuperSignal West Femto Maximum Sensitivity Substrate (Thermo Fisher Scientific).

Immunofluorescence.

Cells were fixed in 4% paraformaldehyde (Electron microscopy sciences, Hatfield, Pa.) in PBS for 15 min at 37° C. and blocked using 3% BSA in PBS containing 0.3% Triton X-100 overnight at 4° C. For centrosome staining, cells were incubated for 1 hour at room temperature with anti-γ-tubulin antibody (Sigma), followed by an incubation with the secondary Alex Fluor 594 goat anti-mouse antibody (Invitrogen) for 1 hour at room temperature. β-tubulin was visualized by incubation with Alex Fluor 555-conjugated anti-β-tubulin antibody (Cell Signaling Technology). Slides were mounted with VECTASHIELD mounting medium containing DAPI (Vector Laboratories, Burlingame, Calif.). Confocal images were captured using a laser-scanning confocal microscope, Olympus FLUOVIEW FV-1000, with a PlanApo N 60× oil immersion objective, NA=1.42 (Olympus).

Live Cell Confocal Microscopy Analysis.

Cells were plated on 40 mm diameter coverglass and incubated for 24 hours at 37° C. The coverglass was then assembled into an environmentally controlled closed chamber system, FCS2 live cell chamber (Bioptechs, Butler, Pa.). The chamber system was then mounted on an inverted confocal microscope (Nikon A1, Nikon), controlled by NIS-Elements software. Leibovitz's L-15 medium supplemented with 10% FBS and 1% penicillin-streptomycin was used, and the temperature of the chamber was maintained at 37° C.

during the imaging. The excitation wavelengths for GFP and DsRed2 were 488 and 543 nm, respectively. Signal was collected through a Plan Apo VC 60× Oil immersion objective, NA=1.40 (Nikon). The number of individual Z-stacks was set to cover the entire thickness of the cell, with the step size of 1 µm. Time-lapse images were captured at the interval of no time delay. The perfect focus system (PFS) was applied to automatically correct possible focus drift during the period of time-lapse imaging. Post-acquisition analysis of image files was performed using MetaMorph (Molecular Devices), Image J (National Institutes of Health) and Photoshop (Adobe).

Statistical Analysis.

Data are expressed as mean±standard deviation. A Student's t test was used for the comparisons between two groups. $p<0.05$ was considered statistically significant.

6.2 Results

Loss of the fission protein Drp1 causes mitochondrial hyperfusion and induces G2/M cell cycle arrest and aneuploidy. To investigate the functional consequences of defective mitochondrial dynamics on cell cycle progression, we knocked down the expression of the mitochondrial fission protein Drp1 using siRNA. Cell cycle analysis revealed that loss of Drp1 induced G2/M cell cycle arrest and aneuploidy (DNA content>4N) in a variety of cell lines independent of their p53 status (FIG. 1A; FIG. 8A). Since MDA-MB-231 cells showed the most severe phenotype, we selected this cell line for further investigations into the underlying mechanism. Mitochondria in MDA-MB-231 cells are thinner and have less cristae than mitochondria in MCF7 cells (FIG. 1E). Drp1 deficiency in MDA-MB-231 cells induced a hyperfused mitochondrial network as expected (FIG. 1B), as well as a remarkable decrease in cell proliferation (FIG. 1C). To confirm that these phenotypes were the consequences of Drp1 deficiency and to exclude the possible off-target effects of the siRNA, we employed a selective small molecule inhibitor of Drp1, mdivi-1 (Cassidy-Stone et al., 2008). Mdivi-1 induced the similar G2/M cell cycle arrest and aneuploidy as Drp1 deficiency achieved by using siRNA (FIG. 8B). Thus, Drp1 function is essential for proper cell cycle progression.

To determine whether mitochondrial fission per se is directly responsible for the G2/M cell cycle arrest and aneuploidy observed in Drp1-deficient cells, we knocked down an essential mitochondrial fusion protein Opa1 (Cipolat et al., 2004) to counteract the Drp1 knockdown-induced mitochondrial hyperfusion. Knockdown of Opa1 restored the mitochondrial fragmentation in Drp1-deficient cells (FIG. 1D). These Drp1 and Opa1 double knockdown cells showed lower G2/M accumulation and a two-fold decrease in aneuploidy as compared to when Drp1 alone was knocked down (compare FIGS. 1D and 1A). These results indicate that the G2/M cell cycle arrest and aneuploidy induced in Drp1-deficient cells required mitochondrial hyperfusion.

The G2/M cell cycle arrest and aneuploidy observed in Drp1-deficient cells are not caused by changes in mitochondrial energy metabolism. Cellular energy status has been recognized as important for cell cycle progression (Mandal et al., 2005). We therefore evaluated if the mitochondrial energy metabolism plays a role in regulating the G2/M cell cycle arrest and aneuploidy in Drp1-deficient MDA-MB-231 cells. Contrary to the previous report using HeLa cells (Parone et al., 2008), there is no depletion of total cellular ATP following Drp1 knockdown (FIG. 2A). Since changes in total intracellular ATP levels may not reflect the changes in mitochondrial metabolism in cancer cells because of the Warburg effect (Warburg et al., 1927), we undertook a detailed analysis to address whether mitochondrial function is altered in Drp1-deficient cells. We observed a slight decrease in mitochondrial membrane potential (FIG. 2B) and about a ~25% decrease in the oxygen consumption rate (OCR) (FIG. 2C), which is accompanied with a concomitant increase in extracellular acidification rate (ECAR) (FIG. 2D), a marker of glycolysis, in Drp1-deficient cells. Consistent with these data, we observed a decreased mitochondrial contribution (indicated by lower ATP levels in the presence of 2-deoxyglucose (2DG)) (FIG. 2E), which is compensated by an increased glycolysis contribution (indicated by higher ATP levels in the presence of oligomycin) (FIG. 2F), in order to maintain total cellular ATP levels in Drp1-deficient cells. These observations indicate that loss of Drp1 in MDA-MB-231 cells reduces mitochondrial energy metabolism. ROS production due to mitochondrial dysfunction is frequently considered a cause of cellular damage and cell cycle arrest (Owusu-Ansah et al., 2008). However, we observed no increase in mitochondrial ROS generation in Drp1-deficient MDA-MB-231 cells using the mitochondrial superoxide indicator MitoSox (FIG. 2G). These results indicate that the G2/M cell cycle arrest and aneuploidy observed in Drp1-deficient cells cannot be attributed to changes in total ATP production or mitochondrially generated ROS.

To further exclude the potential role for mitochondrial energy and ROS in mediating the cell cycle defects observed in Drp1-deficient cells, we examined cell cycle progression in MDA-MB-231 ρ0 cells following knockdown of Drp1. Mitochondria in ρ0 cells do not contribute to total cellular ATP generation and are unable to produce ROS (Weinberg et al., 2010), due to a deficiency in mitochondrial oxidative phosphorylation that is caused by the depletion of mitochondrial DNA (Qian and Van Houten, 2010) (FIG. 2H). Loss of Drp1 in MDA-MB-231 ρ0 cells resulted in elongated mitochondria (FIG. 2I), G2/M cell cycle arrest and aneuploidy (FIG. 2J), that are similar to what we observed in the parental MDA-MB-231 cells (FIG. 1A, B). Furthermore, treatment of MDA-MB-231 cells with either oligomycin, a complex V inhibitor that suppresses mitochondrial respiration, FCCP, an uncoupler that depolarizes mitochondrial membrane potential, or antimycin A, a complex III inhibitor that stimulates mitochondrial ROS production, did not induce G2/M cell cycle arrest and aneuploidy (FIG. 2K). These data further support our conclusion that the G2/M cell cycle arrest and aneuploidy observed in Drp1-deficient cells are not caused by defects in mitochondrial energy metabolism.

Figure 3A:
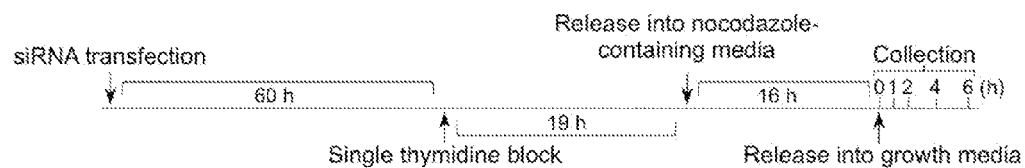
Figure 3B:
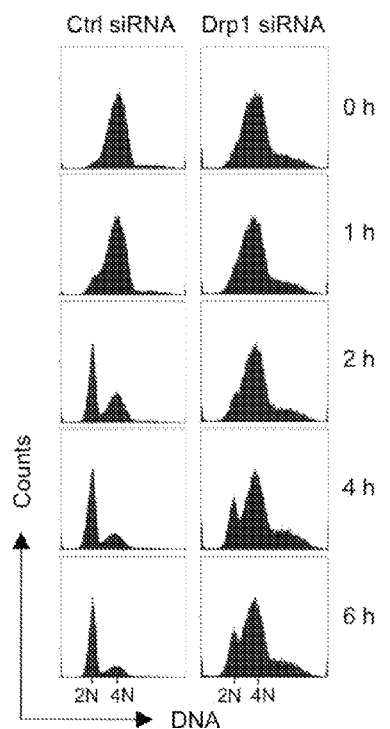
Figure 3C:
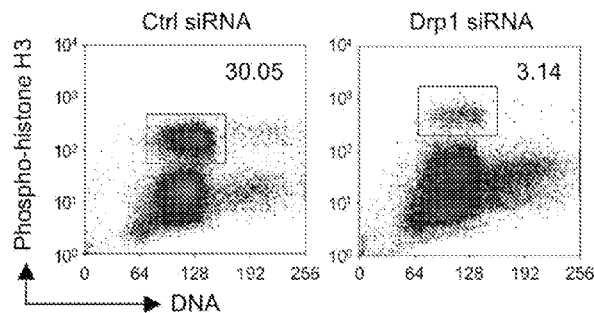

The G2/M cell cycle arrest observed in Drp1-deficient cells is not caused by disruptions in the molecular machinery that is essential for the G2/M cell cycle transition. To investigate the mechanisms underlying the G2/M cell cycle arrest and aneuploidy observed in Drp1-deficient cells, we synchronized MDA-MB-231 cells at G2/M phase using a single thymidine block followed by nocodazole treatment (henceforth referred to as a thymidine/nocodazole block), and then monitored the changes in G2/M phase-related molecular events following the release from G2/M cell cycle block (FIG. 3A). Both control and Drp1-deficient MDA-MB-231 cells were able to be blocked at G2/M phase as shown by their 4N DNA content immediately following the thymidine/nocodazole block (FIG. 3B—0 h release). Phosphorylation of histone H3 at serine residue (Ser10) is associated with chromosome condensation and mitotic entry (Crosio et al., 2002), therefore, the phosphorylation of historic H3 is used as a marker to distinguish M phase cells from G2 phase cells, both of which contain 4N DNA content. Immediately following the thymidine/nocodazole block we observed that the levels of positive phospho-histone H3 in Drp1 knockdown cells was ~10-fold lower than in control cells (FIG. 3C), even though both control and Drp1-deficient cells contained 4N DNA content. These data suggest that the accumulation of 4N DNA content in Drp1-deficient cells was largely due to the cell cycle arrest at G2 phase rather than M phase. Following the release from the G2/M block control cells rapidly entered the cell cycle such that the majority of cells were in G1 phase with 2N DNA content at 6 h (FIG. 3B). In contrast, the majority of Drp1-deficient cells were still at G2/M phase as indicated by the large fraction of cells with 4N DNA content at 6 h following release from the block (FIG. 3B). These data indicated that loss of Drp1 prevented G2 to M cell cycle transition.

Figure 3D:
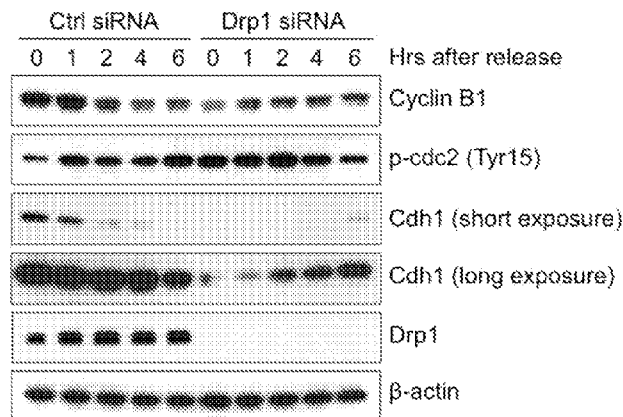

To examine the integrity of molecular events associated with M phase entry, we examined the activity of maturation/mitosis-promoting factor (MPF). MPF is a heterodimeric protein composed of cyclin B and cdc2 serine/threonine kinase (Doree and Hunt, 2002). Both the accumulation of cyclin B1 and dephosphorylation of cdc2 at Tyr15 are required for the initiation of mitosis (Norbury et al., 1991). Drp1-deficient MDA-MB-231 cells were defective in the accumulation of cyclin B1 and the dephosphorylation of cdc2 at Tyr15 in response to thymidine/nocodazole block (FIG. 3D). High levels of phosphorylated cdc2 have previously been associated with effective G2/M cell cycle checkpoint activation (Lew and Kornbluth, 1996). These data indicate that Drp1 deficiency causes suppression of MPF activity and subsequent defect in mitotic entry. Cdh1 is required for the degradation of cyclin B1 and the expression pattern of cdh1 through the cell cycle is similar to that of cyclin B1 (Listovsky et al., 2004). Immediately following the release from the thymidine/nocodazole block control cells showed high levels of cyclin B1 and cdh1, which rapidly declined during the next few hours. This is in stark contrast to the Drp1 knockdown cells, which showed initially low levels of cyclin B1 and very low levels of cdh1 with high levels of phosphorylated cdc2. These Drp1 knockdown cells once released from the thymidine/nocodazole block showed a slow increase in cyclin B1 and cdh1, with a decrease in phosphorylated cdc2 (FIG. 3D). This particular pattern observed in Drp1 knockdown cells represents the slow progression through G2/M phase, which is associated with subsequent aneuploidy. These data are consistent with an induction of a G2/M cell cycle checkpoint in Drp1-deficient cells rather than a disruption in the molecular machinery that is essential for the G2/M cell cycle transition.

Loss of Drp1 induces chromosomal instability and centrosome overamplification. Aneuploidy is frequently a consequence of the chromosomal instability that is associated with defects in mitotic segregation of chromosomes (Rajagopalan and Lengauer, 2004). We observed misaligned chromosomes in metaphase, and lagging chromosomes in anaphase as Drp1-deficient cells progressed through mitosis (FIG. 4A, B). The hyperfused mitochondrial network was maintained throughout the mitosis in Drp1-deficient cells, in contrast to the fragmented mitochondrial morphology observed in control cells (FIG. 4A). These data indicate that defects in mitochondrial fission lead to the defects in chromosome segregation during mitosis. Given that Drp1-deficient cells still retained the ability to progress through mitosis (albeit at a greatly reduced rate) (FIG. 3D), such defects in chromosome segregation could give rise to aneuploidy.

Abnormal extra centrosomes are known to be associated with chromosome instability via formation of aberrant mitotic spindles (Ganem et al., 2009). Depending on the cell cycle phase, normal cells contain one or two centrosomes. We observed that Drp1-deficient cells frequently contained more than two centrosomes relative to control cells (FIGS. 4C, D and E). The Drp1-deficient cells containing extra centrosomes also showed abnormal nuclear morphology and micronuclei (FIG. 4C), a phenotype that is again indicative of chromosome instability. In images obtained from single focal plane we observed that over-amplified centrosomes were often surrounded by aggregated mitochondria, indicating that mitochondrial aggregation is associated with centrosomal abnormalities (FIG. 4D).

Loss of Drp1 induces mitochondrial aggregation around the microtubule organizing center (MTOC). Since the changes in the mitochondrial morphology per se play a direct role in mediating Drp1 deficiency-induced cell cycle defects, as demonstrated by that knockdown of mitochondrial fusion protein Opa1 reversed the G2/M arrest and aneuploidy observed in Drp1-deficient cells, we undertook a detailed analysis of mitochondrial dynamics in Drp1-deficient cells. Microtubules originate at the centrosome (the main microtubule organizing center), and are tracks for mitochondrial transportation and distribution. Since we had observed a centrosome defect in Drp1-deficient cells, we reasoned that the morphological relationship between mitochondria and microtubules might be defective in these cells. In control MDA-MB-231 cells, both the mitochondria and microtubules were observed to be widespread in the cytoplasm, and the area that contained a high concentration of microtubules indirectly marked the location of the MTOC (FIG. 5A, B). In Drp1-deficient cells we observed that mitochondria aggregated around the MTOC, with few elongated mitochondria radiating along microtubule tracks from the mitochondrial aggregates toward the peripheral regions of the cells. We propose that this morphological remodeling results from the retraction and fusion of mitochondria dispersed in peripheral region of the cytoplasm to the MTOC, and this in turn lead to mitochondrial aggregation and a large region of cytoplasm that contains no mitochondria (for example see "cell b" in FIG. 5B). It is also notable that "cell b" shows an abnormal nuclear morphology, and the micronuclei were located inside such mitochondrial aggregates. Therefore the aggregation of mitochondria around the MTOC may affect intracellular homeostasis such as $Ca^{2+}$ signaling that directly contributes to the defects of centrosome duplication and other cell cycle related events (Matsumoto and Mailer, 2002).

Mitochondrial aggregates have been described as clusters of tubules rather than a large mass of coalescing membrane (Smirnova et al., 1998). However, the exact process through which the highly interconnected mitochondrial aggregates are formed is not known. We generated time-lapse movies that revealed markedly reduced mitochondrial motility and redistribution due to lack of fission in Drp1-deficient cells (FIG. 5C and supplementary material Movie 1-4). Nevertheless, mitochondria were still able to undergo some remodeling in these cells, even with the limited frequency and within the limited spatial region. For example, a branching event in Drp1-deficient cells is indicated "a" in FIG. 5D and supplementary material Movie 5. Furthermore, fusion is not limited to end-joining fusion between separate mitochondria, and can occur as a cross-fusion between branched mitochondrial tubules that make contact as shown in region "b" in FIG. 5D and supplementary material Movie 6. In this example, mitochondria underwent a morphological change from a simple fork shape to a complicated net-like structure. These preserved branching and fusion abilities in Drp1-deficient cells eventually build up a complicated mitochondrial network, which appears as mitochondrial aggregates. We believe that these examples are the paradigms that demonstrate how a vast hyperfused mitochondrial network may be generated in the condition of lack of fission.

The G2/M cell cycle arrest and aneuploidy observed in Drp1-deficient cells are consequences of replication stress-initiated DNA damage signaling that involves ATM/Chk2 and ATR/Chk1 kinases. We sought to understand the molecular mechanism that causes the G2/M arrest and aneuploidy in Drp1-deficient cells. Mitochondrial hyperfusion induced either by overexpression of mutant Drp1 (K38A) or by Drp1 inhibitor mdivi-1 has previously been associated with the onset of DNA replication and cyclin E accumulation in HCT116 and NRK cells (Mitra et al., 2009). In contrast, we observed a decrease in cyclin E levels in Drp1-deficient MDA-MB-231 cells relative to control cells (FIG. 6A—lanes 1 and 2). Cyclin E levels accumulate at the G1/S phase boundary, decline during S phase and become low or undetectable when replication is complete (Ekholm et al., 2001). To determine whether this reduction in cyclin E was a reflection of the accumulation of Drp1-deficient cells at G2/M phase, we used nocodazole to arrest both Drp1-deficient and control cells at the G2/M phase. While cyclin E was low in control cells arrested at G2/M with nocodazole, the cyclin E levels were not changed in nocodazole-treated Drp1-deficient cells (FIG. 6A—lanes 3 and 4). Thus, cyclin E is maintained at high levels in G2/M phase in Drp1-deficient cells as compared to that in control cells. These results suggest that the control of cyclin E expression is uncoupled from the cell cycle in Drp1-deficient cells. Overexpression of cyclin E can induce G2/M cell cycle arrest, aneuploidy and genomic instability (Bartkova et al., 2005; Keck et al., 2007; Spruck et al., 1999). To determine whether cyclin E is required for the G2/M cell cycle arrest and aneuploidy observed in Drp1-deficient MDA-MB-231 cells, we disrupted cyclin E using siRNA (FIG. 6B). The concurrent knockdown of cyclin E and Drp1 did not induce a G2/M cell cycle arrest and aneuploidy as compared when Drp1 alone was disrupted (FIG. 6C), suggesting that the cell cycle defects observed in Drp1-deficient cells are cyclin E-dependent.

Dysregulated cyclin E expression and decreased cyclin B/cdc2 kinase activity have been previously associated with DNA damage response and G2/M cell cycle checkpoint activation (Bartkova et al., 2005; Kastan and Bartek, 2004). We therefore examined the activities of ATM, Chk1 and Chk2, three kinases that are integral to the DNA damage response and activation of cell cycle checkpoint. In control and Drp1-deficient MDA-MB-231 cells, we observed that the activities of ATM, Chk1 and Chk2 kinases as indicated by the levels of their phosphorylation were increased in Drp1-deficient cells compared to control cells (FIG. 6D). ATM phosphorylates Chk2 and activates G2/M cell cycle checkpoint through inhibiting cdc2 kinase activity. We observed that ATM knockdown impeded the phosphorylation of Chk2 and abrogated the G2/M cell cycle arrest and aneuploidy in Drp1-deficient cells (FIG. 6D, E), suggesting ATM/Chk2-mediated signaling is required for the cell cycle defects in cells that lack mitochondrial fission.

ATR kinase-dependent phosphorylation and activation of Chk1 are central to the signal transduction axis activated by replication stress (Toledo et al., 2008). The phosphorylation of Chk1 as well as the aberrant expression of cyclin E at G2 phase observed in Drp1-deficient cells suggested that replication stress is induced by the mitochondrial hyperfusion. ATR is essential for the stability of stalled DNA replication forks (Toledo et al., 2008). As such, ATR disruption induces replication stress (Murga et al., 2009) and causes DNA double-strand breaks (DSBs) to be generated at sites of stalled replication forks. We observed increased Chk2 phosphorylation and G2/M cell cycle arrest in ATR-deficient MDA-MB-231 cells, and as such ATR deficiency phenocopies Drp1 deficiency in this replication stress-mediated cell cycle arrest (FIG. 6D, E). In order to test the hypothesis that ATR deficiency would further increase the replication stress in Drp1-deficient cells we knocked down both proteins in MDA-MB-231 cells. Significantly, the knockdown of both Drp1 and ATR dramatically increased the levels of γ-H2AX (a marker of DNA damage), the cleavage of caspase-3 and the number of Annexin V-positive cells that both are associated with apoptosis (FIG. 6D, F). Thus, ATR is essential in preventing the replication stress-associated DNA damage and hence the survival of Drp1-deficient cells.

6.3 Discussion

The replication stress-mediated genome instability and cell cycle defects identified in this study revealed a novel mechanism underlying Drp1 deficiency-related cellular dysfunction. These cell cycle defects were not a result of loss of mitochondrial oxidative phosphorylation and ATP production, but required the hyperfused state of mitochondrial morphology, as Opa1 knockdown was able to abrogate these effects. Thus, we have separated a function for Drp1 in genome stability from its potential role in mitochondrial energy metabolism. We have identified that dysregulation of cyclin E expression in G2 phase is a direct consequence of Drp1 deficiency causing replication stress and a subsequent DNA damage response that is associated with activation of ATM kinase-dependent delay of mitotic entry. Preventing ATR-mediated DNA repair signaling in response to replication stress in Drp1-deficient cells enhances DNA damage and cell death (FIG. 7). Together these data indicate that the cycles of mitochondrial fission and fusion are integrated with the cell cycle apparatus that are essential for genome stability.

Figure 4:
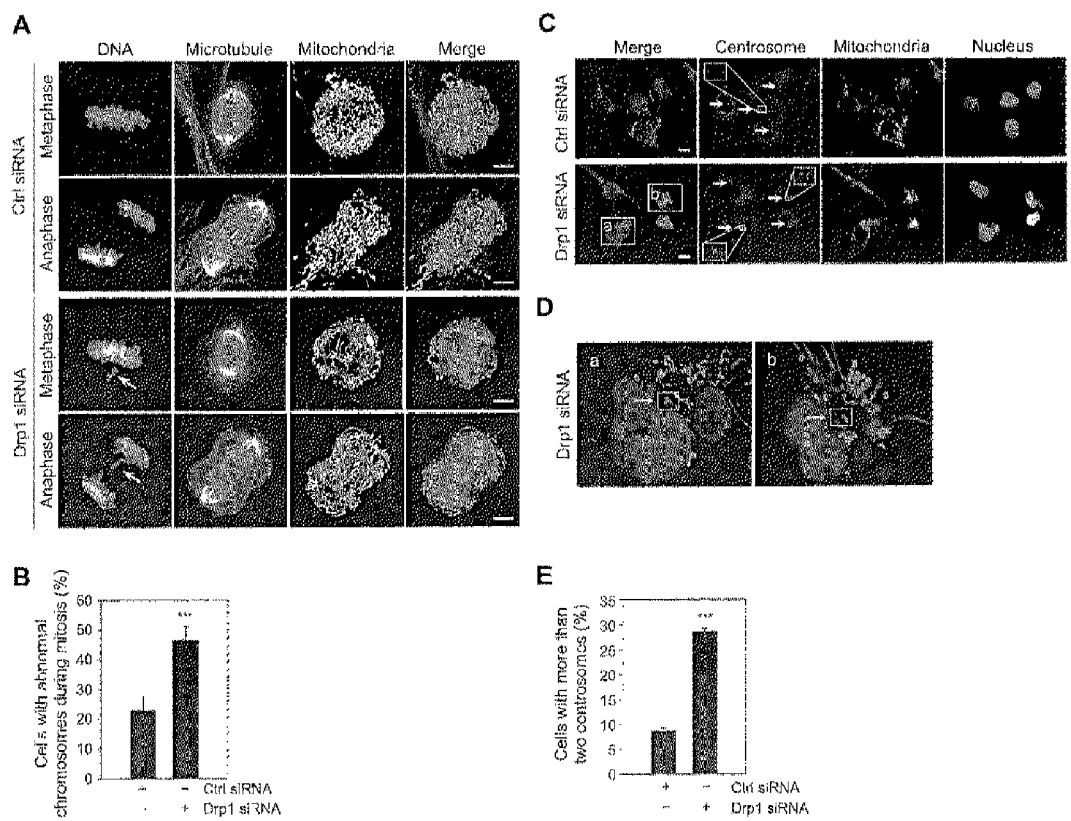

Mitochondria form a highly interconnected network at the G1/S border, and the disassembly of this hyperfused network occurs when the GUS transition process is completed (Mitra et al., 2009). This phenomenon suggests that mitochondrial fission, which is responsible for the disassembly of the hyperfused mitochondrial network, may play a significant role for the progression of following stages of the cell cycle after G1/S transition. In support of this idea, our data revealed that persistent mitochondrial hyperfusion due to loss of fission protein Drp1 is associated with aberrant accumulation of cyclin E in G2 phase when mitochondrial network was not able to be dissembled in this phase following G1/S transition. Cyclin E promotes cell cycle entry into S phase and is related with DNA replication associated functions (Ekholm and Reed, 2000). Cyclin E overexpression impacts DNA replication and leads to replication stress (Toledo et al., 2011). We observed a reduced rate of DNA replication (shown by the decrease of BrdU-positive S-phase cell) in Drp1-deficient cells (supplementary material FIG. S1A), which may reflect either a reduced rate of replication or the activation of a G1/S or intra-S phase cell cycle checkpoint. These data are consistent with previous reports that described a similar reduction in BrdU incorporation (Mitra et al., 2009; Parone et al., 2008). However, the underlying mechanism is not dependent on the depletion of mitochondrial energy as suggested in these reports that activates metabolic checkpoint, as we were not able to phenocopy Drp1 deficiency-induced cell cycle defects by pharmacological inhibition of mitochondrial energy metabolism (FIG. 2K). Rather, the reduction in the number of BrdU-positive S-phase cells in Drp1-deficient cells reflects replication stress that might be caused by either the accumulation of stalled replication forks, inefficient firing of replication origin (Liberal et al., 2011) and/or defects in pre-replication complex (preRC) assembly (Ekholm-Reed et al., 2004), phenotypes that have all been associated with cyclin E overexpression. Such cyclin E-mediated replication stress induces DNA damage and triggers the cell cycle checkpoint in G2 phase (Bartkova et al., 2005). Further, the accumulation of cyclin E is able to induce centrosome overduplication and chromosome instability (Nakayama et al., 2000; Rajagopalan et al., 2004; Spruck et al., 1999). Our results showing an increased number of centrosomes and chromosome instability in Drp1-deficient cells are consistent with these reports (FIG. 4). However, the mechanism underlying Drp1 deficiency-mediated alterations in mitochondrial dynamics and cyclin E dysregulation is unknown.

Our results revealed that as a consequence of replication stress in Drp1-deficient cells, ATR/Chk1 and ATM/Chk2 DNA damage signaling cascades are activated (FIG. 6D). A major cellular defense against DNA damage and control of cell cycle transition and cell death is a signaling network known as the DNA damage response (DDR) that is largely regulated by the ataxia telangiectasia mutated (ATM) and ATM- and Rad3-related (ATR). Cyclin E dysregulation-induced abnormalities in DNA replication are known inducers of the ATR/Chk1 cascade (Kastan and Bartek, 2004). ATR kinase activity is increased by single-stranded DNA (ssDNA). ssDNA accumulates at stalled replication forks that may arise as a consequence of replication stress (Cimprich and Cortez, 2008). Persistent replication stress can lead to the generation of DNA DSBs when stalled replication forks are subject to nucleolytic attack. ATM kinase activity is then increased by DNA DSBs and the subsequent G2/M cell cycle checkpoint is induced. It is noteworthy that knockdown of ATM prevented both G2/M arrest and aneuploidy in Drp1-deficient cells (FIG. 6E), indicating that these cell cycle defects are dependent on ATM-mediated DNA damage signaling. ATM and ATR share many of the numerous substrates that promote cell cycle arrest and DNA repair. However, one of the best established roles of ATR that is not shared by ATM is preventing the collapse of stalled replication forks in generating DSBs (Cimprich and Cortez, 2008). Thus, ATR should attenuate DSBs and subsequent ATM kinase activity under conditions that induce replication stress. Our results showed that ATR kinase inhibition by knockdown of ATR in Drp1-deficient cells enhanced phosphorylation of H2AX and apoptosis. This increase in DNA damage and cell death is considered as the consequence of Drp1 deficiency-related replication stress under the condition of in the absence of ATR. This finding is reminiscent of the increased DNA damage and cell death when cells overexpressing cyclin E were treated with an ATR kinase inhibitor (Toledo et al., 2011). Since ATR activity is restricted to S and G2 phase (Toledo et al., 2011), these data further suggest that the direct impact of Drp1 disruption occurs in these phases. Moreover, centrosome overduplication requires functional G2/M checkpoint (Inanc et al., 2010), and ATM is also involved in initiating the signaling that regulates centrosome reduplication upon DNA damage (Fukasawa, 2007).

Mitochondrial fission is required for inheritance and partitioning of mitochondria during cell division (Westermann, 2010). Inhibiting Drp1-mediated mitochondrial fission has been reported to cause accumulation of mutant mtDNA (Malena et al., 2009). Our results provided the first evidence that mitochondrial dynamics are involved in initiating mitochondria-to-nucleus retrograde signaling, in order to ensure proper mitochondrial inheritance by enforcing cell cycle delay upon detection of abnormal mitochondrial morphology. One of the important roles of mitochondrial hyperfusion at G1/S border is postulated to allow homogenization of mitochondrial matrix and mtDNA. After G1/S transition is completed, mitochondrial fission has to take place during S G2 and M phase to ensure daughter cells inherit even and healthy mitochondria. When mitochondrial fission is impaired, the activation of G2/M cell cycle checkpoint thus allows more time for cells to fragment their mitochondria in preventing unequal segregation of mitochondria and mtDNA.

From a broader perspective, the genomic instability that we have identified in this study as a result of Drp1 deficiency may help explain why disruption of Drp1 induces lethality (Ishihara et al., 2009; Labrousse et al., 1999; Waterham et al., 2007) and cellular senescence (Yoon et al., 2006). Since replication stress has been observed in human precancerous lesions (Gorgoulis et al., 2005), alterations in mitochondrial dynamics may also play a significant role in cancer etiology. Finally, our data support a novel anti-cancer strategy wherein concurrent targeting of the mitochondrial dynamics protein and the DNA repair machinery involved in the repair of replication stress-induced DNA damage might provide more efficient cancer cell killing.

7. EXAMPLE

Anti-Tumor Activity of Mdivi-1, Alone and in Combination with Cisplatin

The effect of Drp1 inhibition on the cell cycle was tested. Cells were transfected with control or Drp1 siRNA for 72 and 96 hours, and then were stained with PI and their DNA contents measured by flow cytometry. The percentage of cells in G2/M stage and the percentage of cells containing DNA content>4N (which indicates aneuploidy) were quantified. Analogous studies were performed using, instead of siRNA, the Drp1 inhibitor, mdivi-1, at a concentration of 50 μM for 24 and 48 hours. The results of siRNA and mdivi-1 inhibition, respectively, are shown in FIGS. 10A and 10B, which show that inhibition of Drp1 by these agents induces G2/M cell cycle arrest and aneuploidy.

The effect of Drp1 inhibition of chromosome stability was then evaluated. MDA-MB-231 cells that have been engineered to stably express a mitochondrial marker protein pAcGFP-1-mito were treated with mdivi-1 for 7 hours. Mitotic cells were selected for examining the morphology of their chromosomes and mitotic spindles. Chromosomes were visualized by DAPI, and mitotic spindles were visualized by staining cells with Alex-Fluor 555-conjugated anti-β tubulin antibody. The results are shown in FIG. 11; two representative mitotic figures are shown.

To test the effect of Drp1 inhibition on tumor cells, MDA-MB-231 cells were plated in black 96-well plates and treated with various concentrations of mdivi-1. Cell numbers were measured by CyQUANT assay every day. As shown if FIG. 12, continuous exposure to mdivi-1 alone inhibited the growth of MDA-MB-231 breast cancer cells in a dose-dependent manner.

To test the effect of Drp-1 inhibition on the effectiveness of cisplatin, in a first series of experiments, MDA-MB-231 cells were transfected with control or Drp1 siRNA, and 48 hours later were then treated with 40 μM of cisplatin for a 24 hour period. The effect of different concentrations of cisplatin on the Drp1 knockdown cells is shown in FIG. 13A, where the subG1 portion in the cell cycle profile indicates cytotoxicity. In a second series of experiments, a LIVE/DEAD Viability/Cytotoxicity kit (Invitrogen) was used to evaluate the effect of inhibition of Drp1 by mdivi-1 on cisplatin cytotoxicity. In this test, the percentage of lice and dead cells are determined simultaneously with two probes, calcein AM and ethidium homodimer (EthD-1). The nonfluorescent cell-permeant calcein AM is converted to the intensely green fluorescent calcein by ubiquitous intracellular esterase only present in live cells. EthD-1 is excluded by the intact plasma membrane of live cells but is able to enter cells with damaged membranes and undergo a 40-fold enhancement of red fluorescence upon binding to nucleic acids. MDA-MB-231 cells were treated with various concentrations of cisplatin in the presence of DMSO or 50 mdivi-1 for 12 hours. Cells were then trypsinized and suspended in HBSS containing 1% BSA. Calcein AM and EthD-1 were added to the cell suspension at final concentrations of 0.1 µM and 8 µM, respectively, Fluorescence intensity was analyzed on a CyAn ADP Analyzer (Beckman Coulter, Brea, Calif.) and the results were analyzed using Summit software. The live-cell population that was positively stained with calcein was detected in the bottom right region and indicated with an arrow. The dead cell population that is positively stained with EthD-1 was detected in the upper left region. The results are shown in FIG. 13B. In a third set of experiments, MDA-MB-231 cells were treated with 40 µM of cisplatin alone, 50 µM of mdivi-1 alone, or a combination of 40 µM of cisplatin and 50 µM of mdivi-1 for various time points. The activation of caspase-2, caspase-9 and caspase-3 were then detected by Western Blot. The results are shown in FIG. 13C.

To explore this effect further, MDA-MB-231 cells were treated with DMSO as a vehicle control, 50 µM of cisplatin, 50 µM of mdivi-1, or 50 µM of cisplatin plus 50 µM of mdivi-1 for 2 hours. The cells were then washed with growth media and plated in black 96-well plates. Survivals were measured by CyQUANT assay. Data represent mean±SD, n=4 wells. The results, as shown in FIG. 14, show that short time exposure (2 h) to mdivi-1 in combination with cisplatin had a synergistic effect in decreasing the survival of MDA-MB-231 breast cancer cells. The action of mdivi-1 alone in such exposure condition was found to be reversible.

To evaluate whether the synergistic effects of Drp1 inhibition and cisplatin could be extended to other types of cancer cells, breast cancer cells MDA-MB-231, non-small cell lung carcinoma cells H1299, and glioblastoma cells LN428 were treated with various combinations of cisplatin and mdivi-1 at indicated concentrations. After continuous exposure for 20 hours, cell death was determined by measuring the activity of caspase 3/7. The luminescence value that indicates the activity of caspase 3/7 for each combination was plotted on a 3D bar chart using SigmaPlot. As shown in FIG. 15A-C, synergistic cell killing was observed between mdivi-1 and cisplatin in various types of cancer cells. Single compound exposure was found to have minimal effect in inducing cell death in these cells.

8. EXAMPLE

Mdivi-1 Solubility is Enhanced by Carrier Compounds

Experiments were performed to test the effect of the carrier compounds HSA and cyclodextrin on the solubility of mdivi-1.

In a first set of experiments, Mdivi-1 dissolved in DMSO was used as stock solution. HSA-bound mdivi-1 was prepared by diluting 50 mM stocks in DMSO with 15% HSA in 0.85% sodium chloride (Sigma) such that the final concentration of mdivi-1 is 1 mM and the final molar ratio of mdivi-1 to HSA is 1:2.25. HSA-bound cisplatin was prepared by combining equal volume of 2 mM cisplatin in 0.85% sodium chloride with 30% HSA in 0.85% sodium chloride (molar ratio of cisplatin to HSA is 1:2.25), and followed by incubation in the dark at 37 degree for overnight (16-20 h). MDA-MB-231 cells were treated with HSA-bound mdivi-1 and/or HSA-bound cisplatin continuously for 48 h, and cell death was determined by western blot using antibody against activated caspase-3.

The results of these experiments indicate that human serum albumin can be used as an effective vehicle to improve the solubility of mdivi-1 for intravenous injection purpose, and also enhances the tumor specificity of mdivi-1. As shown in FIG. 16, human serum albumin (HSA)-bound mdivi-1 enhanced the toxicity of HSA-bound cisplatin. Enhanced solubility of mdivi-1 by HSA is possibly mediated through the hydrophobic binding activity of HSA. HSA is also taken up by tumor cells at increased levels in comparison to normal cells, therefore, binding of mdivi-1 with HSA is expected to enhance the tumor-specific targeting. In addition, albumin is a major serum protein that cisplatin binds after intravenous infusion, however albumin-bound cisplatin is not as effective as free cisplatin. We have found that HSA-bound mdivi-1 is not only able to enhance the activity of free cisplatin, it also enhances the activity of HSA-bound cisplatin.

Figure 5:
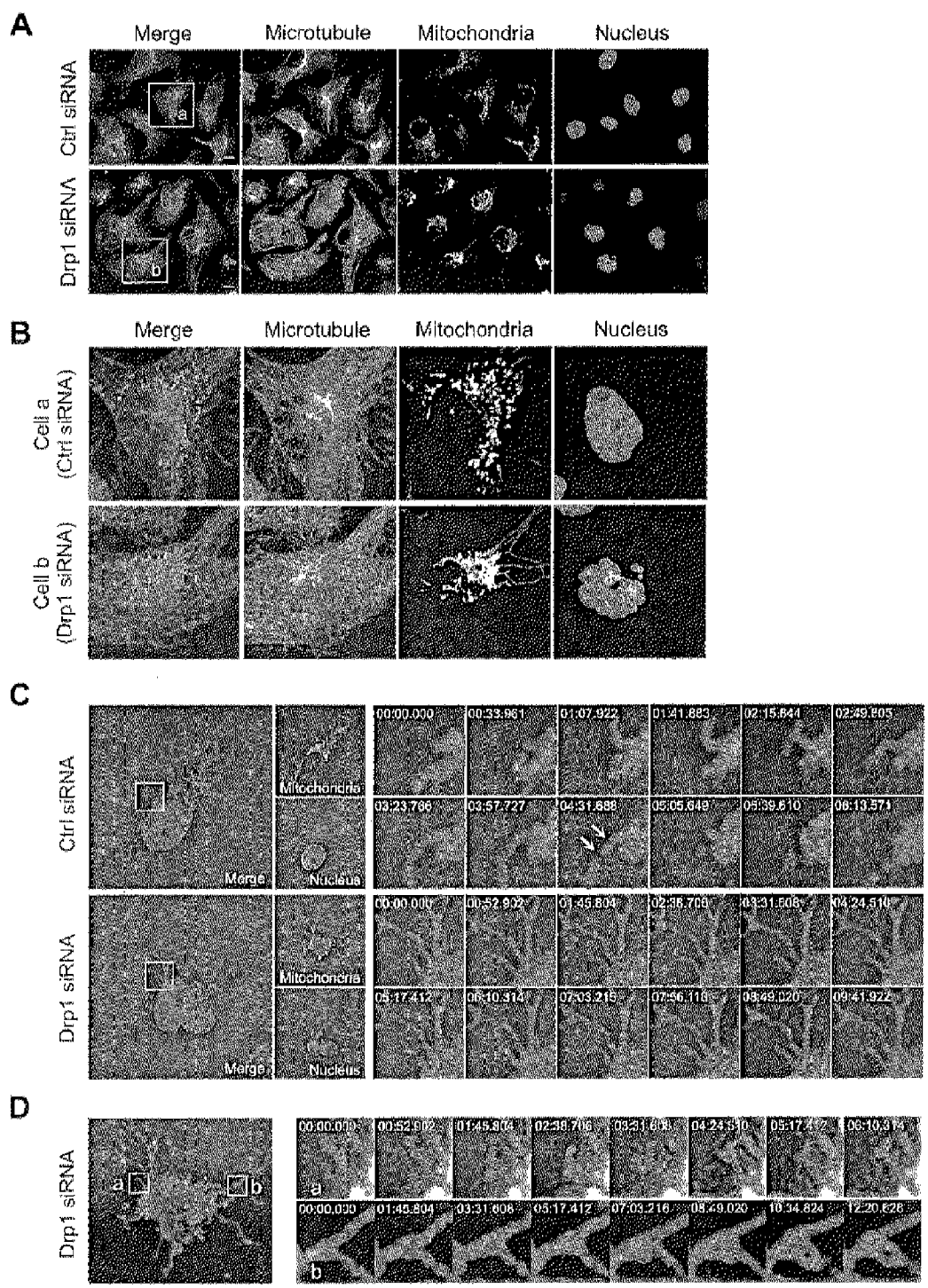

In a second set of experiments, Mdivi-1 dissolved in DMSO was used as stock solution. Mdivi-1 of 50 mM stocks in DMSO was diluted with 40% 2-Hydroxypropyl-β-cyclodextrin/PBS. The final concentration of this formulation of mdivi-1 is 1 mM. MDA-MB-231 cells were treated with HP-β-CD, cisplatin, mdivi-1 alone or in combination in the presence of HP-β-CD as indicated above. After continuous exposure for 20 h, cell death was determined by measuring the activity of caspase 3/7. As shown in FIG. 5, the results of these experiments indicate that 2-Hydroxypropyl-β-cyclodextrin (HP-β-CD) can be used to improve the solubility of mdivi-1, and maintain the synergistic cell killing effect with the combination of mdivi-1 and cisplatin. Data represent mean±SD. n=4 wells.

9. REFERENCES

Bartkova, J., Z. Horejsi, K. Koed, A. Kramer, F. Tort, K. Zieger, P. Guldberg, M. Sehested, J. M. Nesland, C. Lukas, T. Orntoft, J. Lukas, and J. Bartek. 2005. DNA damage response as a candidate anti-cancer barrier in early human tumorigenesis. Nature. 434:864-870.

Cassidy-Stone, A., J. E. Chipuk, E. Ingerman, C. Song, C. Yoo, T. Kuwana, M. J. Kurth, J. T. Shaw, J. E. Hinshaw, D. R. Green, and J. Nunnari. 2008. Chemical inhibition of the mitochondrial division dynamin reveals its role in Bax/Bak-dependent mitochondrial outer membrane permeabilization. Dev Cell. 14:193-204.

Chian, Y-Y, S-L Chen, Y-T hsiao, C-H Huang, T-Y Lin, I-P Chiang, W-H Hsu, and K-C Chow. 2009. Nuclear expression of dnamin-related protein 1 in lung adenocarcinomas. Modern Pathol. 22:1139-1150.

Cho, D. H., T. Nakamura, J. Fang, P. Cieplak, A. Godzik, Z. Gu, and S. A. Lipton. 2009. S-nitrosylation of Drp1 mediates beta-amyloid-related mitochondrial fission and neuronal injury. Science. 324:102-105.

Cimprich, K. A., and D. Cortez. 2008. ATR: an essential regulator of genome integrity. Nat Rev Mal Cell Biol. 9:616-627.

Cipolat, S., O. Martins de Brito, B. Dal Zilio, and L. Scorrano. 2004. OPA1 requires mitofusin 1 to promote mitochondrial fusion. Proc Natl Acad Sci USA. 101:15927-15932.

Crosio, C., G. M. Fimia, R. Lowy, M. Kimura, Y. Okano, H. Zhou, S. Sen, C. D. Allis, and P. Sassone-Corsi. 2002. Mitotic phosphorylation of histone H3: spatio-temporal regulation by mammalian Aurora kinases. Mol Cell Biol. 22:874-885.

Doree, M., and T. Hunt. 2002. From Cdc2 to Cdk1: when did the cell cycle kinase join its cyclin partner? J Cell Sci. 115:2461-2464.

Ekholm, S. V., and S. I. Reed. 2000. Regulation of G(1) cyclin-dependent kinases in the mammalian cell cycle. Curr Opin Cell Biol. 12:676-684.

Ekholm, S. V., P. Zickert, S. I. Reed, and A. Zetterberg. 2001. Accumulation of cyclin E is not a prerequisite for passage through the restriction point. Mol Cell Biol. 21:3256-3265.

Ekholm-Reed, S., J. Mendez, D. Tedesco, A. Zetterberg, B. Stillman, and S. I. Reed. 2004. Deregulation of cyclin E in human cells interferes with prereplication complex assembly. J Cell Biol. 165:789-800.

Fukasawa, K. 2007. Oncogenes and tumour suppressors take on centrosomes. Nat Rev Cancer. 7:911-924.

Ganem, N. J., S. A. Godinho, and D. Pellman. 2009. A mechanism linking extra centrosomes to chromosomal instability. Nature. 460:278-282.

Gorgoulis, V. G., L. V. Vassiliou, P. Karakaidos, P. Zacharatos, A. Kotsinas, T. Liloglou, M. Venere, R. A. Ditullio, Jr., N. G. Kastrinakis, B. Levy, D. Kletsas, A. Yoneta, M. Herlyn, C. Kittas, and T. D. Halazonetis. 2005. Activation of the DNA damage checkpoint and genomic instability in human precancerous lesions. Nature. 434:907-913.

Green, D. R., and B. Van Houten. 2011. SnapShot: Mitochondrial quality control. Cell. 147:950, 950 e951.

Hemerly, A. S., S. G. Prasanth, K. Siddiqui, and B. Stillman. 2009. Orc1 controls centriole and centrosome copy number in human cells. Science. 323:789-793.

Inanc, B., H. Dodson, and C. G. Morrison. 2010. A centrosome-autonomous signal that involves centriole disengagement permits centrosome duplication in G2 phase after DNA damage. Mol Biol Cell. 21:3866-3877.

Ishihara, N., M. Nomura, A. Jofuku, H. Kato, S. O. Suzuki, K. Masuda, H. Otera, Y. Nakanishi, I. Nonaka, Y. Goto, N. Taguchi, H. Morinaga, M. Maeda, R. Takayanagi, S. Yokota, and K. Mihara. 2009. Mitochondrial fission factor Drp1 is essential for embryonic development and synapse formation in mice. Nat Cell Biol. 11:958-966.

Jones, R. G., D. R. Plas, S. Kubek, M. Buzzai, J. Mu, Y. Xu, M. J. Birnbaum, and C. B. Thompson. 2005. AMP-activated protein kinase induces a p53-dependent metabolic checkpoint. Mol Cell. 18:283-293.

Kanda, T., K. F. Sullivan, and G. M. Wahl. 1998. Histone-GFP fusion protein enables sensitive analysis of chromosome dynamics in living mammalian cells. Curr Biol. 8:377-385.

Kashatus D F, Lim K H, Brady D C, Pershing N L, Cox A D, Counter C M. RALA and RALBP1 regulate mitochondrial fission at mitosis. Nat Cell Biol. 2011 Aug. 7; 13(9):1108-15.

Kastan, M. B., and J. Bartek. 2004. Cell-cycle checkpoints and cancer. Nature. 432:316-323.

Keck, J. M., M. K. Summers, D. Tedesco, S. Ekholm-Reed, L. C. Chuang, P. K. Jackson, and S. I. Reed. 2007. Cyclin E overexpression impairs progression through mitosis by inhibiting APC(Cdh1). J Cell Biol. 178:371-385.

King, M. P., and G. Attardi. 1996. Isolation of human cell lines lacking mitochondrial DNA. Methods Enzymol. 264:304-313.

Labrousse, A. M., M. D. Zappaterra, D. A. Rube, and A. M. van der Bliek. 1999. *C. elegans* dynamin-related protein DRP-1 controls severing of the mitochondrial outer membrane. Mol Cell. 4:815-826.

Lew, D. J., and S. Kornbluth. 1996. Regulatory roles of cyclin dependent kinase phosphorylation in cell cycle control. Curr Opin Cell Biol. 8:795-804.

Liberal, V., H. S. Martinsson-Ahlzen, J. Liberal, C. H. Spruck, M. Widschwendter, C. H. McGowan, and S. I. Reed. 2011. Breast Cancer Special Feature: Cyclin-dependent kinase subunit (Cks) 1 or Cks2 overexpression overrides the DNA damage response barrier triggered by activated oncoproteins. Proc Natl Acad Sci USA.

Listovsky, T., Y. S. Oren, Y. Yudkovsky, H. M. Mahbubani, A. M. Weiss, M. Lebendiker, and M. Brandeis. 2004. Mammalian Cdh1/Fzr mediates its own degradation. EMBO J. 23:1619-1626.

Macia et al. 2006. Dynasore, a cell-permeable inhibitor of dynamin. Dev. Cell 10:839-850.

Malena, A., E. Loro, M. Di Re, I. J. Holt, and L. Vergani. 2009. Inhibition of mitochondrial fission favours mutant over wild-type mitochondrial DNA. Hum Mol Genet. 18:3407-3416.

Mandal, S., P. Guptan, E. Owusu-Ansah, and U. Banerjee. 2005. Mitochondrial regulation of cell cycle progression during development as revealed by the tenured mutation in *Drosophila*. Dev Cell. 9:843-854.

Matsumoto, Y., and J. L. Mailer. 2002. Calcium, calmodulin, and CaMKII requirement for initiation of centrosome duplication in *Xenopus* egg extracts. Science. 295:499-502.

Mitra, K., C. Wunder, B. Roysam, G. Lin, and J. Lippincott-Schwartz. 2009. A hyperfused mitochondrial state achieved at G1-S regulates cyclin E buildup and entry into S phase. Proc Natl Acad Sci USA. 106:11960-11965.

Murga, M., S. Bunting, M. F. Montana, R. Soria, F. Mulero, M. Canamero, Y. Lee, P. J. McKinnon, A. Nussenzweig, and O. Fernandez-Capetillo. 2009. A mouse model of ATR-Seckel shows embryonic replicative stress and accelerated aging. Nat Genet. 41:891-898.

Nakayama, K., H. Nagahama, Y. A. Minamishima, M. Matsumoto, I. Nakamichi, K. Kitagawa, M. Shirane, R. Tsunematsu, T. Tsukiyama, N. Ishida, M. Kitagawa, and S. Hatakeyama. 2000. Targeted disruption of Skp2 results in accumulation of cyclin E and p27(Kip1), polyploidy and centrosome overduplication. EMBO J. 19:2069-2081.

Norbury, C., J. Blow, and P. Nurse. 1991. Regulatory phosphorylation of the p34cdc2 protein kinase in vertebrates. EMBO J. 10:3321-3329.

Owusu-Ansah, E., A. Yavari, S. Mandal, and U. Banerjee, 2008. Distinct mitochondrial retrograde signals control the G1-S cell cycle checkpoint. Nat Genet. 40:356-361.

Parone, P. A., S. Da Cruz, D. Tondera, Y. Mattenberger, D. I. James, P. Maechler, F. Barja, and J. C. Martinou. 2008. Preventing mitochondrial fission impairs mitochondrial function and leads to loss of mitochondrial DNA. PLoS One. 3:e3257.

Qian, W., and B. Van Houten. 2010. Alterations in bioenergetics due to changes in mitochondrial DNA copy number. Methods. 51:452-457.

Rajagopalan, H., P. V. Jallepalli, C. Rago, V. E. Velculescu, K. W. Kinzler, B. Vogelstein, and C. Lengauer. 2004. Inactivation of hCDC4 can cause chromosomal instability. Nature. 428:77-81.

Rajagopalan, H., and C. Lengauer. 2004. Aneuploidy and cancer. Nature. 432:338-341.

Reaper et al. 2011. Selective killing of ATM- or p53-deficient cancer cells through inhibition of ATR. Nature Chem Biol. 7:428-430.

Smirnova, E., L. Griparic, D. L. Shurland, and A. M. van der Bliek. 2001. Dynamin-related protein Drp1 is required for mitochondrial division in mammalian cells. Mol Biol Cell. 12:2245-2256.

Smirnova, E., D. L. Shurland, S. N. Ryazantsev, and A. M. van der Bliek. 1998. A human dynamin-related protein controls the distribution of mitochondria. J Cell Biol. 143:351-358.

Spruck, C. H., K. A. Won, and S. I. Reed. 1999. Deregulated cyclin E induces chromosome instability. Nature. 401:297-300.

Sugioka, R., S. Shimizu, and Y. Tsujimoto. 2004. Fzol, a protein involved in mitochondrial fusion, inhibits apoptosis. J Biol Chem. 279:52726-52734.

Taguchi, N., N. Ishihara, A. Jofuku, T. Oka, and K. Mihara. 2007. Mitotic phosphorylation of dynamin-related GTPase Drp1 participates in mitochondrial fission. J Biol Chem. 282:11521-11529.

Toledo, L. I., M. Murga, P. Gutierrez-Martinez, R. Soria, and O. Fernandez-Capetillo. 2008. ATR signaling can drive cells into senescence in the absence of DNA breaks. Genes Dev. 22:297-302.

Toledo, L. I., M. Murga, R. Zur, R. Soria, A. Rodriguez, S. Martinez, J. Oyarzabal, J. Pastor, J. R. Bischoff, and O. Fernandez-Capetillo. 2011. A cell-based screen identifies ATR inhibitors with synthetic lethal properties for cancer-associated mutations. Nat Struct Mol Biol. 18:721-727.

Twig, G., A. Elorza, A. J. Molina, H. Mohamed, J. D. Wikstrom, G. Walzer, L. Stiles, S. E. Haigh, S. Katz, G. Las, J. Alroy, M. Wu, B. F. Py, J. Yuan, J. T. Deeney, B. E. Corkey, and O. S. Shirihai. 2008. Fission and selective fusion govern mitochondrial segregation and elimination by autophagy. EMBO J. 27:433-446.

Wakabayashi, J., Z. Zhang, N. Wakabayashi, Y. Tamura, M. Fukaya, T. W. Kensler, M. Iijima, and H. Sesaki. 2009. The dynamin-related GTPase Drp1 is required for embryonic and brain development in mice. J Cell Biol. 186:805-816.

Wang, X., B. Su, H. Fujioka, and X. Zhu. 2008. Dynamin-like protein 1 reduction underlies mitochondrial morphology and distribution abnormalities in fibroblasts from sporadic Alzheimer's disease patients. Am J Pathol. 173:470-482.

Warburg, O., F. Wind, and E. Negelein. 1927. The Metabolism of Tumors in the Body. J Gen Physiol. 8:519-530.

Waterham, H. R., J. Koster, C. W. van Roermund, P. A. Mooyer, R. J. Wanders, and J. V. Leonard. 2007. A lethal defect of mitochondrial and peroxisomal fission. N Engl J Med. 356:1736-1741.

Weinberg, F., R. Hamanaka, W. W. Wheaton, S. Weinberg, J. Joseph, M. Lopez, B. Kalyanaraman, G. M. Mutlu, G. R. Budinger, and N. S. Chandel. 2010. Mitochondrial metabolism and ROS generation are essential for Kras-mediated tumorigenicity. Proc Natl Acad Sci USA. 107:8788-8793.

Westermann, B. 2010. Mitochondrial fusion and fission in cell life and death. Nat Rev Mol Cell Biol. 11:872-884.

White, J. S., S. Choi, and C. J. Bakkenist. 2008. Irreversible chromosome damage accumulates rapidly in the absence of ATM kinase activity. Cell Cycle. 7:1277-1284.

Yoon, Y. S., D. S. Yoon, I. K. Lim, S. H. Yoon, H. Y. Chung, M. Rojo, F. Malka, M. J. Jou, J. C. Martinou, and G. Yoon. 2006. Formation of elongated giant mitochondria in DFO-induced cellular senescence: involvement of enhanced fusion process through modulation of Fis1. J Cell Physiol. 209:468-480.

Various publications are cited herein, the contents of which are hereby incorporated by reference in their entireties herein. Various nucleic acid and amino acid sequence accession numbers are cited herein, and the complete sequences referenced by those accession numbers are hereby incorporated by reference in their entireties herein.

We claim:

1. A method for reducing cancer cell proliferation or promoting cancer cell death by administering, to a cancer cell, an effective amount of

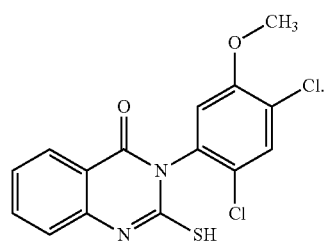 [SMILES: COc1cc(-n2c(S)nc3ccccc3c2=O)c(Cl)cc1Cl]

2. The method of claim 1, further comprising administering, to the cell, an effective amount of a second antiproliferative agent.

3. The method of claim 2 where the second antiproliferative agent is a platinum compound.

4. The method of claim 3 where the platinum compound is cisplatin.

5. The method of claim 3 where the platinum compound is carboplatin.

6. The method of claim 4 where the cisplatin is bound to albumin carrier.

7. A method for reducing cancer cell proliferation or promoting cancer cell death in a subject in need of such treatment comprising administering, to the subject, an effective amount of

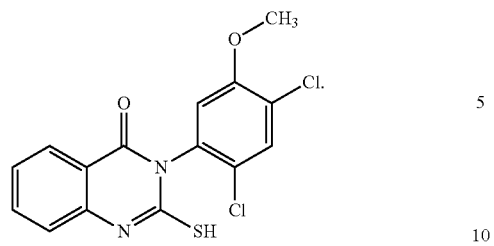

8. The method of claim 7, where the cancer is selected from the group consisting of breast cancer, lung cancer, and glioblastoma.

9. The method of claim 7, further comprising administering, to the cell, an effective amount of a second antiproliferative agent.

10. The method of claim 9 where the second antiproliferative agent is a platinum compound.

11. The method of claim 10 where the platinum compound is cisplatin.

12. The method of claim 11 where the cisplatin is bound to albumin carrier.

13. The method of claim 10 where the platinum compound is carboplatin.

14. The method of claim 7 where the cancer is ovarian cancer.

* * * * *